(12) United States Patent
Buil Albero et al.

(10) Patent No.: US 7,960,383 B2
(45) Date of Patent: Jun. 14, 2011

(54) PYRIDAZIN-3(2H)-ONE DERIVATIVES AND THEIR USE AS PDE4 INHIBITORS

(75) Inventors: Antonia Maria Buil Albero, Barcelona (ES); Vittorio Dal Piaz, Impruneta (IT); Yolanda Garrido Rubio, Zaragoza (ES); Jordi Gracia Ferrer, Barcelona (ES); Lluis Miquel Pages Santacana, Barcelona (ES); Joan Taltavull Moll, Barcelona (ES)

(73) Assignee: Laboratorios Almirall SA, Barcelona (ES)

( * ) Notice: Subject to any disclaimer, the term of this patent is extended or adjusted under 35 U.S.C. 154(b) by 545 days.

(21) Appl. No.: 11/629,522

(22) PCT Filed: Jun. 13, 2005

(86) PCT No.: PCT/EP2005/006304
§ 371 (c)(1),
(2), (4) Date: Jun. 2, 2008

(87) PCT Pub. No.: WO2005/123692
PCT Pub. Date: Dec. 29, 2005

(65) Prior Publication Data
US 2008/0280918 A1    Nov. 13, 2008

(30) Foreign Application Priority Data

Jun. 18, 2004    (ES) .................................. 200401500

(51) Int. Cl.
C07D 401/12 (2006.01)
A61K 31/501 (2006.01)
A61P 29/00 (2006.01)
A61P 11/06 (2006.01)
A61P 19/02 (2006.01)
A61P 17/00 (2006.01)
A61P 17/06 (2006.01)

(52) U.S. Cl. ................ 514/252.03; 514/252.04; 544/238
(58) Field of Classification Search .................. 544/238; 514/252.03, 252.04
See application file for complete search history.

(56) References Cited

U.S. PATENT DOCUMENTS

| | | |
|---|---|---|
| 5,679,696 A | 10/1997 | Fenton et al. |
| 5,804,588 A | 9/1998 | Dyke et al. |
| 5,859,008 A | 1/1999 | Jonas et al. |
| 5,972,936 A | 10/1999 | Dyke et al. |
| 6,025,376 A | 2/2000 | Laurent et al. |
| 6,162,830 A | 12/2000 | Connor et al. |
| 6,204,275 B1 | 3/2001 | Friesen et al. |
| 6,699,890 B2 | 3/2004 | Schumacher et al. |
| 7,087,625 B2 | 8/2006 | Schumacher et al. |
| 7,226,930 B2 | 6/2007 | Hopper et al. |
| 7,235,579 B2 | 6/2007 | Liu et al. |
| 7,273,875 B2 | 9/2007 | Denholm et al. |
| 7,459,453 B2 | 12/2008 | Dal Piaz et al. |
| 7,491,722 B2 | 2/2009 | Dal Piaz et al. |
| 7,511,038 B2 | 3/2009 | Dal Piaz et al. |
| 2006/0052379 A1 | 3/2006 | Dal Piaz et al. |
| 2007/0197536 A1 | 8/2007 | Dal Piaz et al. |
| 2008/0269235 A1 | 10/2008 | Dal Piaz et al. |
| 2009/0029996 A1 | 1/2009 | Aguilar Izquierdo et al. |
| 2009/0111819 A1 | 4/2009 | Dal Piaz et al. |

FOREIGN PATENT DOCUMENTS

| | | |
|---|---|---|
| DE | 2 225 218 | 12/1973 |
| GB | 1351569 | 5/1974 |
| SU | 405344 | 8/1975 |
| WO | WO 93/07146 | 5/1993 |
| WO | WO 97/15561 | 5/1997 |
| WO | WO 99/06404 | 2/1999 |
| WO | WO 00/24719 | 5/2000 |
| WO | WO 01/46184 | 6/2001 |
| WO | WO 01/94319 | 12/2001 |
| WO | WO 01/94391 | 12/2001 |
| WO | WO 03/097613 | 11/2003 |
| WO | WO 03/097613 A1 | 11/2003 |
| WO | WO 2004/058729 | 7/2004 |
| WO | WO 2005049581 | * 11/2004 |
| WO | WO 2005/049581 | 6/2005 |

(Continued)

OTHER PUBLICATIONS

Naldi, et al., Expert Opin. Emerging Drugs (2009) 14(1) 145-163.*
Targan, et al., Inflammatory Bowel Disease: From Bench to Bedside, 2nd Edition, pp. 553-571, 2003.*
Prehn, et al., J. Clin. Immunol., vol. 21, No. 5, 2001, pp. 357-364.*
"Glenmark stops oglemilast (GRC3886) development programme for COPD and asthma with Forest." May 20, 2010, <http//expresslayout.com/pharmaceuticallitigation/?p=696> Downloaded from the internet May 31, 2010.*

(Continued)

Primary Examiner — James O Wilson
Assistant Examiner — Cecilia M Jaisle
(74) Attorney, Agent, or Firm — Finnegan, Henderson, Farabow, Garrett & Dunner LLP

(57) ABSTRACT

The invention relates to new therapeutically useful pyridazin-3(2H)-one derivatives of Formula (I) and to pharmaceutical compositions containing them. These compounds are potent and selective inhibitors of phosphodiesterase 4 (PDE4) and are thus useful in the treatment, prevention or suppression of pathological conditions, diseases and disorders known to be susceptible of being improved by inhibition of PDE4 such as asthma, chronic obstructive pulmonary disease, rheumatoid arthritis, atopic dermatitis, psoriasis or irritable bowel disease.

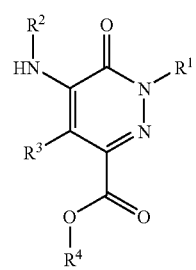

(I)

12 Claims, No Drawings

FOREIGN PATENT DOCUMENTS

| WO | WO 2005/123692 | 12/2005 |
|---|---|---|
| WO | WO 2005/123693 | 12/2005 |
| WO | WO 2007/084560 | 7/2007 |
| WO | WO 2008/107064 | 9/2008 |

OTHER PUBLICATIONS

V. Dal Piaz, 5-Acyl-6-aryl-4-nitro-3(2H)pyridazinones and Related 4-Amino Compounds: Synthesis and Pharmacological Evaluation, J. Pharmaceutical Sciences, 1991, 341-348, 80(4).
V. Dal Piaz, 4,5-Functionalized 6-phenyl-3(2H)-pyridazinones: synthesis and evaluation of antinociceptive activity, Eur. J..Med. Chem., 1996, 65-70, 31.
L. Constantino, Isoxazolo-[3,4-d]-pyridazin-7-(6H)-one as a Potential Substrate for New Aldose Reductase Inhibitors, J. Med. Chem., 1999, 1894-1900, 42.
U.S. Appl. No. 12/141,712, filed Jun. 18, 2008, Dal Piaz et al.
U.S. Appl. No. 12/247,688, filed Oct. 8, 2008, Dal Piaz et al.
U.S. Appl. No. 12/529,511, filed Nov. 18, 2009, Hereu.
U.S. Appl. No. 10/578,594, filed Feb. 15, 2007, Dal Piaz et al.
U.S. Appl. No. 11/629,527, filed Dec. 14, 2006.
U.S. Appl. No. 10/578,594, filed Jan. 12, 2007.
Barlocco, Daniela et al., Phenylpiperazinylalkylamino Substituted Pyridazinones as Potent α1 Adrenoceptor Antagonists, J. Med. Chem., 44:2403-2410 (2001).
Baumer, et al., Inflammation & Allergy—Drug Targets, vol. 6, No. 1, Mar. 2007, pp. 17-26 (10).
Bulka E., et al., Zeitschrift Für Chemie, 5(10):374-375 (1965).
Caplus Abstract for SU 405344, Accession No. 1976:4988 dated May 12, 1984.
Calverley et al., The Lancet, 374: 685-694 (2009).
Ciciani, Giovanna et al., "Synthesis and Evaluation of In Vitro Antitumor Activity of Some Substituted 5-Pyridazinyl-Styrylketones," Il Farmaco, 46 (7,8)873-885 (1991).
Diaz-Granados, Natalia et al., "Dextran sulfate sodium-induced colonic histopathology, but not altered epithelial ion transport, is reduced by inhibition of phosphodiesterase activity," American Journal of Pathology, 156(6):2169-2177 (2000).
Dyke, Hazel J., et al., "The therapeautic potential of PDE4 inhibitors," Exp. Opin. Invest. Drugs, 8(9):1301-1325 (1999).
English-language abstract for W0 97/15561 (May 1, 1997).
English-language machine translation of DE 2 225 218 from esp@cenet database (Dec. 20, 1973).
Entry No. 3603 for Emorfazone in Merck Index (1994).
Essayan, David M., "Cyclic nucleotide phosphodiesterase (PDE) inhibitors and immunomodulation," Biochemical Pharmacology, 57:965-973 (1999).
European Respiratory Society, Feb. 13, 2007, http://www.netocopd.com/currentaffairsnews/list751_item17680.aspx, downloaded Jan. 16, 2008.
Fabbri et al., The Lancet, 374: 695-703 (2009).
Gilhar, A., et al., "Antiproliferative effect of pentoxifylline on psoriatic and normal epidermis," Acta Derm Venereol, 76:437-441 (1996).
Griffiths, et al., British J. of Dermatology, 147:299-307 (2002).
Hanifin, Jon M., et al., "Type 4 phosphodiesterase inhibitors have clinical and in vitro anti-inflammatory effects in atopic dermatitis," Journal of Investigative Dermatology, 107(1):51-56 (1996).
Hartmann, Gunther et al., "Specific type IV phosphodiesterase inhibitor rolipram mitigates experimental colitis in mice," Journal of Pharmacology and Experimental Therapeutics, 292(1):22-30 (2000). Implications for Rheumatoid Arthritis http://www.medscape.com/viewarticle/464104_4, downloaded Jul. 8, 2007.
International Search Report for PCT/EP2008/001080 dated May 16, 2008.
International Search Report for PCT/EP2004/012604, dated Feb. 11, 2005.
International Search Report for PCT/EP2003/014772 dated Mar. 10, 2004.
International Search Report for PCT/EP2009/008794 dated Feb. 25, 2010.
International Search Report for PCT/EP2005/006712 dated Nov. 16, 2005.
International Search Report for PCT/EP2005/006304 dated Nov. 7, 2005.
International Search Report for PCT/EP2003/05056 dated Oct. 2, 2003.
Lipworth, Lancet, 365:167-175 (2005).
MacKenzie, "Phosphodiesterase 4 cAMP phosphodiesterasesas targets for novel anti-inflammatory therapeutics," Alergology International, 53:101-110 (2004).
Marks, Andrew R., "Drugs in trials for asthma, alzheimer's and chronic lung disease may cause heart disease," Columbia University Medical Center press release, http://www.cumc.columbia.edu/news/press_releases/Marks_Cell.html, downloaded Jul. 9, 2007.
Nicholson, C. David, et al., "Differential modulation of tissue function and therapeutic potential of selective inhibitors of cyclic nucleotide phosphodiesterase isoenzymes," TiPS, 12:19-27 (1991).
Notice of Allowance dated Mar. 19, 2008 in U.S. Appl. No. 10/513,219.
Notice of Allowance dated Nov. 28, 2008 in U.S. Appl. No. 10/578,594.
Notice of Allowance dated Jul. 9, 2008 in U.S. Appl. No. 10/539,821.
Nycomed, Press Release, Nycomed files European marketing authorization application for Daxas® in COPD, (Mar. 8, 2009).
Nycomed, Press Release, Nycomed announced FDA filing for Daxas® in COPD, (Jul. 20, 2009).
Nyman, U., et al., "Amelioration of collagen II-induced arthritis in rats by the type IV phosphodiesterase inhibitor rolipram," Clin. Exp. Immunol, 108:415-419 (1997).
Office Action dated May 15, 2008, in U.S. Appl. No. 10/578,594.
Office Action dated Nov. 27, 2007 in U.S. Appl. No. 10/513,219.
Office Action dated Nov. 20, 2006 in U.S. Appl. No. 10/513,219.
Office Action dated Jul. 2, 2007 in U.S. Appl. No. 10/513,219.
Office Action dated Jul. 18, 2007 in U.S. Appl. No. 10/513,219.
Office Action dated Feb. 4, 2008 in U.S. Appl. No. 10/539,821.
Office Action dated Sep. 19, 2007 in U.S. Appl. No. 10/539,821.
Office Action dated May 29, 2009 in U.S. Appl. No. 12/141,712.
Phosphodiesterases: A drug target family with board therapeutic impact, http://www.piribo.com/publications/drug_discovery/DMD045,html, downloaded Jul. 9, 2007.
Renzi et al., Ed. Scientifica, 1969, vol. 24, n° 10, 885-892.
Renzi, Giovanni et al., "Condensazioni tra cloruri di acidi idrossammici e composte β-oxobenzoilici," Gaz. Chi. Ital., 1967, 57: 823-845.
Ross, Susan E., et al., "Suppression of TNF-α expression, inhibition of Th1 activity, and amerlioration of collagen-induced arthritis by rolipram," Journal of Immunology, pp. 6253-6259 (1997).
Sato, M. et al., "Studies on Mechanisms of Action of Emorfazone," Arznem. Forsch./Drug Res., 32(I)(4):379-382 (1983).
Sekut, L., et al., "Anti-inflammatory activity of phosphodiesterase (PDE)-IV inhibitors in acute and chronic models of inflammation," Clin. Exp. Immunol, 100:126-132 (1995).
Solomons, T. W. G., Organic Chemistry, John Wiley & Sons, Inc., pp. 463-468, 485-486 (1978).
Spanish Search Report for P 200203003 dated May 17, 2004.
Spina, "Drugs," 63(23):2575-2594 (2003).
Sprio, Vincenzo et al., "Nitrogen Heterocycles. II. Hydrogenation of isoxazolo[3,4-d]pyridazin-7-ones, isoxazolo[3,4-d]pyridazin-4-ones, and isoxazolo[3,4-d]pyridazin-4,7-ones," Annali Di Chimica (Rome, Italy), 1967, 57(7): 836-845.
Stawiski, Marek A., et al., "Ro 20-1724: an agent that significantly improves psoriatic lesions in double-blind clinical trials," The Journal of Investigative Dermatology, 73(4):261-263 (1979).
Teixeira, Mauro M., et al., "Phosphodiesterase (PDE)4 inhibitors: anti-inflammatory drugs of the future?," TiPS, 18:164-170 (1997).
Torphy, "Phosphodiesterase Isozymes: Molecular Targets for Novel Antiasthmatic Agents" American Journal of Respiratory and Critical Care Medicine, 154: 351-370 (1998).

Van der Mey, Margaretha et al., "Novel selective PDE4 Inhibitors. 1. Synthesis, structure-activity relationships, and molecular modeling of 4-(3, 4-dimethoxyphenyl)-2H-phthalazin-1-ones and analogues," Journal of Medicinal Chemistry, 44(16):2511-2522 (2001).

Wikipedia, "Phosphodiesterase," http://en.wikipedia.org/wiki/Phosphodoesterase, downloaded May 31, 2007.

Wikipedia, COPD, <http://en.wikipedia.org/wiki/COPD, downloaded May 30, 2007.

Wikipedia, "Inflammatory bowel disease," http://en.wikipedia.org/wiki/IBD, downloaded May 31, 2007.

Yeung, Drug Discovery Today 14(15/16): 812-813 (2009).

International Search Report dated Jul. 21, 2005 for Application No. PCT/EP2005/006304.

* cited by examiner

PYRIDAZIN-3(2H)-ONE DERIVATIVES AND THEIR USE AS PDE4 INHIBITORS

This application is a national stage filing under 35 U.S.C. §371 of International Application No. PCT/EP2005/006304 filed on Jun. 13, 2005. This application claims priority of Spanish Patent Application No. P200401500, filed on Jun. 18, 2004.

The present invention relates to new therapeutically useful pyridazin-3(2H)-one derivatives, to processes for their preparation and to pharmaceutical compositions containing them. These compounds are potent and selective inhibitors of phosphodiesterase 4 (PDE4) and are thus useful in the treatment, prevention or suppression of pathological conditions, diseases and disorders known to be susceptible of being improved by inhibition of PDE4.

Phosphodiesterases (PDEs) comprise a superfamily of enzymes responsible for the hydrolysis and inactivation of the second messengers cyclic adenosine monophosphate (cAMP) and cyclic guanosine monophosphate (cGMP). Eleven different PDE families have been identified to date (PDE1 to PDE11) which differ in substrate preference, catalytic activity, sensitivity to endogenous activators and inhibitors, and encoding genes.

The PDE4 isoenzyme family exhibits a high affinity for cyclic AMP but has weak affinity for cyclic GMP. Increased cyclic AMP levels caused by PDE4 inhibition are associated with the suppression of cell activation in a wide range of inflammatory and immune cells, including lymphocytes, macrophages, basophils, neutrophils, and eosinophils. Moreover, PDE4 inhibition decreases the release of the cytokine Tumor Necrosis Factor α (TNFα). The biology of PDE4 is described in several recent reviews, for example M. D. Houslay, *Prog. Nucleic Acid Res. Mol. Biol.* 2001, 69, 249-315; J. E. Souness et al. *Immunopharmacol.* 2000 47, 127-162; or M. Conti and S. L. Jin, *Prog. Nucleic Acid Res. Mol. Biol.* 1999, 63, 1-38.

In view of these physiological effects, PDE4 inhibitors of varied chemical structures have been recently disclosed for the treatment or prevention of chronic and acute inflammatory diseases and of other pathological conditions, diseases and disorders known to be susceptible to amelioration by inhibition of PDE4. See, for example, U.S. Pat. No. 5,449,686, U.S. Pat. No. 5,710,170, WO 98/45268, WO 99/06404, WO 01/57025, WO 01/57036, WO 01/46184, WO 97/05105, WO 96/40636, WO03/097613, U.S. Pat. No. 5,786,354, U.S. Pat. No. 5,773,467, U.S. Pat. No. 5,753,666, U.S. Pat. No. 5,728,712, U.S. Pat. No. 5,693,659, U.S. Pat. No. 5,679,696, U.S. Pat. No. 5,596,013, U.S. Pat. No. 5,541,219, U.S. Pat. No. 5,508,300, U.S. Pat. No. 5,502,072 or H. J. Dyke and J. G. Montana, *Exp. Opin. Invest. Drugs* 1999, 8, 1301-1325.

A few compounds having the capacity to selectively inhibit phosphodiesterase 4 are in active development. Examples of these compounds are cipamfylline, arofyline, cilomilast, roflumilast, mesopram and pumafentrine.

The international applications WO03/097613 A1, WO2004/058729 A1 and WO 2005/049581 describe pyridazin-3(2H)-one derivatives as potent and selective inhibitors of PDE4. We have now found that the compounds of formula (I) described in more detail below have surprising and particularly advantageous properties.

It is known that the clinical development in man of early PDE4 inhibitors such as rolipram has been hampered by the appearance of side effects such as nausea and vomiting at therapeutic plasma levels (Curr. Pharm. Des. 2002, 8, 1255-96). The compounds described in the present invention are potent and selective PDE4 inhibitors which are hydrolized systemically. This particular property provides the compounds with a high local activity and little or no systemic action, avoiding or reducing the risk of unwanted systemic side effects, and makes them useful for the treatment or prevention of these pathological conditions, diseases and disorders, in particular asthma, chronic obstructive pulmonary disease, rheumatoid arthritis, atopic dermatitis, psoriasis or irritable bowel disease.

The compounds of the present invention can also be used in combination with other drugs known to be effective in the treatment of these diseases. For example, they can be used in combination with steroids or immunosuppressive agents, such as cyclosporin A, rapamycin, T-cell receptor blockers, β2-adrenergic agonists or antagonists of M3 muscarinic receptors. In this case the administration of the compounds allows a reduction of the dosage of the other drugs, thus preventing the appearance of the undesired side effects associated with both steroids and immunosuppressants.

Like other PDE4 inhibitors (see references above) the compounds of the invention can also be used for blocking the ulcerogenic effects induced by a variety of etiological agents, such as antiinflammatory drugs (steroidal or non-steroidal antiinflammatory agents), stress, ammonia, ethanol and concentrated acids. They can be used alone or in combination with antacids and/or antisecretory drugs in the preventive and/or curative treatment of gastrointestinal pathologies like drug-induced ulcers, peptic ulcers, *H. Pylori*-related ulcers, esophagitis and gastro-esophageal reflux disease.

They can also be used in the treatment of pathological situations where damage to the cells or tissues is produced through conditions like anoxia or the production of an excess of free radicals. Examples of such beneficial effects are the protection of cardiac tissue after coronary artery occlusion or the prolongation of cell and tissue viability when the compounds of the invention are added to preserving solutions intended for storage of transplant organs or fluids such as blood or sperm. They are also of benefit on tissue repair and wound healing.

Accordingly, the present invention provides novel compounds of formula (I):

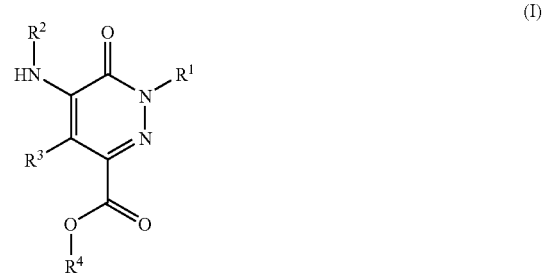

wherein
$R^1$ represents:
  a hydrogen atom;
  an alkyl, alkenyl or alkynyl group, which is optionally substituted by one or more substituents selected from halogen atoms and hydroxy, alkoxy, aryloxy, alkylthio, arylthio, oxo, amino, mono- or di-alkylamino, acylamino, hydroxycarbonyl, alkoxycarbonyl, carbamoyl or mono- or di-alkylcarbamoyl groups;

$R^2$ represents a monocyclic or polycyclic heteroaryl group, which is optionally substituted by one or more substituents selected from:
halogen atoms;
alkyl and alkylene groups, which are optionally substituted by one or more substituents selected from halogen atoms and phenyl, hydroxy, alkoxy, aryloxy, alkylthio, arylthio, oxo, amino, mono- or di-alkylamino, acylamino, hydroxycarbonyl, alkoxycarbonyl, carbamoyl or mono- or di-alkylcarbamoyl groups
phenyl, hydroxy, hydroxycarbonyl, hydroxyalkyl, alkoxycarbonyl, alkoxy, cycloalkoxy, nitro, cyano, aryloxy, alkylthio, arylthio, alkylsulfinyl, alkylsulfonyl, alkylsulfamoyl, acyl, amino, mono- or di-alkylamino, acylamino, hydroxycarbonyl, alkoxycarbonyl, carbamoyl, mono- or di-alkylcarbamoyl, ureido, N'-alkylureido, N',N'-dialkylureido, alkylsulfamido, aminosulphonyl, mono- or di-alkylaminosulfonyl, cyano, difluoromethoxy or trifluoromethoxy groups;
$R^3$ represents a hydrogen atom or an alkylcarbonyl group wherein the alkyl group may be substituted by one or more substituents selected from halogen atoms and phenyl, hydroxy, hydroxyalkyl, alkoxy, aryloxy, alkylthio, arylthio, oxo, amino, mono- or di-alkylamino, acylamino, hydroxycarbonyl, alkoxycarbonyl, carbamoyl, mono- or di-alkylcarbamoyl groups
$R^4$ represents a group of formula:

G-L1-(CRR')$_n$— wherein
n is an integer from 0 to 3
R and R' are independently selected from the group consisting of hydrogen atoms and lower alkyl groups
L1 is a linker selected from the group consisting of a direct bond, a —O—, —CO—, —NR"—, —O(CO)NR"—, —O(CO)O—, —O—(CO)—, —(CO)O—, —NR"—(CO)— and —O(R"O)(PO)O— groups wherein R" is selected from the group consisting of hydrogen atoms and lower alkyl groups, preferably L1 is selected from the group consisting of a direct bond, an oxygen atom, a —CO—, —NR"—, —O(CO)NR"—, —O(CO)O—, —O—(CO)—, R"N—(CO)— and —O(R"O)(PO)O— groups
G is selected from hydrogen atoms and alkyl, alkenyl, alkynyl, cycloalkyl, cycloalkenyl, heterocyclyl, aryl, arylalkyl and heteroaryl groups said groups being optionally substituted with one or more substituents selected from:
halogen atoms;
alkyl and alkenyl groups, which are optionally substituted by one or more substituents selected from halogen atoms; and
hydroxy, alkoxy, cycloalkyloxy, alkylthio, alkylsulfinyl, alkylsulfonyl, alkylsulfamoyl, amino, mono- or di-alkylamino, acylamino, nitro, acyl, hydroxycarbonyl, alkoxycarbonyl, carbamoyl, mono- or di-alkylcarbamoyl, ureido, N'-alkylureido, N',N'-dialkylureido, alkylsulfamido, aminosulphonyl, mono- or di-alkylaminosulfonyl, cyano, difluoromethoxy or trifluoromethoxy groups;
and the pharmaceutically acceptable salts or N-oxides thereof
Further objectives of the present invention are to provide processes for preparing said compounds; pharmaceutical compositions comprising an effective amount of said compounds; the use of the compounds in the manufacture of a medicament for the treatment of diseases susceptible of being improved by inhibition of PDE4; and methods of treatment of diseases susceptible to amelioration by inhibition of PDE4, which methods comprise the administration of the compounds of the invention to a subject in need of treatment.

As used herein the term alkyl embraces optionally substituted, linear or branched radicals having 1 to 20 carbon atoms or, preferably 1 to 12 carbon atoms. More preferably alkyl radicals are "lower alkyl" radicals having 1 to 8, preferably 1 to 6 and more preferably 1 to 4 carbon atoms.

Examples include methyl, ethyl, n-propyl, i-propyl, n-butyl, sec-butyl, t-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

As used herein, the term alkenyl embraces optionally substituted, linear or branched, mono or polyunsaturated radicals having 1 to 20 carbon atoms or, preferably, 1 to 12 carbon atoms. More preferably alkenyl radicals are "lower alkenyl" radicals having 2 to 8, preferably 2 to 6 and more preferably 2 to 4 carbon atoms. In particular it is preferred that the alkenyl radicals are mono or diunsaturated.

Examples include vinyl, allyl, 1-propenyl, isopropenyl, 1-butenyl, 2-butenyl, 3-butenyl, 1-pentenyl, 2-pentenyl, 3-pentenyl and 4-pentenyl radicals.

As used herein, the term alkynyl embraces optionally substituted, linear or branched, mono or polyunsaturated radicals having 1 to 20 carbon atoms or, preferably, 1 to 12 carbon atoms. More preferably, alkynyl radicals are "lower alkynyl" radicals having 2 to 8, preferably 2 to 6 and more preferably 2 to 4 carbon atoms. In particular, it is preferred that the alkynyl radicals are mono or diunsaturated.

Examples include 1-propynyl, 2-propynyl, 1-butynyl, 2-butynyl and 3-butynyl radicals.

When it is mentioned that alkyl, alkenyl or alkynyl radicals may be optionally substituted it is meant to include linear or branched alkyl, alkenyl or alkynyl radicals as defined above, which may be unsubstituted or substituted in any position by one or more substituents, for example by 1, 2 or 3 substituents. When two or more substituents are present, each substituent may be the same or different.

A said optionally substituted alkenyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, substituents on an alkenyl group are themselves unsubstituted.

A said optionally substituted alkynyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, substituents on an alkynyl group are themselves unsubstituted.

A said optionally substituted alkyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, substituents on an alkyl group are themselves unsubstituted. Preferred optionally substituted alkyl groups are unsubstituted or substituted with 1, 2 or 3 fluorine atoms.

As used herein, the term alkylene embraces divalent alkyl moieties typically having from 1 to 6, for example from 1 to 4, carbon atoms. Examples of $C_1$-$C_4$ alkylene radicals include methylene, ethylene, propylene, butylene, pentylene and hexylene radicals.

A said optionally substituted alkylene group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

When an alkylene radical is present as a substituent on another radical it shall be deemed to be a single substituent, rather than a radical formed by two substituents.

As used herein, the term alkoxy (or alkyloxy) embraces optionally substituted, linear or branched oxy-containing radicals each having alkyl portions of 1 to 10 carbon atoms. More preferred alkoxy radicals are "lower alkoxy" radicals having 1 to 8, preferably 1 to 6 and more preferably 1 to 4 carbon atoms.

An alkoxy group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkoxy group are themselves unsubstituted.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy and 2-hydroxypropoxy.

As used herein, the term alkylthio embraces radicals containing an optionally substituted, linear or branched alkyl radicals of 1 to 10 carbon atoms attached to a divalent sulfur atom. More preferred alkylthio radicals are "lower alkylthio" radicals having 1 to 8, preferably 1 to 6 and more preferably 1 to 4 carbon atoms.

An alkylthio group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkylthio group are themselves unsubstituted.

Preferred optionally substituted alkylthio radicals include methylthio, ethylthio, n-propylthio, i-propylthio, n-butylthio, sec-butylthio, t-butylthio, trifluoromethylthio, difluoromethylthio, hydroxymethylthio, 2-hydroxyethylthio and 2-hydroxypropylthio.

As used herein, the term monoalkylamino embraces radicals containing an optionally substituted, linear or branched alkyl radicals of 1 to 10 carbon atoms attached to a divalent —NH— radical. More preferred monoalkylamino radicals are "lower monoalkylamino" radicals having 1 to 8, preferably 1 to 6 and more preferably 1 to 4 carbon atoms.

A monoalkylamino group typically contains an alkyl group which is unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substitutents on a monoalkylamino group are themselves unsubstituted.

Preferred optionally substituted monoalkylamino radicals include methylamino, ethylamino, n-propylamino, i-propylamino, n-butylamino, sec-butylamino, t-butylamino, trifluoromethylamino, difluoromethylamino, hydroxymethylamino, 2-hydroxyethylamino and 2-hydroxypropylamino.

As used herein, the term dialkylamino embraces radicals containing a trivalent nitrogen atoms with two optionally substituted, linear or branched alkyl radicals of 1 to 10 carbon atoms attached thereto. More preferred dialkylamino radicals are "lower dialkylamino" radicals having 1 to 8, preferably 1 to 6 and more preferably 1 to 4 carbon atoms in each alkyl radical.

A dialkylamino group typically contains two alkyl groups, each of which is unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a dialkylamino group are themselves unsubstituted.

Preferred optionally substituted dialkylamino radicals include dimethylamino, diethylamino, methyl(ethyl)amino, di(n-propyl)amino, n-propyl(methyl)amino, n-propyl(ethyl)amino, di(i-propyl)amino, i-propyl(methyl)amino, i-propyl (ethyl)amino, di(n-butyl)amino, n-butyl(methyl)amino, n-butyl(ethyl)amino, n-butyl(i-propyl)amino, di(sec-butyl) amino, sec-butyl(methyl)amino, sec-butyl(ethyl)amino, sec-butyl(n-propyl)amino, sec-butyl(i-propyl)amino, di(t-butyl) amino, t-butyl(methyl)amino, t-butyl(ethyl)amino, t-butyl (n-propyl)amino, t-butyl(i-propyl)amino, trifluoromethyl(methyl)amino, trifluoromethyl(ethyl)amino, trifluoromethyl (n-propyl)amino, trifluoromethyl(i-propyl)amino, trifluoromethyl(n-butyl)amino, trifluoromethyl(sec-butyl)amino, difluoromethyl(methyl)amino, difluoromethyl(ethyl)amino, difluoromethyl(n-propyl)amino, difluoromethyl(i-propyl) amino, difluoromethyl(n-butyl))amino, difluoromethyl(sec-butyl)amino, difluoromethyl(t-butyl)amino, difluoromethyl (trifluoromethyl)amino, hydroxymethyl(methyl)amino, ethyl(hydroxymethyl)amino, hydroxymethyl(n-propyl) amino, hydroxymethyl(i-propyl)amino, n-butyl(hydroxymethyl)amino, sec-butyl(hydroxymethyl)amino, t-butyl(hydroxymethyl)amino, difluoromethyl(hydroxymethyl)amino, hydroxymethyl(trifluoromethyl)amino, hydroxyethyl(methyl)amino, ethyl(hydroxyethyl)amino, hydroxyethyl(n-propyl)amino, hydroxyethyl(i-propyl)amino, n-butyl(hydroxyethyl)amino, sec-butyl(hydroxyethyl)amino, t-butyl (hydroxyethyl)amino, difluoromethyl(hydroxyethyl)amino, hydroxyethyl(trifluoromethyl)amino, hydroxypropyl(methyl)amino, ethyl(hydroxypropyl)amino, hydroxypropyl(n-propyl)amino, hydroxypropyl(i-propyl)amino, n-butyl(hydroxypropyl)amino, sec-butyl(hydroxypropyl)amino, t-butyl (hydroxypropyl)amino, difluoromethyl(hydroxypropyl) amino, hydroxypropyl(trifluoromethyl)amino.

As used herein, the term hydroxyalkyl embraces linear or branched alkyl radicals having 1 to 10 carbon atoms, preferably 1 to 6 carbon atoms, any one of which may be substituted with one or more hydroxyl radicals.

Examples of such radicals include hydroxymethyl, hydroxyethyl, hydroxypropyl, hydroxybutyl and hydroxyhexyl.

As used herein, the term alkoxycarbonyl embraces optionally substituted, linear or branched radicals each having alkyl portions of 1 to 10 carbon atoms and attached to an oxycarbonyl radical. More preferred alkoxycarbonyl radicals are "lower alkoxycarbonyl" radicals, in which the alkyl moiety has 1 to 8, preferably 1 to 6 and more preferably 1 to 4 carbon atoms.

An alkoxycarbonyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkoxycarbonyl group are themselves unsubstituted.

Preferred optionally substituted alkoxycarbonyl radicals include methoxycarbonyl, ethoxycarbonyl, n-propoxycarbonyl, i-propoxycarbonyl, n-butoxycarbonyl, sec-butoxycarbonyl, t-butoxycarbonyl, trifluoromethoxycarbonyl, difluoromethoxycarbonyl, hydroxymethoxycarbonyl, 2-hydroxyethoxycarbonyl and 2-hydroxypropoxycarbonyl.

As used herein, the term monoalkylcarbamoyl embraces radicals containing an optionally substituted, linear or branched alkyl radicals of 1 to 10 carbon atoms and attached to the nitrogen of a-NHCO— radical. More preferred monoalkylcarbamoyl radicals are "lower monoalkylcarbamoyl" radicals in which the alkyl moiety has 1 to 8, preferably 1 to 6 and more preferably 1 to 4 carbon atoms.

A monoalkylcarbamoyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a monoalkylcarbamoyl group are themselves unsubstituted.

Preferred optionally substituted monoalkylcarbamoyl radicals include methylcarbamoyl, ethylcarbamoyl, n-propylcarbamoyl, i-propylcarbamoyl, n-butylcarbamoyl, sec-butylcarbamoyl, t-butylcarbamoyl, trifluoromethylcarbamoyl, difluoromethylcarbamoyl, hydroxymethylcarbamoyl, 2-hydroxyethylcarbamoyl and 2-hydroxypropylcarbamoyl.

As used herein, the term dialkylcarbamoyl embraces radicals containing a radical NCO— where the nitrogen is attached to two optionally substituted, linear or branched alkyl radicals of 1 to 10 carbon atoms. More preferred dialkylcarbamoyl radicals are "lower dialkylcarbamoyl" radicals having 1 to 8, preferably 1 to 6 and more preferably 1 to 4 carbon atoms in each alkyl radical.

A dialkylcarbamoyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a dialkylcarbamoyl group are themselves unsubstituted.

Preferred optionally substituted dialkylcarbamoyl radicals include dimethylcarbamoyl, diethylcarbamoyl, methyl(ethyl)carbamoyl, di(n-propyl)carbamoyl, n-propyl(methyl)carbamoyl, n-propyl(ethyl)carbamoyl, di(i-propyl)carbamoyl, i-propyl(methyl)carbamoyl, i-propyl(ethyl)carbamoyl, di(n-butyl)carbamoyl, n-butyl(methyl)carbamoyl, n-butyl(ethyl)carbamoyl, n-butyl(i-propyl)carbamoyl, di(sec-butyl)carbamoyl, sec-butyl(methyl)carbamoyl, sec-butyl(ethyl)carbamoyl, sec-butyl(n-propyl)carbamoyl, sec-butyl(i-propyl)carbamoyl, di(t-butyl)carbamoyl, t-butyl(methyl)carbamoyl, t-butyl(ethyl)carbamoyl, t-butyl(n-propyl)carbamoyl, t-butyl(i-propyl)carbamoyl, trifluoromethyl(methyl)carbamoyl, trifluoromethyl(ethyl)carbamoyl, trifluoromethyl(n-propyl)carbamoyl, trifluoromethyl(i-propyl)carbamoyl, trifluoromethyl (n-butyl)carbamoyl, trifluoromethyl(sec-butyl)carbamoyl, difluoromethyl(methyl)carbamoyl, difluoromethyl(ethyl)carbamoyl, difluoromethyl(n-propyl)carbamoyl, difluoromethyl (i-propyl)carbamoyl, difluoromethyl(n-butyl))carbamoyl, difluoromethyl(sec-butyl)carbamoyl, difluoromethyl(t-butyl)carbamoyl, difluoromethyl(trifluoromethyl)carbamoyl, hydroxymethyl(methyl)carbamoyl, ethyl(hydroxymethyl)carbamoyl, hydroxymethyl(n-propyl)carbamoyl, hydroxymethyl(i-propyl)carbamoyl, n-butyl(hydroxymethyl)carbamoyl, sec-butyl(hydroxymethyl)carbamoyl, t-butyl(hydroxymethyl)carbamoyl, difluoromethyl(hydroxymethyl)carbamoyl, hydroxymethyl(trifluoromethyl)carbamoyl, hydroxyethyl (methyl)carbamoyl, ethyl(hydroxyethyl)carbamoyl, hydroxyethyl(n-propyl)carbamoyl, hydroxyethyl(i-propyl) carbamoyl, n-butyl(hydroxyethyl)carbamoyl, sec-butyl(hydroxyethyl)carbamoyl, t-butyl(hydroxyethyl)carbamoyl, difluoromethyl(hydroxyethyl)carbamoyl, hydroxyethyl (trifluoromethyl)carbamoyl, hydroxypropyl(methyl) carbamoyl, ethyl(hydroxypropyl)carbamoyl, hydroxypropyl (n-propyl)carbamoyl, hydroxypropyl(i-propyl)carbamoyl, n-butyl(hydroxypropyl)carbamoyl, sec-butyl(hydroxypropyl)carbamoyl, t-butyl(hydroxypropyl)carbamoyl, difluoromethyl(hydroxypropyl)carbamoyl, hydroxypropyl(trifluoromethyl)carbamoyl.

As used herein, the term alkylsulfinyl embraces radicals containing an optionally substituted, linear or branched alkyl radicals of 1 to 10 carbon atoms attached to a divalent —SO— radical. More preferred alkylsulfinyl radicals are "lower alkylsulfinyl" radicals having 1 to 8, preferably 1 to 6 and more preferably 1 to 4 carbon atoms.

An alkylsulfinyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a alkylsulfinyl group are themselves unsubstituted.

Preferred optionally substituted alkylsulfinyl radicals include methylsulfinyl, ethylsulfinyl, n-propylsulfinyl, i-propylsulfinyl, n-butylsulfinyl, sec-butylsulfinyl, t-butylsulfinyl, trifluoromethylsulfinyl, difluoromethylsulfinyl, hydroxymethylsulfinyl, 2-hydroxyethylsulfinyl and 2-hydroxypropylsulfinyl.

As used herein, the term alkylsulfonyl embraces radicals containing an optionally substituted, linear or branched alkyl radicals of 1 to 10 carbon atoms attached to a divalent —$SO_2$— radical. More preferred alkylsulfonyl radicals are "lower alkylsulfonyl" radicals having 1 to 8, preferably 1 to 6 and more preferably 1 to 4 carbon atoms.

An alkylsulfonyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a monoalkylaminosulfonyl group are themselves unsubstituted.

As used herein, the term monoalkylaminosulfonyl embraces radicals containing an optionally substituted, linear or branched alkyl radicals of 1 to 10 carbon atoms and attached to the nitrogen of a-$NHSO_2$— radical. More preferred monoalkylaminosulfonyl radicals are "lower monoalkylaminosulfonyl" radicals having 1 to 8, preferably 1 to 6 and more preferably 1 to 4 carbon atoms.

A monoalkylaminosulfonyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a monoalkylaminosulfonyl group are themselves unsubstituted.

Preferred optionally substituted monoalkylaminosulfonyl radicals include methylaminosulfonyl, ethylaminosulfonyl, n-propylaminosulfonyl, i-propylaminosulfonyl, n-butylaminosulfonyl, sec-butylaminosulfonyl, t-butylaminosulfonyl, trifluoromethylaminosulfonyl, difluoromethylaminosulfonyl, hydroxymethylaminosulfonyl, 2-hydroxyethylaminosulfonyl and 2-hydroxypropylaminosulfonyl.

As used herein, the term dialkylaminosulfonyl embraces radicals containing a radical $NSO_2$— where the nitrogen is attached to two optionally substituted, linear or branched alkyl radicals of 1 to 10 carbon atoms. More preferred dialkylaminosulfonyl radicals are "lower dialkylaminosulfonyl"

radicals having 1 to 8, preferably 1 to 6 and more preferably 1 to 4 carbon atoms in each alkyl radical.

A dialkylaminosulfonyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a dialkylaminosulfonyl group are themselves unsubstituted.

Preferred optionally substituted dialkylaminosulfonyl radicals include dimethylaminosulfonyl, diethylaminosulfonyl, methyl(ethyl)aminosulfonyl, di (n-propyl)aminosulfonyl, n-propyl(methyl)aminosulfonyl, n-propyl(ethyl)aminosulfonyl, di(i-propyl)aminosulfonyl, i-propyl(methyl)aminosulfonyl, i-propyl(ethyl)aminosulfonyl, di(n-butyl)aminosulfonyl, n-butyl(methyl)aminosulfonyl, n-butyl(ethyl)aminosulfonyl, n-butyl(i-propyl)aminosulfonyl, di(sec-butyl)aminosulfonyl, sec-butyl(methyl)aminosulfonyl, sec-butyl(ethyl)aminosulfonyl, sec-butyl(n-propyl)aminosulfonyl, sec-butyl(i-propyl)aminosulfonyl, di(t-butyl)aminosulfonyl, t-butyl(methyl)aminosulfonyl, t-butyl(ethyl)aminosulfonyl, t-butyl(n-propyl)aminosulfonyl, t-butyl(i-propyl)aminosulfonyl, trifluoromethyl(methyl)aminosulfonyl, trifluoromethyl(ethyl)aminosulfonyl, trifluoromethyl (n-propyl)aminosulfonyl, trifluoromethyl(i-propyl)aminosulfonyl, trifluoromethyl(n-butyl)aminosulfonyl, trifluoromethyl(sec-butyl)aminosulfonyl, difluoromethyl(methyl)aminosulfonyl, difluoromethyl(ethyl)aminosulfonyl, difluoromethyl (n-propyl)aminosulfonyl, difluoromethyl(i-propyl)aminosulfonyl, difluoromethyl(n-butyl))aminosulfonyl, difluoromethyl(sec-butyl)aminosulfonyl, difluoromethyl(t-butyl)aminosulfonyl, difluoromethyl (trifluoromethyl)aminosulfonyl, hydroxymethyl(methyl)aminosulfonyl, ethyl(hydroxymethyl)aminosulfonyl, hydroxymethyl(n-propyl)aminosulfonyl, hydroxymethyl(i-propyl)aminosulfonyl, n-butyl(hydroxymethyl)aminosulfonyl, sec-butyl(hydroxymethyl)aminosulfonyl, t-butyl(hydroxymethyl)aminosulfonyl, difluoromethyl (hydroxymethyl)aminosulfonyl, hydroxymethyl (trifluoromethyl)aminosulfonyl, hydroxyethyl(methyl)aminosulfonyl, ethyl(hydroxyethyl)aminosulfonyl, hydroxyethyl(n-propyl)aminosulfonyl, hydroxyethyl (i-propyl)aminosulfonyl, n-butyl(hydroxyethyl)aminosulfonyl, sec-butyl(hydroxyethyl)aminosulfonyl, t-butyl(hydroxyethyl)aminosulfonyl, difluoromethyl(hydroxyethyl)aminosulfonyl, hydroxyethyl(trifluoromethyl)aminosulfonyl, hydroxypropyl(methyl)aminosulfonyl, ethyl(hydroxypropyl)aminosulfonyl, hydroxypropyl (n-propyl)aminosulfonyl, hydroxypropyl(i-propyl)aminosulfonyl, n-butyl(hydroxypropyl)aminosulfonyl, sec-butyl(hydroxypropyl)aminosulfonyl, t-butyl(hydroxypropyl)aminosulfonyl, difluoromethyl (hydroxypropyl)aminosulfonyl and hydroxypropyl (trifluoromethyl)aminosulfonyl.

As used herein, the term alkylsulfamoyl embraces radicals containing an optionally substituted, linear or branched alkyl radical of 1 to 10 carbon atoms and attached to the nitrogen of a -NSO$_2$— radical. More preferred alkylsulfamoyl radicals are "lower alkylsulfamoyl" radicals having 1 to 8, preferably 1 to 6 and more preferably 1 to 4 carbon atoms.

An alkylsulfamoyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkylsulfamoyl group are themselves unsubstituted.

Preferred optionally substituted alkylsulfamoyl radicals include methylsulfamoyl, ethylsulfamoyl, n-propylsulfamoyl, i-propylsulfamoyl, n-butylsulfamoyl, sec-butylsulfamoyl, t-butylsulfamoyl, trifluoromethylsulfamoyl, difluoromethylsulfamoyl, hydroxymethylsulfamoyl, 2-hydroxyethylsulfamoyl and 2-hydroxypropylsulfamoyl.

As used herein, the term alkylsulfamido embraces radicals containing an optionally substituted, linear or branched alkyl radicals of 1 to 10 carbon atoms and attached to one of the nitrogen atoms of a —NHSO$_2$NH— radical. More preferred alkylsulfamido radicals are "lower alkylsulfamido" radicals having 1 to 8, preferably 1 to 6 and more preferably 1 to 4 carbon atoms.

An alkylsulfamido group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an alkylsulfamido group are themselves unsubstituted.

Preferred optionally substituted alkylsulfamido radicals include methylsulfamido, ethylsulfamido, n-propylsulfamido, i-propylsulfamido, n-butylsulfamido, sec-butylsulfamido, t-butylsulfamido, trifluoromethylsulfamido, difluoromethylsulfamido, hydroxymethylsulfamido, 2-hydroxyethylsulfamido and 2-hydroxysulfamido.

As used herein, the term N'-alkylureido embraces radicals containing an optionally substituted, linear or branched alkyl radical of 1 to 10 carbon atoms attached to the terminal nitrogen of a —NHCONH— radical. More preferred N'-alkylureido radicals are "lower N'-alkylureido" radicals in which the alkyl moiety has 1 to 8, preferably 1 to 6 and more preferably 1 to 4 carbon atoms.

An N'-alkylureido group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an N'-alkylureido group are themselves unsubstituted.

Preferred optionally substituted N'-alkylureido radicals include N'-methylureido, N'-ethylureido, N'-n-propylureido, N'-i-propylureido, N'-n-butylureido, N'-sec-butylureido, N'-t-butylureido, N'-trifluoromethylureido, N'-difluoromethylureido, N'-hydroxymethylureido, N'-2-hydroxyethylureido and N'-2-hydroxypropylureido.

As used herein, the term N',N'-dialkylureido embraces radicals containing a radical —NHCON where the terminal nitrogen is attached to two optionally substituted, linear or branched alkyl radicals of 1 to 10 carbon atoms. More preferred N',N'-dialkylureido radicals are "lower N',N'-dialkylureido" radicals having 1 to 8, preferably 1 to 6 and more preferably 1 to 4 carbon atoms in each alkyl radical.

A N',N'-dialkylureido group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an N',N'-dialkylureido group are themselves unsubstituted.

Preferred optionally substituted N',N'-dialkylureido radicals include N',N'-dimethylureido, N',N'-diethylureido, N'-methyl, N'-ethylureido, N',N'-di (n-propyl)ureido, N'-n-propyl, N'-methylureido, N'-n-propyl, N'-ethylureido, N',N'-di(i-propyl)ureido, N'-i-propyl, N'-methylureido, N'-i-propyl, N'-ethylureido, N',N'-di(n-butyl)ureido, N'-n-butyl, N'-methylureido, N'-n-butyl, N'-ethylureido, N'-n-butyl, N'-

(i-propyl)ureido, N',N'-di(sec-butyl)ureido, N'-sec-butyl, N'-methylureido, N'-sec-butyl, N'-ethylureido, N'-sec-butyl, N'-(n-propyl)ureido, N'-sec-butyl, N'(i-propyl)ureido, N',N'-di(t-butyl)ureido, N'-t-butyl, N'-methylureido, N'-t-butyl, N'-ethylureido, N'-t-butyl, N'-(n-propyl)ureido, N'-t-butyl, N'-(i-propyl)ureido, N'-trifluoromethyl, N'-methylureido, N'-trifluoromethyl, N'-ethylureido, N'-trifluoromethyl, N'-(n-propyl)ureido, N'-trifluoromethyl, N'-(i-propyl)ureido, N'-trifluoromethyl, N'-(n-butyl)ureido, N'-trifluoromethyl, N'-(sec-butyl)ureido, N'-difluoromethyl, N'-methylureido, N'-difluoromethyl, N'-ethylureido, N'-difluoromethyl, N'-(n-propyl)ureido, N'-difluoromethyl, N'-(i-propyl)ureido, N'-difluoromethyl, N'-(n-butyl)ureido, N'-difluoromethyl, N'-(sec-butyl)ureido, N'-difluoromethyl, N'-(t-butyl)ureido, N'-difluoromethyl, N'-trifluoromethylureido, N'-hydroxymethyl, N'-methylureido, N'-ethyl, N'-hydroxymethylureido, N'-hydroxymethyl, N'-(n-propyl)ureido, N'-hydroxymethyl, N'-(i-propyl)ureido, N'-n-butyl, N'-hydroxymethylureido, N'-sec-butyl, N'-hydroxymethylureido, N'-t-butyl, N'-hydroxymethylureido, N'-difluoromethyl, N'-hydroxymethylureido, N'hydroxymethyl, N'-trifluoromethylureido, N'-hydroxyethyl, N'-methylureido, N'-ethyl, N'-hydroxyethylureido, N'-hydroxyethyl, N'-(n-propyl)ureido, N'-hydroxyethyl, N'-(i-propyl)ureido, N'-(n-butyl), N'-hydroxyethylureido, N'(sec-butyl), N'-hydroxyethylureido, N'-(t-butyl), N'-hydroxyethylureido, N'-difluoromethyl, N'-hydroxyethylureido, N'-hydroxyethyl, N'-trifluoromethylureido, N'-hydroxypropyl, N'-methylureido, N'-ethyl, N'-hydroxypropylureido, N'-hydroxypropyl, N'-(n-propyl)ureido, N'-hydroxypropyl, N'-(i-propyl)ureido, N'-(n-butyl), N'-hydroxypropylureido, N'(sec-butyl), N'-hydroxypropylureido, N'(t-butyl), N'-hydroxypropylureido, N'-difluoromethyl, N'-hydroxypropylureido y N'-hydroxypropyl, N'-trifluoromethylureido.

As used herein, the term acyl embraces optionally substituted, linear or branched radicals having 2 to 20 carbon atoms or, preferably 2 to 12 carbon atoms attached to a carbonyl radical. More preferably acyl radicals are "lower acyl" radicals of formula —COR, wherein R is a hydrocarbon group, preferably an alkyl group, having 2 to 8, preferably 2 to 6 and more preferably 2 to 4 carbon atoms.

An acyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on an acyl group are themselves unsubstituted.

Preferred optionally substituted acyl radicals include acetyl, propionyl, butyryl, isobutyryl, isovaleryl, pivaloyl, valeryl, lauryl, myristyl, stearyl and palmityl, As used herein, the term aryl radical embraces typically a $C_5$-$C_{14}$ monocyclic or polycyclic aryl radical such as phenyl, naphthyl, anthranyl and phenanthryl. Phenyl is preferred.

A said optionally substituted aryl radical is typically unsubstituted or substituted with 1, 2 or 3 substituents which may be the same or different. The substituents are preferably selected from halogen atoms, preferably fluorine atoms, hydroxy groups, alkoxycarbonyl groups in which the alkyl moiety has from 1 to 4 carbon atoms, hydroxycarbonyl groups, carbamoyl groups, nitro groups, cyano groups, $C_1$-$C_4$ alkyl groups, $C_1$-$C_4$ alkoxy groups and $C_1$-$C_4$ hydroxyalkyl groups. When an aryl radical carries 2 or more substituents, the substituents may be the same or different. Unless otherwise specified, the substituents on an aryl group are typically themselves unsubstituted.

As used herein, the term heteroaryl radical embraces typically a 5- to 14-membered ring system, preferably a 5- to 10-membered ring system, comprising at least one heteroaromatic ring and containing at least one heteroatom selected from O, S and N. A heteroaryl radical may be a single ring or two or more fused rings wherein at least one ring contains a heteroatom.

A said optionally substituted heteroaryl radical is typically unsubstituted or substituted with 1, 2 or 3 substituents which may be the same or different. The substituents are preferably selected from halogen atoms, preferably fluorine, chlorine or bromine atoms, alkoxycarbonyl groups in which the alkyl moiety has from 1 to 4 carbon atoms, nitro groups, hydroxy groups, $C_1$-$C_4$ alkyl groups and $C_1$-$C_4$ alkoxy groups. When an heteroaryl radical carries 2 or more substituents, the substituents may be the same or different. Unless otherwise specified, the substituents on a heteroaryl radical are typically themselves unsubstituted.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidinyl and the various pyrrolopyridyl radicals.

Oxadiazolyl, oxazolyl, pyridyl, pyrrolyl, imidazolyl, thiazolyl, thiadiazolyl, thienyl, furanyl, quinolinyl, isoquinolinyl, indolyl, benzoxazolyl, naphthyridinyl, benzofuranyl, pyrazinyl, pyrimidinyl and the various pyrrolopyridyl radicals are preferred.

As used herein, the term cycloalkyl embraces saturated carbocyclic radicals and, unless otherwise specified, a cycloalkyl radical typically has from 3 to 7 carbon atoms.

A cycloalkyl radical is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. When a cycloalkyl radical carries 2 or more substituents, the substituents may be the same or different. Typically the substituents on a cycloalkyl group are themselves unsubstituted. The cycloalkyl radicals of the present invention also comprise monocyclic $C_{3-7}$ carbon rings fused with a phenyl ring.

Examples include cyclopropyl, cyclobutyl, cyclopentyl, cyclohexyl and cycloheptyl, tetrahydrobenzanulene, tetrahydronapthtyl, bicyclo[4.2.0]octa-1,3,5-triene and indanyl. It is preferably cyclopropyl, cyclopentyl, indanyl and cyclohexyl.

As used herein, the term cycloalkenyl embraces partially unsaturated carbocyclic radicals and, unless otherwise specified, a cycloalkenyl radical typically has from 3 to 7 carbon atoms.

A cycloalkenyl radical is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. When a cycloalkenyl radical carries 2 or more substituents, the substituents may be the same or different. Typically, the substituents on a cycloalkenyl group are themselves unsubstituted.

Examples include cyclobutenyl, cyclopentenyl, cyclohexenyl and cycloheptenyl. Cyclopentenyl and cyclohexenyl are preferred.

As used herein, the term heterocyclyl radical embraces typically a non-aromatic, saturated or unsaturated $C_3$-$C_{10}$ carbocyclic ring system, such as a 5, 6 or 7 membered radical, in which one or more, for example 1, 2, 3 or 4 of the carbon atoms preferably 1 or 2 of the carbon atoms are replaced by a heteroatom selected from N, O and S. Saturated heterocyclyl radicals are preferred. A heterocyclic radical may be a single ring or two or more fused rings wherein at least one ring contains a heteroatom. When a heterocyclyl radical carries 2 or more substituents, the substituents may be the same or different.

A said optionally substituted heterocyclyl radical is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, the substituents on a heterocyclyl radical are themselves unsubstituted.

Examples of heterocyclic radicals include piperidyl, pyrrolidyl, pyrrolinyl, piperazinyl, morpholinyl, thiomorpholinyl, pyrrolyl, pyrazolinyl, pyrazolidinyl, quinuclidinyl, triazolyl, pyrazolyl, tetrazolyl, chromanyl, isochromanyl, imidazolidinyl, imidazolyl, oxiranyl, aziridinyl, 4,5-dihydro-oxazolyl, 2-benzofuran-1(3H)-one, 1,3-dioxol-2-one and 3-aza-tetrahydrofuranyl.

Where a heterocyclyl radical carries 2 or more substituents, the substituents may be the same or different.

As used herein, some of the atoms, radicals, moieties, chains and cycles present in the general structures of the invention are "optionally substituted". This means that these atoms, radicals, moieties, chains and cycles can be either unsubstituted or substituted in any position by one or more, for example 1, 2, 3 or 4, substituents, whereby the hydrogen atoms bound to the unsubstituted atoms, radicals, moieties, chains and cycles are replaced by chemically acceptable atoms, radicals, moieties, chains and cycles. When two or more substituents are present, each substituent may be the same or different. The substituents are typically themselves unsubstituted.

Typically when a cyclic radical is bridged by an alkylene or alkylenedioxy radical, the bridging alkylene radical is attached to the ring at non-adjacent atoms.

As used herein, the term halogen atom embraces chlorine, fluorine, bromine and iodine atoms. A halogen atom is typically a fluorine, chlorine or bromine atom, most preferably chlorine or fluorine. The term halo when used as a prefix has the same meaning.

As used herein, an acylamino group is typically a said acyl group attached to an amino group.

As used herein an alkylenedioxy group is typically —O—R—O—, wherein R is a said alkylene group.

As used herein, an alkoxycarbonyl group is typically a said alkoxy group attached to a said carbonyl group.

As used herein, an acyloxy group is typically a said acyl group attached to an oxygen atom.

As used herein, a cycloalkoxy group is typically a said cycloalkyl group attached to an oxygen atom.

Compounds containing one or more chiral centre may be used in enantiomerically or diastereoisomerically pure form, or in the form of a mixture of isomers.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

As used herein, an N-oxide is formed from the tertiary basic amines or imines present in the molecule, using a convenient oxidising agent.

According to one embodiment of the present invention in the compounds of formula (I) $R^1$ is selected from the group consisting of hydrogen atoms and lower alkyl groups, which are optionally substituted by one or more substituents selected from halogen atoms and hydroxy, alkoxy, alkylthio, hydroxycarbonyl and alkoxycarbonyl groups.

According to another embodiment of the present invention in the compounds of formula (I) $R^2$ is an heteroaryl group which is optionally substituted by one or more substituents selected from halogen atoms and alkyl, hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups.

According to another embodiment of the present invention in the compounds of formula (I) $R^2$ is a N-containing heteroaryl group. It is also preferred that $R^2$ is optionally substituted by one or more substituents selected from halogen atoms and lower alkyl groups According to still another embodiment of the present invention in the compounds of formula (I) $R^4$ represents:

$$G-L1-(CRR')_n-$$

wherein n is an integer from 1 to 3

R and R' are independently selected from the group consisting of hydrogen atoms and lower alkyl groups L1 is a linker selected from the group consisting of a direct bond, —O—, —O(CO)—, —(CO)O— and —O(CO)O— groups G is selected from alkyl, cycloalkyl, heterocyclyl, aryl and heteroaryl groups said groups being optionally substituted with one or more substituents selected from:
halogen atoms;
alkyl and alkenyl groups, which are optionally substituted by one or more substituents selected from halogen atoms; and
hydroxy, alkoxy, cyano and cycloalkyloxy groups, It is particularly advantageous that when n is zero, L1 is a direct bond and G is different from a hydrogen atom.

It is still a further preferred embodiment of the present invention that in the compounds of formula (I) $R^4$ represents:

$$G-L1-(CRR')_n-$$

wherein n is an integer from 1 to 3

R and R' are independently selected from the group consisting of hydrogen atoms and lower alkyl groups L1 is a linker selected from the group consisting of a direct bond, —O—, —O(CO)— and —O(CO)O— groups G is selected from alkyl, cycloalkyl, heterocyclyl, aryl and heteroaryl groups said groups being optionally substituted with one or more substituents selected from:
halogen atoms;
alkyl and alkenyl groups, which are optionally substituted by one or more substituents selected from halogen atoms; and
hydroxy, alkoxy and cycloalkyloxy groups, According to still another embodiment of the present invention in the compounds of formula (I) R⁴ represents:

G-L1-(CRR')ₙ— wherein
n is an integer from 1 to 2
R and R' are independently selected from the group consisting of hydrogen atoms and methyl groups
L1 is selected from direct bond and groups —O—, —(CO)O— and —O(CO)O—; and
G is selected from alkyl, cycloalkyl, aryl and heteroaryl groups said groups being optionally substituted with one or more halogen atoms or groups alkoxy, cyano, alkyl or —CF₃;

It is still a further preferred embodiment of the present invention that in the compounds of formula (I) R⁴ represents:

G-L1-(CRR')ₙ— wherein
n is an integer from 1 to 2
R and R' are independently selected from the group consisting of hydrogen atoms and methyl groups
L1 is a direct bond; and
G is selected from alkyl, cycloalkyl, aryl and heteroaryl groups said groups being optionally substituted with one or more halogen atoms;

According to another embodiment of the present invention in the compounds of formula (I) R³ represents a hydrogen atom or an acyl group Particular individual compounds of the invention include:
ethyl 4-acetyl-1-ethyl-6-oxo-5-(quinolin-5-ylamino)-1,6-dihydropyridazine-3-carboxylate
ethyl 4-acetyl-1-ethyl-6-oxo-5-(pyridin-3-ylamino)-1,6-dihydropyridazine-3-carboxylate
ethyl 4-acetyl-1-ethyl-5-(isoquinolin-4-ylamino)-6-oxo-1,6-dihydropyridazine-3-carboxylate
ethyl 4-acetyl-1-ethyl-5-[(4-methylpyridin-3-yl)amino]-6-oxo-1,6-dihydropyridazine-3-carboxylate
isopropyl 4-acetyl-1-ethyl-6-oxo-5-(pyridin-3-ylamino)-1,6-dihydropyridazine-3-carboxylate
benzyl 4-acetyl-1-ethyl-6-oxo-5-(pyridin-3-ylamino)-1,6-dihydropyridazine-3-carboxylate
isopropyl 4-acetyl-1-ethyl-5-(isoquinolin-4-ylamino)-6-oxo-1,6-dihydropyridazine-3-carboxylate
3-methylbutyl 4-acetyl-1-ethyl-6-oxo-5-(pyridin-3-ylamino)-1,6-dihydropyridazine-3-carboxylate
2-methoxyethyl 4-acetyl-1-ethyl-6-oxo-5-(pyridin-3-ylamino)-1,6-dihydropyridazine-3-carboxylate
cyclopropylmethyl 4-acetyl-1-ethyl-6-oxo-5-(pyridin-3-ylamino)-1,6-dihydropyridazine-3-carboxylate
methyl 4-acetyl-1-ethyl-6-oxo-5-(pyridin-3-ylamino)-1,6-dihydropyridazine-3-carboxylate
2-phenylethyl 4-acetyl-1-ethyl-6-oxo-5-(pyridin-3-ylamino)-1,6-dihydropyridazine-3-carboxylate
benzyl 4-acetyl-1-ethyl-5-(isoquinolin-4-ylamino)-6-oxo-1,6-dihydropyridazine-3-carboxylate
cyclohexyl 4-acetyl-1-ethyl-5-(isoquinolin-4-ylamino)-6-oxo-1,6-dihydropyridazine-3-carboxylate
tert-butyl 4-acetyl-1-ethyl-5-(isoquinolin-4-ylamino)-6-oxo-1,6-dihydropyridazine-3-carboxylate
cyclobutyl 4-acetyl-1-ethyl-5-(isoquinolin-4-ylamino)-6-oxo-1,6-dihydropyridazine-3-carboxylate
cyclohexyl 4-acetyl-1-ethyl-5-[(4-methylpyridin-3-yl)amino]-6-oxo-1,6-dihydropyridazine-3-carboxylate
1-methyl-2-phenylethyl 4-acetyl-1-ethyl-5-(isoquinolin-4-ylamino)-6-oxo-1,6-dihydropyridazine-3-carboxylate
1-phenylethyl 4-acetyl-1-ethyl-5-(isoquinolin-4-ylamino)-6-oxo-1,6-dihydropyridazine-3-carboxylate
tert-butyl 4-acetyl-1-ethyl-5-[(4-methylpyridin-3-yl)amino]-6-oxo-1,6-dihydropyridazine-3-carboxylate
1-phenylethyl 4-acetyl-1-ethyl-5-[(4-methylpyridin-3-yl)amino]-6-oxo-1,6-dihydropyridazine-3-carboxylate
sec-butyl 4-acetyl-1-ethyl-5-(isoquinolin-4-ylamino)-6-oxo-1,6-dihydropyridazine-3-carboxylate
2-(dimethylamino)-2-oxoethyl 4-acetyl-1-ethyl-5-(isoquinolin-4-ylamino)-6-oxo-1,6-dihydropyridazine-3-carboxylate
2-methoxy-1-methyl-2-oxoethyl 4-acetyl-1-ethyl-5-(isoquinolin-4-ylamino)-6-oxo-1,6-dihydropyridazine-3-carboxylate
benzyl 1-ethyl-5-[(4-methylpyridin-3-yl)amino]-6-oxo-1,6-dihydropyridazine-3-carboxylate
ethyl 1-ethyl-6-oxo-5-(pyridin-3-ylamino)-1,6-dihydropyridazine-3-carboxylate
ethyl 1-ethyl-5-[(4-methylpyridin-3-yl)amino]-6-oxo-1,6-dihydropyridazine-3-carboxylate
isopropyl 1-ethyl-6-oxo-5-(pyridin-3-ylamino)-1,6-dihydropyridazine-3-carboxylate
pyridin-2-ylmethyl 1-ethyl-6-oxo-5-(pyridin-3-ylamino)-1,6-dihydropyridazine-3-carboxylate
isopropyl 1-ethyl-5-[(4-methylpyridin-3-yl)amino]-6-oxo-1,6-dihydropyridazine-3-carboxylate
ethyl 1-ethyl-5-(isoquinolin-4-ylamino)-6-oxo-1,6-dihydropyridazine-3-carboxylate
isopropyl 1-ethyl-5-(isoquinolin-4-ylamino)-6-oxo-1,6-dihydropyridazine-3-carboxylate
3-thienylmethyl 1-ethyl-5-(isoquinolin-4-ylamino)-6-oxo-1,6-dihydropyridazine-3-carboxylate
3-thienylmethyl 1-ethyl-5-[(4-methylpyridin-3-yl)amino]-6-oxo-1,6-dihydropyridazine-3-carboxylate
3-methoxybenzyl 1-ethyl-5-(isoquinolin-4-ylamino)-6-oxo-1,6-dihydropyridazine-3-carboxylate
3-methoxybenzyl 1-ethyl-5-[(4-methylpyridin-3-yl)amino]-6-oxo-1,6-dihydropyridazine-3-carboxylate
3-chlorobenzyl 1-ethyl-5-(isoquinolin-4-ylamino)-6-oxo-1,6-dihydropyridazine-3-carboxylate
1-phenylethyl 1-ethyl-5-(isoquinolin-4-ylamino)-6-oxo-1,6-dihydropyridazine-3-carboxylate
1-phenylethyl 1-ethyl-5-[(4-methylpyridin-3-yl)amino]-6-oxo-1,6-dihydropyridazine-3-carboxylate
1-pyridin-4-ylethyl 1-ethyl-5-(isoquinolin-4-ylamino)-6-oxo-1,6-dihydropyridazine-3-carboxylate
1-pyridin-4-ylethyl 1-ethyl-5-[(4-methylpyridin-3-yl)amino]-6-oxo-1,6-dihydropyridazine-3-carboxylate
1-pyridin-4-ylethyl 1-ethyl-6-oxo-5-(pyridin-3-ylamino)-1,6-dihydropyridazine-3-carboxylate
2,3-dihydro-1H-inden-1-yl 1-ethyl-5-(isoquinolin-4-ylamino)-6-oxo-1,6-dihydropyridazine-3-carboxylate
2,3-dihydro-1H-inden-1-yl 1-ethyl-5-[(4-methylpyridin-3-yl)amino]-6-oxo-1,6-dihydropyridazine-3-carboxylate
1,3,3-Trimethylbutyl 4-acetyl-1-ethyl-5-(isoquinolin-4-ylamino)-6-oxo-1,6-dihydropyridazine-3-carboxylate
3-Chlorobenzyl 4-acetyl-1-ethyl-5-(isoquinolin-4-ylamino)-6-oxo-1,6-dihydropyridazine-3-carboxylate
3-Methoxybenzyl 4-acetyl-1-ethyl-5-(isoquinolin-4-ylamino)-6-oxo-1,6-dihydropyridazine-3-carboxylate
Benzyl 1-ethyl-5-(isoquinolin-4-ylamino)-6-oxo-1,6-dihydropyridazine-3-carboxylate
Octyl 4-acetyl-1-ethyl-5-(isoquinolin-4-ylamino)-6-oxo-1,6-dihydropyridazine-3-carboxylate
1,5-Dimethylhex-4-en-1-yl 4-acetyl-1-ethyl-5-(isoquinolin-4-ylamino)-6-oxo-1,6-dihydropyridazine-3-carboxylate Allyl 4-acetyl-1-ethyl-5-(isoquinolin-4-ylamino)-6-oxo-1,6-dihydropyridazine-3-carboxylate
Benzyloxycarbonylmethyl 1-ethyl-5-(isoquinolin-4-ylamino)-6-oxo-1,6-dihydropyridazine-3-carboxylate
2-Oxo-2-phenylethyl 1-ethyl-5-(isoquinolin-4-ylamino)-6-oxo-1,6-dihydropyridazine-3-carboxylate
Dimethylcarbamoylmethyl 1-ethyl-5-(isoquinolin-4-ylamino)-6-oxo-1,6-dihydropyridazine-3-carboxylate
2-Phenoxyethyl 1-ethyl-5-(isoquinolin-4-ylamino)-6-oxo-1,6-dihydropyridazine-3-carboxylate
2-Dimethylaminoethyl 1-ethyl-5-(isoquinolin-4-ylamino)-6-oxo-1,6-dihydropyridazine-3-carboxylate
4-Bromobenzyl 1-ethyl-5-(isoquinolin-4-ylamino)-6-oxo-1,6-dihydropyridazine-3-carboxylate
4-Bromobenzyl 1-ethyl-5-(4-methyl-pyridin-3-ylamino)-6-oxo-1,6-dihydropyridazine-3-carboxylate
4-Bromobenzyl 1-ethyl-6-oxo-5-(pyridin-3-ylamino)-1,6-dihydropyridazine-3-carboxylate
2-Chlorobenzyl 1-ethyl-5-(isoquinolin-4-ylamino)-6-oxo-1,6-dihydropyridazine-3-carboxylate
2-Chlorobenzyl 1-ethyl-5-(4-methyl-pyridin-3-ylamino)-6-oxo-1,6-dihydropyridazine-3-carboxylate
3-Methylbenzyl 1-ethyl-5-(isoquinolin-4-ylamino)-6-oxo-1,6-dihydropyridazine-3-carboxylate
3-Trifluoromethylbenzyl 1-ethyl-5-(isoquinolin-4-ylamino)-6-oxo-1,6-dihydropyridazine-3-carboxylate
3-Trifluoromethylbenzyl 1-ethyl-5-(4-methyl-pyridin-3-ylamino) 6-oxo-1,6-dihydropyridazine-3-carboxylate
3-Trifluoromethylbenzyl 1-ethyl-6-oxo-5-(pyridin-3-ylamino)-1,6-dihydropyridazine-3-carboxylate
2-(Benzylmethylamino)-ethyl 1-ethyl-5-(isoquinolin-4-ylamino)-6-oxo-1,6-dihydropyridazine-3-carboxylate
4-Methoxybenzyl 1-ethyl-5-(isoquinolin-4-ylamino)-6-oxo-1,6-dihydropyridazine-3-carboxylate
3-Cyanobenzyl 1-ethyl-5-(4-methyl-pyridin-3-ylamino)-6-oxo-1,6-dihydropyridazine-3-carboxylate
3-Cyanobenzyl 1-ethyl-5-(isoquinolin-4-ylamino)-6-oxo-1,6-dihydropyridazine-3-carboxylate
Cyclohexyloxycarbonyloxymethyl 1-ethyl-5-(isoquinolin-4-ylamino)-6-oxo-1,6-dihydropyridazine-3-carboxylate
1-Cyclohexyloxycarbonyloxyethyl 1-ethyl-5-(isoquinolin-4-ylamino)-6-oxo-1,6-dihydropyridazine-3-carboxylate
2,2-Dimethylbutyryloxymethyl 1-ethyl-5-(isoquinolin-4-ylamino)-6-oxo-1,6-dihydropyridazine-3-carboxylate
(S)-2-Amino-4-methylpentanoyloxymethyl 1-ethyl-5-(isoquinolin-4-ylamino)-6-oxo-1,6-dihydropyridazine-3-carboxylate
and pharmaceutically acceptable salts thereof.
Of outstanding interest are:
benzyl 1-ethyl-5-[(4-methylpyridin-3-yl)amino]-6-oxo-1,6-dihydropyridazine-3-carboxylate
pyridin-2-ylmethyl 1-ethyl-6-oxo-5-(pyridin-3-ylamino)-1,6-dihydropyridazine-3-carboxylate
ethyl 1-ethyl-5-(isoquinolin-4-ylamino)-6-oxo-1,6-dihydropyridazine-3-carboxylate
3-thienylmethyl 1-ethyl-5-[(4-methylpyridin-3-yl)amino]-6-oxo-1,6-dihydropyridazine-3-carboxylate
3-methoxybenzyl 1-ethyl-5-(isoquinolin-4-ylamino)-6-oxo-1,6-dihydropyridazine-3-carboxylate
3-chlorobenzyl 1-ethyl-5-(isoquinolin-4-ylamino)-6-oxo-1,6-dihydropyridazine-3-carboxylate
1-phenylethyl 1-ethyl-5-(isoquinolin-4-ylamino)-6-oxo-1,6-dihydropyridazine-3-carboxylate
2,3-dihydro-1H-inden-1-yl 1-ethyl-5-(isoquinolin-4-ylamino)-6-oxo-1,6-dihydropyridazine-3-carboxylate
ethyl 4-acetyl-1-ethyl-5-(isoquinolin-4-ylamino)-6-oxo-1,6-dihydropyridazine-3-carboxylate
benzyl 4-acetyl-1-ethyl-6-oxo-5-(pyridin-3-ylamino)-1,6-dihydropyridazine-3-carboxylate
isopropyl 4-acetyl-1-ethyl-5-(isoquinolin-4-ylamino)-6-oxo-1,6-dihydropyridazine-3-carboxylate
benzyl 4-acetyl-1-ethyl-5-(isoquinolin-4-ylamino)-6-oxo-1,6-dihydropyridazine-3-carboxylate
cyclobutyl 4-acetyl-1-ethyl-5-(isoquinolin-4-ylamino)-6-oxo-1,6-dihydropyridazine-3-carboxylate
1-methyl-2-phenylethyl 4-acetyl-1-ethyl-5-(isoquinolin-4-ylamino)-6-oxo-1,6-dihydropyridazine-3-carboxylate
1-phenylethyl 4-acetyl-1-ethyl-5-(isoquinolin-4-ylamino)-6-oxo-1,6-dihydropyridazine-3-carboxylate
1-phenylethyl 4-acetyl-1-ethyl-5-[(4-methylpyridin-3-yl)amino]-6-oxo-1,6-dihydropyridazine-3-carboxylate
2-Phenoxyethyl 1-ethyl-5-(isoquinolin-4-ylamino)-6-oxo-1,6-dihydropyridazine-3-carboxylate
4-Bromobenzyl 1-ethyl-5-(isoquinolin-4-ylamino)-6-oxo-1,6-dihydropyridazine-3-carboxylate
3-Methylbenzyl 1-ethyl-5-(isoquinolin-4-ylamino)-6-oxo-1,6-dihydropyridazine-3-carboxylate
4-Methoxybenzyl 1-ethyl-5-(isoquinolin-4-ylamino)-6-oxo-1,6-dihydropyridazine-3-carboxylate
3-Cyanobenzyl 1-ethyl-5-(isoquinolin-4-ylamino)-6-oxo-1,6-dihydropyridazine-3-carboxylate
Cyclohexyloxycarbonyloxymethyl 1-ethyl-5-(isoquinolin-4-ylamino)-6-oxo-1,6-dihydropyridazine-3-carboxylate
2,2-Dimethylbutyryloxymethyl 1-ethyl-5-(isoquinolin-4-ylamino)-6-oxo-1,6-dihydropyridazine-3-carboxylate
and pharmaceutically acceptable salts thereof.

According to another embodiment the present invention covers pharmaceutical compositions comprising one or more of the compounds of formula (I), as hereinabove described, in admixture with pharmaceutically acceptable diluents or carriers.

In still another embodiment the present invention covers a combination product comprising (i) a compound of formula (I), as hereinabove described, and (ii) another compound selected from (a) steroids, (b) immunosuppressive agents, (c) T-cell receptor blockers, (d) antiinflammatory drugs, (e) β2-adrenergic agonists and (e antagonists of M3 muscarinic receptors; for simultaneous, separate or sequential use in the treatment of the human or animal body.

According to still another embodiment of the present invention is directed to the use of a compound of formula (I), as hereinabove described, in the manufacture of a medicament for the treatment or prevention of a pathological condition or disease susceptible to amelioration by inhibition of phosphodiesterase 4. It is a preferred embodiment to use the compound of formula (I) in the manufacture of a medicament for use in the treatment or prevention of a disorder which is asthma, chronic obstructive pulmonary disease, rheumatoid arthritis, atopic dermatitis, psoriasis or irritable bowel disease.

According to still another embodiment the present invention covers a method for treating a subject afflicted with a pathological condition or disease susceptible to amelioration by inhibition of phosphodiesterase 4, which method comprises administering to the said subject an effective amount of a compound of formula (I), as hereinabove described. In a preferred embodiment the method is used for treating a subject afflicted with a pathological condition or disease which is asthma, chronic obstructive pulmonary disease, rheumatoid arthritis, atopic dermatitis, psoriasis or irritable bowel disease.

The compounds of the present invention may be prepared by one of the processes described below.

Compounds (I) may be obtained as shown in Scheme 1.

Scheme 1

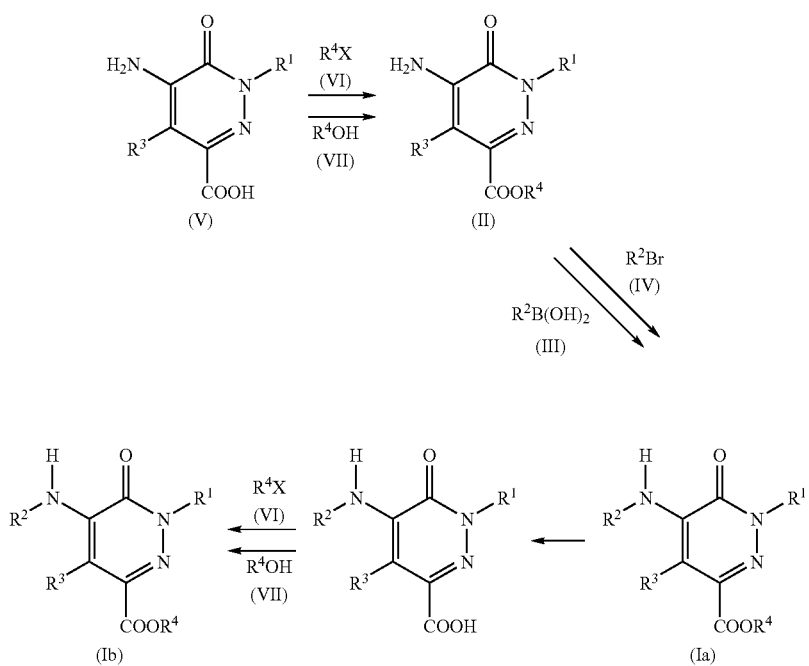

4-Aminopyridazin-3(2H)-one derivatives of formula (V), wherein $R^1$ and $R^3$ are as hereinbefore defined, are reacted with an alkylating agent of formula (VI), wherein $R^4$ is as hereinbefore defined and X is a leaving group such as a chlorine or a bromine atom, in an aprotic solvent in the presence of a base by methods known per se, e.g. D. A. White. *Synthetic Communications,* 1977, 7(8), 559-568, to give compounds of formula (II), wherein $R^1$, $R^3$ and $R^4$ are as hereinbefore defined.

Alternatively, 4-aminopyridazin-3(2H)-one derivatives of formula (V), wherein $R^1$ and $R^3$ are as hereinbefore defined, are condensed with an alcohol of formula (VII) wherein $R^4$ is as hereinbefore described in the presence of triphenylphosphine and diethyl azodicarboxylate by methods known per se, e.g. O. Mitsunobu. *Synthesis,* 1981, 1, 1-28, to give compounds of formula (II), wherein $R^1$, $R^3$ and $R^4$ are as hereinbefore defined.

Condensation of 4-aminopyridazin-3(2H)-one derivatives (II), wherein $R^1$, $R^3$, and $R^4$ are as hereinbefore defined, with a boronic acid of formula (III), wherein $R^2$ is as hereinbefore defined, gives compounds of formula (Ia), wherein $R^1$, $R^2$, $R^3$, and $R^4$ are as hereinbefore defined. The reaction is carried out in the presence of a copper salt such as cupric acetate and an organic base, preferably an amine base such as triethylamine, in an inert solvent such as dioxane, methylene chloride or tetrahydrofuran, at a temperature from −20° C. to the boiling point of the solvent.

Alternatively, condensation of 4-aminopyridazin-3(2H)-ones (II) with an heteroaryl bromide of formula (IV) wherein $R^2$ is as hereinbefore defined, gives compounds (Ia), wherein $R^1$, $R^2$, $R^3$, and $R^4$ are as hereinbefore defined. The reaction is carried out in the presence of a copper salt such as cuprous iodide and an inorganic base such as potassium phosphate, potassium carbonate or sodium carbonate and can also be performed in the presence of an organic base, preferably a diamine base such as N,N'-dimethylethylenediamine in an inert solvent such as toluene, dioxane or dimethylformamide, at a temperature from −20° C. to the boiling point of the solvent. It can also be performed neat.

Compound (Ia) may be optionally hydrolised with a suitable base to yield an acid intermediate. This intermediate is then alkylated using an alkylating agent of formula (VI), where $R^4$ has been previously defined and X is a leaving group such as a bromine or a chlorine atom, in an aprotic solvent in the presence of a base using known methods, for example D. A. White *Synthetic Communications,* 1977, 7(8), 559-568, giving compounds of formula (Ib), where $R^1$, $R^3$ and $R^4$ have been previously defined.

As an alternative these intermediate acids, can also be converted to (Ib) by condensation with an alcohol of formula (VII) in the presence of triphenylphosphine and diethyl azodicarboxylate using known methods, for example O. Mitsunobu *Synthesis,* 1981, 1, 1-28.

Pyridazin-3(2H)-ones of formula (V) in particular those of formula (Va) where $R^3$ is a group Ra—CO— wherein Ra represents an alkylcarbonyl group wherein the alkyl group may be substituted by one or more substituents selected from halogen atoms and phenyl, hydroxy, hydroxyalkyl, alkoxy, aryloxy, alkylthio, arylthio, oxo, amino, mono- or di-alkylamino, acylamino, hydroxycarbonyl, alkoxycarbonyl, carbamoyl, mono- or di-alkylcarbamoyl groups and those of formula (Vb) wherein $R^3$ is a hydrogen atom, may be obtained as shown in Scheme 2.

Scheme 2

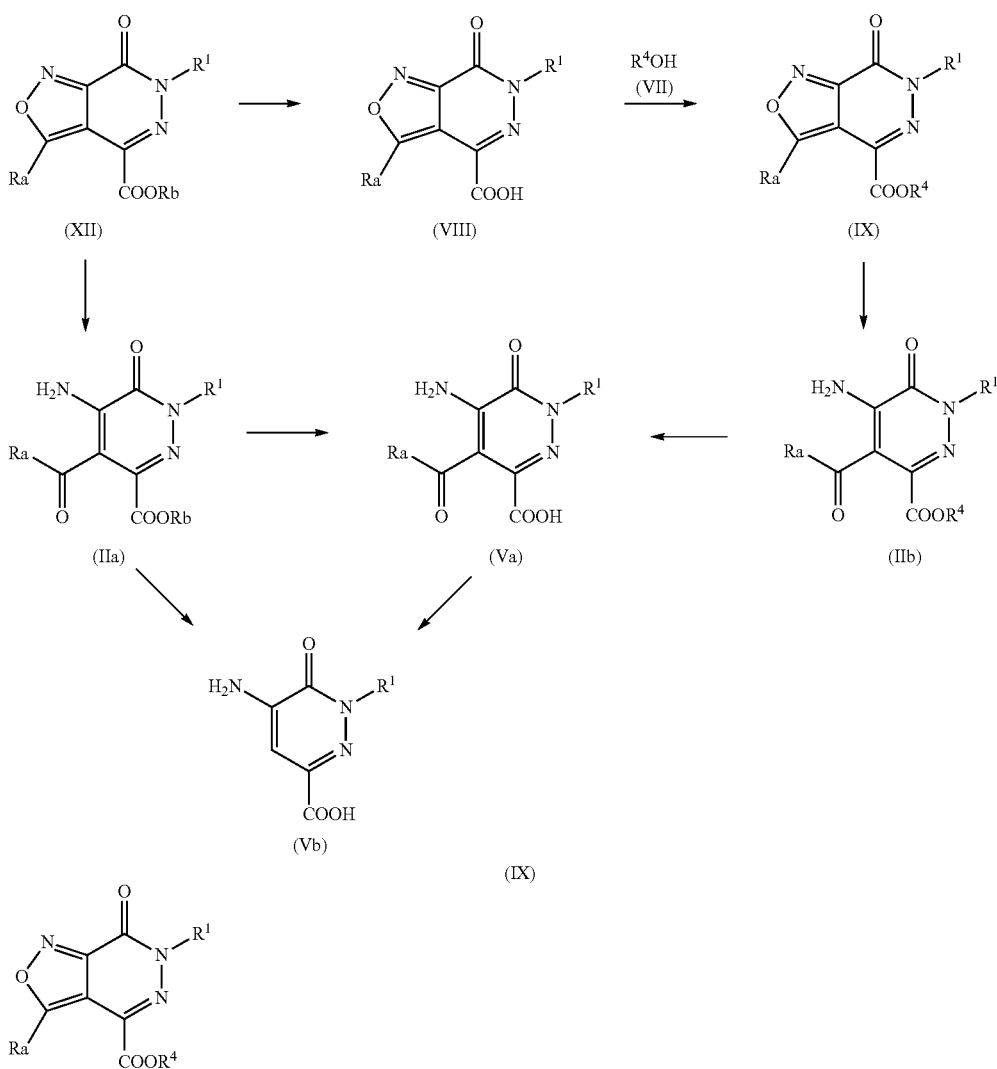

Isoxazolo[3,4-d]pyridazin-7(6H)-ones of formula (XII), wherein $R^1$ and Ra are as hereinbefore defined and Rb is a short chain alkyl rest, are hydrogenated to yield 4-aminopyridazin-3(2H)-one derivatives (IIa), wherein $R^1$, Ra and Rb are as hereinbefore defined. The hydrogenation may be performed using for example hydrogen in the presence of a catalyst by methods known per se, e.g. V. Dal Piaz et al. *Heterocycles,* 1991, 32, 1173.

Alternatively, isoxazolo[3,4-d]pyridazin-7(6H)-ones of formula (XII), wherein $R^1$, Ra and Rb are as hereinbefore defined are hydrolysed with sodium or potassium hydroxide and the resulting product is subsequently neutralised with an inorganic acid such as hydrochloric or sulphuric acid to give the corresponding carboxylic acid derivatives of formula (VIII), wherein $R^1$ and Ra are as hereinbefore defined. The reaction is preferably carried out in a solvent such as methanol, ethanol, tetrahydrofuran or an aqueous mixture of one of the above mentioned solvents at its boiling point.

Isoxazole derivatives of formula (VIII), wherein $R^1$ and Ra are as hereinbefore defined, are condensed with an alcohol of formula (VII) wherein $R^4$ is as hereinbefore defined, according the method above described, (O. Mitsunobu. *Synthesis,* 1981, 1, 1-28) to give compounds of formula (IX), wherein $R^1$, Ra and $R^4$ are as hereinbefore defined.

Isoxazolo[3,4-d]pyridazin-7(6H)-ones of formula (IX), wherein $R^1$, Ra and $R^4$ are as hereinbefore defined, are hydrogenated to yield 4-aminopyridazin-3(2H)-one derivatives (IIb), wherein $R^1$, Ra and $R^4$ are as hereinbefore defined. The hydrogenation may be performed using for example hydrogen in the presence of a catalyst by methods known per se, e.g. V. Dal Piaz et al. *Heterocycles,* 1991, 32, 1173.

Hydrolysis of 4-aminopyridazin-3(2H)-one derivatives (IIb), wherein $R^1$, Ra and $R^4$ are as hereinbefore defined, with sodium or potassium hydroxide and subsequent neutralisation with an inorganic acid such as hydrochloric or sulphuric acid provides the corresponding carboxylic acid derivatives of formula (Va), wherein $R^1$ and Ra are as hereinbefore defined. The reaction is preferably carried out in a solvent such as methanol, ethanol, tetrahydrofuran or an aqueous mixture of one of the above mentioned solvents at its boiling point. The same procedure may be followed to hydrolise the compounds of formula (IIa).

Treatment of 4-aminopyridazin-3(2H)-one derivatives (IIa), wherein $R^1$, Ra and Rb are as hereinbefore defined, or the carboxylic acid derivatives (Va), wherein $R^1$ and Ra are as hereinbefore defined, with hydrobromic acid at reflux, gives compounds (Vb), wherein $R^1$ is as hereinbefore defined.

Isoxazolo[3,4-d]pyridazin-7(6H)-ones of formula (XII) may be obtained as shown in Scheme 3.

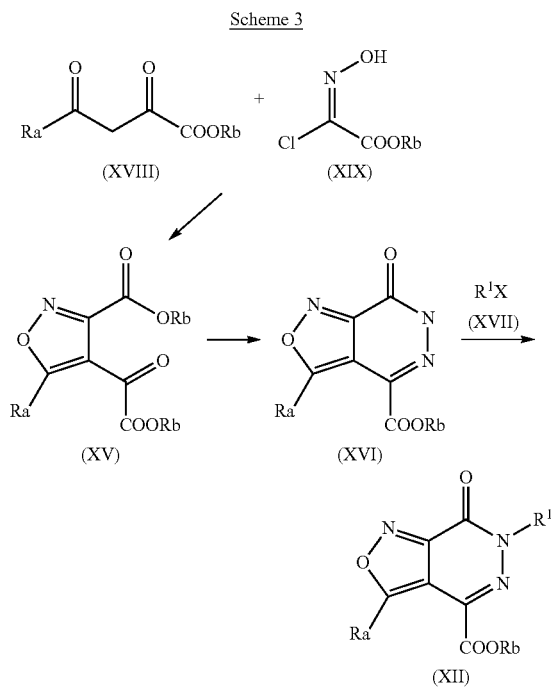

Scheme 3

Reaction of a 2,4-dioxoester derivative of general formula (XVIII), wherein Ra and Rb are as hereinbefore defined, and a 2-chloro-2-(hydroxyimino)acetate derivative of formula (XIX), wherein Rb is as hereinbefore defined, following methods known per se, e.g. G. Renzi et al., *Gazz. Chim. Ital.* 1965, 95, 1478, gives isoxazole derivatives of formula (XV), wherein Ra and Rb are as hereinbefore defined.

Isoxazole derivatives of formula (XV), wherein Ra and Rb are hereinbefore defined, are condensed with hydrazine, by methods known per se, e.g. G. Renzi et al., *Gazz. Chim. Ital.* 1965, 95, 1478, to give isoxazolo[3,4-d]pyridazin-7(6H)-ones of formula (XVI) wherein Ra and Rb are as hereinbefore defined. Subsequent reaction with an alkylating agent of formula (XVII), wherein $R^1$ is as hereinbefore defined and X is a leaving group such as a chlorine or a bromine atom or a methanesulfonate, p-toluenesulfonate or a benzenesulfonate group, by methods known per se, e.g. V. Dal Piaz et al. *Drug Des. Discovery* 1996, 14, 53; or condensation with an alcohol of formula (XVII) wherein $R^1$ is as hereinbefore described and X is a hydroxy group in the presence of triphenylphosphine and diethyl azodicarboxylate by methods known per se, e.g. O. Mitsunobu et al. *J. Am. Chem. Soc.* 1972, 94, 679; gives isoxazolo[3,4-d]pyridazin-7(6H)-ones of formula (XII), wherein $R^1$, Ra and Rb are as hereinbefore defined.

When the defined groups $R^1$ to $R^4$ are susceptible to chemical reaction under the conditions of the hereinbefore described processes or are incompatible with said processes, conventional protecting groups may be used in accordance with standard practice, for example see T. W. Greene and P. G. M. Wuts in 'Protective Groups in Organic Chemistry', 3$^{rd}$ Edition, John Wiley & Sons (1999). It may be that deprotection will form the last step in the synthesis of compounds of formula (I).

The compounds of formulae (III), (IV), (VI), (VII), (XVII), (XVIII) and (XIX) are known compounds or can be prepared by analogy with known methods.

Pharmacological Activity

PDE4 Assay Procedure

Compounds to be tested were resuspended in DMSO at a stock concentration of 1 mM. The compounds were tested at different concentrations varying from 10 pM to 10 μM to calculate an $IC_{50}$. These dilutions were done in 96-well plates. In some cases, plates containing diluted compounds were frozen before being assayed. In these cases, the plates were thawed at room temperature and stirred for 15 minutes.

Ten microliters of the diluted compounds were poured into a "low binding" assay plate. Eighty microliters of reaction mixture containing 50 mM Tris pH 7.5, 8.3 mM $MgCl_2$, 1.7 mM EGTA, and 15 nM [3H]-cAMP were added to each well. The reaction was initiated by adding ten microliters of a solution containing PDE4. The plate was then incubated under stirring for 1 hour at room temperature. After incubation the reaction was stopped with 50 microlitres of SPA beads, and the reaction was allowed to incubate for another 20 minutes at room temperature before measuring radioactivity using standard instrumentation.

The reaction mixture was prepared by adding 90 ml of $H_2O$ to 10 ml of 10× assay buffer (500 mM Tris pH 7.5, 83 mM $MgCl_2$, 17 mM EGTA), and 40 microlitres 1 μCi/μL [3H]-cAMP. SPA beads solution was prepared by adding 500 mg to 28 ml $H_2O$ for a final concentration of 20 mg/ml beads and 18 mM zinc sulphate.

The results are shown in Table 1.

| No | HPDE4B or $IC_{50}$ PDE4 (nM) |
|---|---|
| 1 | 52 |
| 5 | 110 |
| 7 | 10 |
| 10 | 19 |
| 11 | 1.6 |
| 13 | 2.9 |
| 14 | 2.4 |
| 19 | 9.8 |
| 23 | 14 |
| 26 | 5.1 |
| 27 | 16 |
| 33 | 1.9 |
| 36 | 44 |
| 38 | 13 |
| 39 | 1.5 |
| 41 | 69 |
| 49 | 0.73 |
| 51 | 0.48 |
| 66 | 0.36 |
| 69 | 0.49 |
| 71 | 5.0 |

It can be seen from Table 1 that the compounds of formula (I) are potent inhibitors of phosphodiesterase 4 (PDE 4). Preferred pyridazin-3(2H)-one derivatives of the invention possess an $IC_{50}$ value for the inhibition of PDE4 (determined as defined above) of less than 120 nM, preferably less than 50 nM and most preferably less than 30 nM. The compounds are also capable of blocking the production of some pro-inflammatory cytokines such as, for example, TNFα.

Thus, they can be used in the treatment of allergic, inflammatory and immunological diseases, as well as those diseases or conditions where the blockade of pro-inflammatory cytokines or the selective inhibition of PDE 4 could be of benefit.

These disease states include asthma, chronic obstructive pulmonary disease, allergic rhinitis, rheumatoid arthritis, osteoarthritis, osteoporosis, bone-formation disorders, glomerulonephritis, multiple sclerosis, ankylosing spondylitis, Graves ophthalmopathy, myasthenia gravis, diabetes insipidus, graft rejection, gastrointestinal disorders such as irritable bowel disease, ulcerative colitis or Crohn disease, septic shock, adult distress respiratory syndrome, and skin diseases such as atopic dermatitis, contact dermatitis, acute dermatomyositis and psoriasis. They can also be used as improvers of cerebrovascular function as well as in the treatment of other CNS related diseases such as dementia, Alzheimer's disease, depression, and as nootropic agents.

Plasma Stability Assay

For plasma stability assays, compounds in acetonitrile or dimethylsulfoxide solutions are added in duplicate to 1 mL plasma pre-warmed at 37° C. at a final concentration of 1 µg/mL (less than 1% organic solvent added). Just after the addition of the compounds and mixing (t=0 h), 100 µL samples are collected and transferred to tubes containing 300 µL of 0.5% trifluoro acetic acid in acetonitrile in an ice bath in order to stop the reaction. Samples are kept in a water bath at 37° C. during the assay. At different time intervals (i.e. t=0.5, 1, 3 and 24 h) samples are collected and reaction stopped as described previously. The aliquots are centrifuged at 4000 rpm for 10 minutes, 100 µL of supernatant diluted with 100 µL Milli-Q water and 5 µL injected in a HPLC/MS system. Both the parent compound and the possible by-products are monitored. The stability is calculated by comparing the compound response obtained at a given time with the response at time=0 h.

The compounds of the present invention show a short half life in plasma, which is preferably shorter than 5 hours, more preferably shorter than 3 hours and most preferably shorter than 1 hour. The free acid derivatives originating from the hydrolysis of the group —COOR$^4$ of the compounds of the present invention have an $IC_{50}$ value for the inhibition of PDE4 which is several times higher than the $IC_{50}$ value of the non-hydrolised compounds.

Consequently the pyridazin-3(2H)-one derivative of the invention can be administered to a subject in need thereof at relatively high doses without causing undesirable systemic effects as a result of both their short half lives in plasma and the reduced PDE4 inhibition capacity of the their hydrolysates.

The compounds of the present invention are also of benefit when administered in combination with other drugs such as steroids and immunosuppressive agents, such as cyclosporin A, rapamycin, T-cell receptor blockers, β2-adrenergic agonists or antagonists of M3 muscarinic receptors. In this case the administration of the compounds allows a reduction of the dosage of the other drugs, thus preventing the appearance of the undesired side effects associated with both steroids and immunosuppressants.

Like other PDE4 inhibitors (see references above) the compounds of the invention can also be used for blocking, after preventive and/or curative treatment, the erosive and ulcerogenic effects induced by a variety of etiological agents, such as antiinflammatory drugs (steroidal or non-steroidal antiinflammatory agents), stress, ammonia, ethanol and concentrated acids.

They can be used alone or in combination with antacids and/or antisecretory drugs in the preventive and/or curative treatment of gastrointestinal pathologies like drug-induced ulcers, peptic ulcers, *H. Pylori*-related ulcers, esophagitis and gastro-esophageal reflux disease.

They can also be used in the treatment of pathological situations where damage to the cells or tissues is produced through conditions like anoxia or the production of an excess of free radicals. Examples of such beneficial effects are the protection of cardiac tissue after coronary artery occlusion or the prolongation of cell and tissue viability when the compounds of the invention are added to preserving solutions intended for storage of transplant organs or fluids such as blood or sperm. They are also of benefit on tissue repair and wound healing.

Accordingly, the pyridazin-3(2H)-one derivatives of the invention and pharmaceutically acceptable salts thereof, and pharmaceutical compositions comprising such compound and/or salts thereof, may be used in a method of treatment or prevention of disorders of the human body susceptible to amelioration by inhibition of phosphodiesterase 4 which comprises administering to a patient requiring such treatment an effective amount of a pyridazin-3(2H)-one derivative of the invention.

The results of table I show that the compounds of formula (I) are potent inhibitors of phosphodiesterase 4 (PDE4) and are therefore useful in the treatment or prevention of pathological conditions, diseases and disorders known to be susceptible of amelioration by inhibition of PDE4, such as asthma, chronic obstructive pulmonary disease, rheumatoid arthritis, atopic dermatitis, psoriasis or irritable bowel disease.

The compounds of the present invention can also be used in combination with other drugs known to be effective in the treatment of these diseases. For example, in combination with steroids, immunosuppressive agents, T-cell receptor blockers, antiinflammatory drugs β2-adrenergic agonists and/or antagonists of M3 muscarinic receptors for simultaneous, separate or sequential use in the treatment of the human or animal body Accordingly, another embodiment of the invention is the use of the compounds of formula (I) in the manufacture of a medicament for treatment or prevention of pathological conditions, diseases and disorders known to be susceptible of amelioration by inhibition of PDE4, as well as a method for treating a subject afflicted with a pathological condition or disease susceptible to amelioration by inhibition of PDE4, which comprises administering to said subject an effective amount of a compound of formula (I).

The present invention also provides pharmaceutical compositions which comprise, as an active ingredient, at least a pyridazin-3(2H)-one derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Compositions for topical administration may take the form of ointments, creams or lotions, all containing the compound of the invention; such preparations may be made by methods well-known in the art.

Effective doses are normally in the range of 10-600 mg of active ingredient per day. Daily dosage may be administered in one or more treatments, preferably from 1 to 4 treatments, per day.

The syntheses of the compounds of the invention and of the intermediates for use therein are illustrated by the following Examples (including Preparation Examples 1 to 50) which do not limit the scope of the invention in any way.

$^1$H Nuclear Magnetic Resonance Spectra were recorded on a Varian Gemini 300 spectrometer.

Low Resolution Mass Spectra (m/z) were recorded on a Micromass ZMD mass spectrometer using ESI ionization.

Melting points were recorded using a Perkin Elmer DSC-7 apparatus.

The chromatographic separations were obtained using a Waters 2690 system equipped with a Symmetry C18 (2.1×10 mm, 3.5 mM) column. The mobile phase was formic acid (0.4 mL), ammonia (0.1 mL), methanol (500 mL) and acetonitrile (500 mL) (B) and formic acid (0.46 mL), ammonia (0.115 mL) and water (1000 mL) (A): initially from 0% to 95% of B in 20 min, and then 4 min. with 95% of B. The reequilibration time between two injections was 5 min. The flow rate was 0.4 mL/min. The injection volume was 5 microliter. Diode array chromatograms were collected at 210 nM.

PREPARATION EXAMPLES

Preparation 1

Ethyl 4-[ethoxy(oxo)acetyl]-5-methylisoxazole-3-carboxylate

To an ice-cooled solution of sodium ethoxide (12.92 g, 0.19 mol) in 160 mL of dry ethanol ethyl 2,4-dioxovalerate (25.0 g, 0.158 mol) was added dropwise and the mixture was stirred at 0° C. for 30 min. A solution of ethyl chloro(hydroxyimino) acetate (28.79 g, 0.190 mol) in 50 mL of dry ethanol was added dropwise. Then it was stirred at 0° C. for 30 min and at room temperature for 19 hours. Finally solvent was removed and the crude thus obtained was partitioned between ethyl acetate and water. The organic phase was dried and solvent removed to yield the desired product (100%) as an orange oil.

δ (CDCl$_3$): 1.40 (m, 6H), 2.70 (s, 3H), 4.40 (m, 4H).

Preparation 2

Ethyl 3-methyl-7-oxo-6,7-dihydroisoxazolo[3,4-d]pyridazine-4-carboxylate

Hydrazine monohydrate (8.7 mL, 180 mmol) was added dropwise to a solution of the title compound of Preparation 1 (38.3 g, 150 mmol) in dry ethanol (75 mL) and the resulting mixture was stirred overnight. After cooling with an ice bath, a precipitate was formed which was collected by filtration and washed with diethyl ether to yield the title compound (19.2 g, 57% yield) as a yellow solid.

δ (CDCl$_3$): 1.41 (t, 3H), 3.01 (s, 3H), 4.50 (q, 2H), 6.30 (s, 1H).

Preparation 3

Ethyl 6-ethyl-3-methyl-7-oxo-6,7-dihydroisoxazolo[3,4-d]pyridazine-4-carboxylate To a suspension of the title compound of Preparation 2 (10.0 g, 44 mmol) and anhydrous potassium carbonate (30 g, 220 mmol) in dry dimethylformamide (50 mL) was added ethyl bromide (19.6 mL, 264 mmol) and the resulting mixture stirred at r.t. overnight. The mixture was concentrated and the residue thus obtained was suspended in dichloromethane, washed with water and brine, dried and concentrated to yield the title compound (9.72 g, 88% yield) as a yellow solid.

δ (CDCl$_3$): 1.42 (m, 6H), 3.00 (s, 3H), 4.25 (q, 2H), 4.48 (q, 2H)

Preparation 4

Ethyl 4-acetyl-5-amino-1-ethyl-6-oxo-1,6-dihydropyridazine-3-carboxylate

A mixture of the title compound of Preparation 3 (1.0 g, 4 mmol) and 10% palladium on charcoal (200 mg) in ethanol (100 mL) was shaken under hydrogen at room temperature and 30 psi for 6 h. The catalyst was filtered off and the solvent was removed under reduced pressure to yield the title compound (950 mg, 98% yield).

δ (CDCl$_3$): 1.38 (m, 6H), 2.30 (s, 3H), 4.22 (q, 2H), 4.42 (q, 2H), 7.50 (bs, 2H).

Preparation 5

5-Amino-1-ethyl-6-oxo-1,6-dihydropyridazine-3-carboxylic acid

A mixture of the title compound of Preparation 4 (0.25 g, 0.99 mmol) and 48% bromhydric acid (2 mL) is heated to 130° C. for 3 h. Very slowly, this reaction mixture is neutralized at room temperature with 8N NaOH and finally with solid potassium carbonate. Once the solvent is eliminated under reduced pressure, the residue is treated with boiling ethanol and filtered. This organic phase is evaporated and 0.17 g of the final product are obtained. Yield=94%.

δ (DMSO-d6): 1.3 (t, J=7.2 Hz, 3 H) 4.1 (q, J=7.1 Hz, 2 H) 6.7 (s, 2 H) 6.8 (s, 1 H) 13.1 (s, 1 H)

Preparation 6

Benzyl 5-amino-1-ethyl-6-oxo-1,6-dihydropyridazine-3-carboxylate

A mixture of the title compound of Preparation 5 (1.00 g, 5.46 mmol), benzyl bromide (1.94 mL, 16.4 mmol) and potassium carbonate (0.76 g, 5.46 mmol) in dimethylformamide (25 mL) is heated at 80° C. for 24 h. Once the solvent is evaporated under reduced pressure, the residue is suspended in water and extracted twice with chloroform. The organic phase is washed with water and brine, dried over magnesium sulphate, filtered and evaporated. The purification through a flash chromatography column (3:1 hexane/ethyl acetate to 1:1 as eluent) yields 0.85 g of the desired final compound. Yield=57%

$\delta$ (CDCl$_3$): 1.4 (t, J=7.1 Hz, 3 H) 4.3 (q, J=7.2 Hz, 2 H) 5.0 (s, 2 H) 5.4 (s, 2 H) 6.9 (s, 1 H) 7.4 (m, 5 H)

Preparation 7

Ethyl 5-amino-1-ethyl-6-oxo-1,6-dihydropyridazine-3-carboxylate

A mixture of the title compound of Preparation 5 (1.00 g, 5.46 mmol), ethyl bromide (1.51 mL, 16.4 mmol) and potassium carbonate (0.76 g, 5.46 mmol) in dimethylformamide (30 mL) is heated at 50° C. for 24 h. The solvent is evaporated under reduced pressure and the residue is suspended in water and extracted twice with chloroform. The organic phase is washed with water and brine, dried with magnesium sulphate, filtered and the solvent evaporated under reduced pressure. After purification of the residue through a flash chromatography column, eluting with 2:1 hexane/ethyl acetate, 0.86 g of the desired final compound are isolated. Yield=74%

$\delta$ (CDCl$_3$): 1.4 (m, 6 H) 4.3 (q, J=7.4 Hz, 2 H) 4.4 (q, J=7.0 Hz, 2 H) 5.1 (s, 2 H) 6.9 (s, 1 H)

Preparation 8

Isopropyl 5-amino-1-ethyl-6-oxo-1,6-dihydropyridazine-3-carboxylate

The final product of Preparation 5 (1.00 g, 5.46 mmol), isopropanol (0.42 mL, 5.46 mmol), DEAD (0.86 mL, 5.46 mmol) and triphenylphosphine (1.43 g, 5.46 mmol) are suspended in tetrahydrofurane (60 mL) and stirred overnight under inert atmosphere at room temperature. The solvent is evaporated under reduced pressure and the residue purified through a flash chromatography column, eluting with 2:1 hexane/ethyl acetate. The desired final compound is obtained in a quantitative yield.

$\delta$ (CDCl$_3$): 1.4 (m, 9 H) 4.3 (q, J=7.3 Hz, 2 H) 5.0 (s, 2 H) 5.2 (m, 1 H) 6.9 (s, 1 H)

Preparation 9

Pyridin-2-ylmethyl 5-amino-1-ethyl-6-oxo-1,6-dihydropyridazine-3-carboxylate

Obtained (29%) as described in Preparation 7 but using 2-chloromethylpyridine chlorhydrate instead of ethyl bromide.

$\delta$ (CDCl$_3$): 1.4 (t, J=7.2 Hz, 3 H) 4.3 (q, J=7.2 Hz, 2 H) 5.1 (s, 2 H) 5.5 (s, 2 H) 7.0 (s, 1 H) 7.3 (m, 1 H) 7.4 (d, J=8.1 Hz, 1 H) 7.7 (t, J=7.4 Hz, 1 H) 8.6 (d, J=3.0 Hz, 1 H)

Preparation 10

Thiophen-3-ylmethyl 5-amino-1-ethyl-6-oxo-1,6-dihydropyridazine-3-carboxylate

Obtained (90%) as described in Preparation 8 but using 3-hydroxymethylthiophene instead of isopropanol.

$\delta$ (CDCl$_3$): 1.4 (t, J=7.2 Hz, 3 H) 4.3 (q, J=7.4 Hz, 2 H) 5.0 (s, 2 H) 5.4 (s, 2 H) 6.9 (s, 1 H) 7.2 (s, 1 H) 7.3 (s, 1 H) 7.4 (s, 1 H)

Preparation 11

3-Methoxybenzyl 5-amino-1-ethyl-6-oxo-1,6-dihydropyridazine-3-carboxylate

Obtained (32%) as described in Preparation 7 but using 3-methoxybenzylchloride instead of ethyl bromide.

$\delta$ (CDCl$_3$): 1.4 (t, J=7.1 Hz, 3 H) 3.8 (s, 3 H) 4.3 (q, J=7.1 Hz, 2 H) 5.0 (s, 2 H) 5.4 (s, 2 H) 6.9 (d, J=5.8 Hz, 1 H) 6.9 (s, 1 H) 7.0 (m, 2 H) 7.3 (t, J=7.8 Hz, 1 H)

Preparation 12

3-Chlorobenzyl 5-amino-1-ethyl-6-oxo-1,6-dihydropyridazine-3-carboxylate

Obtained (12%) as described in Preparation 7 but using 3-chlorobenzylbromide instead of ethyl bromide.

$\delta$ (CDCl$_3$): 1.4 (t, J=7.1 Hz, 3 H) 4.3 (q, J=7.1 Hz, 2 H) 5.1 (s, 2 H) 5.3 (s, 2 H) 6.9 (s, 1 H) 7.3 (s, 3 H) 7.4 (s, 1 H)

Preparation 13

1-Phenylethyl 5-amino-1-ethyl-6-oxo-1,6-dihydropyridazine-3-carboxylate

Obtained (45%) as described in Preparation 7 but using 2-bromoethylbenzene instead of ethyl bromide.

$\delta$(CDCl$_3$): 1.4 (t, J=7.3 Hz, 3 H) 1.7 (d, J=6.6 Hz, 3 H) 4.3 (q, J=7.1 Hz, 2 H) 5.0 (s, 2 H) 6.1 (q, J=6.4 Hz, 1 H) 6.9 (s, 1 H) 7.4 (m, 5 H)

Preparation 14

1-Pyridin-4-ylethyl 5-amino-1-ethyl-6-oxo-1,6-dihydropyridazine-3-carboxylate

Obtained (78%) as described in Preparation 8 but using 1-pyridin-4-ylethanol instead of isopropanol.

$\delta$ (CDCl$_3$): 1.4 (t, J=7.1 Hz, 3 H) 1.7 (d, J=6.6 Hz, 3 H) 4.3 (q, J=7.1 Hz, 2 H) 5.1 (s, 2 H) 6.1 (q, J=6.6 Hz, 1 H) 6.9 (s, 1 H) 7.3 (d, J=6.0 Hz, 2 H) 8.6 (d, J=5.8 Hz, 2 H)

Preparation 15

Indan-1-yl 5-amino-1-ethyl-6-oxo-1,6-dihydropyridazine-3-carboxylate

Obtained (50%) as described in Preparation 8 but using indan-1-ol instead of isopropanol.

$\delta$(CDCl$_3$): 1.4 (t, J=7.1 Hz, 3 H) 2.3 (m, 1 H) 2.6 (m, 1 H) 2.9 (m, 1 H) 3.2 (m, 1 H) 4.3 (q, 2 H) 5.0 (s, 2 H) 6.4 (dd, J=7.0, 3.7 Hz, 1 H) 6.9 (s, 1 H) 7.2 (m, 1 H) 7.3 (m, 2 H) 7.5 (d, J=7.4 Hz, 1 H).

Preparation 16

4-Acetyl-5-amino-1-ethyl-6-oxo-1,6-dihydropyridazine-3-carboxylic acid

A mixture of the title compound of Preparation 4 (3.46 g, 13.66 mmol) and 1 N sodium hydroxide (60 mL) in 120 mL of ethanol was stirred at room temperature for 30 min. The solvent was removed under reduced pressure and the crude acidified with 1 N hydrogen chloride (60 mL). The solution was extracted with ethyl acetate and the organic phase dried over sodium sulphate anhydride and concentrated to yield the title compound (2.45 g, 80% yield) as a white solid.

δ(CDCl$_3$): 1.4 (t, 3 H), 2.4 (bs, 3 H), 4.2 (q, 2 H).

Preparation 17

2-(Dimethylamino)-2-oxoethyl-4-acetyl-5-amino-1-ethyl-6-oxo-1,6-dihydropyridazine-3-carboxylate To a suspension of the title compound of Preparation 16 (400 mg, 1.78 mmol) and anhydrous potassium carbonate (245 mg, 1.78 mmol) in dry dimethylformamide (10 mL) was added 2-chloro-N,N-dimethylacetamide (366 mg, 3.55 mmol) and the resulting mixture was stirred at 50° C. for eight hours. The residue was suspended in water and ethyl acetate was added. The organic layer was washed with water, brine, dried over Na$_2$SO$_4$ anhydride and evaporated. The residue obtained was purified by column chromatography (silica gel, hexane/ethyl acetate 1:1) to yield the title compound (310 mg, 56% yield).

LRMS: m/Z 311 (M+1)+.

δ (CDCl$_3$): 1.4 (t, 3 H) 2.4 (s, 3 H) 3.0 (m, 6 H) 4.2 (q, 2 H) 5.0 (s, 2 H) 7.3 (m, 2 H).

Preparation 18

2-Methoxy-1-methyl-2-oxoethyl 4-acetyl-5-amino-1-ethyl-6-oxo-1,6-dihydropyridazine-3-carboxylate To a suspension of the title compound of Preparation 16 (300 mg, 1.33 mmol) and anhydrous potassium carbonate (184 mg, 1.33 mmol) in dry dimethylformamide (10 mL) was added methyl 2-bromopropionate (667 mg, 3.99 mmol) and the resulting mixture was stirred at room temperature for four hours. The residue was suspended in water and ethyl acetate was added. The organic layer was washed with water, brine, dried over Na$_2$SO$_4$ anhydride and evaporated to yield the title compound (270 mg, 65% yield).

LRMS: m/Z 312 (M+1)+.

δ (CDCl$_3$): 1.2 (t, 3 H) 1.6 (d, 3 H) 2.4 (s, 3 H) 3.8 (s, 3 H) 4.2 (q, 2 H) 5.3 (m, 1 H) 7.4 (br.s, 2 H).

Preparation 19

Benzyl 4-acetyl-5-amino-1-ethyl-6-oxo-1,6-dihydropyridazine-3-carboxylate

Obtained (43%) from the title compound from Preparation 16 and benzylbromide following the experimental procedure described in Preparation 18.

LRMS: m/Z 316 (M+1)+.

δ (CDCl$_3$): 1.4 (t, 3 H) 2.2 (s, 3 H) 4.2 (q, 2 H) 5.4 (s, 2 H) 7.5 (m, 7 H).

Preparation 20

Methyl 4-acetyl-5-amino-1-ethyl-6-oxo-1,6-dihydropyridazine-3-carboxylate.

Obtained (50%) from the title compound from Preparation 16 and iodomethane following the experimental procedure described in Preparation 18.

LRMS: m/Z 240 (M+1)+.

δ (CDCl$_3$): 1.4 (t, 3 H) 2.3 (s, 3 H) 4.0 (s, 3 H) 4.2 (q, 2 H) 7.5 (br.s, 2 H).

Preparation 21

Cyclopropylmethyl 4-acetyl-5-amino-1-ethyl-6-oxo-1,6-dihydropyridazine-3-carboxylate.

Obtained (68%) from the title compound from Preparation 16 and (bromomethyl)cyclopropane following the experimental procedure described in Preparation 17.

δ (CDCl$_3$): 0.4 (m, 2 H) 0.6 (m, 2 H), 1.2 (m, 1 H) 1.4 (t, 3 H) 2.4 (s, 3 H) 4.2 (m, 4 H) 7.5 (br.s, 2 H).

Preparation 22

3-Methylbutyl 4-acetyl-5-amino-1-ethyl-6-oxo-1,6-dihydropyridazine-3-carboxylate Obtained (61.5%) from the title compound from Preparation 16 and 1-bromo-3-methylbutane following the experimental procedure described in Preparation 17.

δ (CDCl$_3$): 0.9 (m, 6 H) 1.4 (t, 3 H), 1.7 (m, 3 H) 2.4 (s, 3 H) 4.2 (q, 2 H) 4.4 (m, 2 H) 7.5 (br.s, 2 H).

Preparation 23

2-Methoxyethyl 4-acetyl-5-amino-1-ethyl-6-oxo-1,6-dihydropyridazine-3-carboxylate Obtained (48%) from the title compound from Preparation 16 and 1-bromo-2-methoxyethane following the experimental procedure described in Preparation 17.

δ (CDCl$_3$): 0.9 (m, 6 H) 1.4 (t, 3 H), 1.7 (m, 3 H) 2.4 (s, 3 H) 4.2 (q, 2 H) 4.4 (m, 2 H) 7.5 (br.s, 2 H).

Preparation 24

2-Phenylethyl 4-acetyl-5-amino-1-ethyl-6-oxo-1,6-dihydropyridazine-3-carboxylate Obtained (65.5%) from the title compound from Preparation 16 and (2-bromoethyl)benzene following the experimental procedure described in Preparation 17.

δ (CDCl$_3$): 1.4 (t, 3 H), 2.1 (s, 3 H) 3.1 (t, 2 H) 4.2 (q, 2 H) 4.6 (t, 2 H) 7.3 (m, 5 H) 7.5 (br.s, 2 H).

Preparation 25

1-Methyl-2-phenylethyl 4-acetyl-5-amino-1-ethyl-6-oxo-1,6-dihydropyridazine-3-carboxylate Obtained (52%) from the title compound from Preparation 16 and (2-bromopropyl)benzene following the experimental procedure described in Preparation 17.

δ (CDCl$_3$): 1.4 (t, 3H), 2.05 (s, 3H) 2.9 (dd, 1H) 3.1 (dd, 1H) 4.2 (q, 2H) 5.4 (m, 1H) 7.2 (m, 5H) 7.5 (br.s, 2H).

Preparation 26

1-Phenylethyl 4-acetyl-5-amino-1-ethyl-6-oxo-1,6-dihydropyridazine-3-carboxylate Obtained (97.7%) from the title compound from Preparation 16 and (1-bromoethyl)benzene following the experimental procedure described in Preparation 17.

δ (CDCl$_3$): 1.4 (t, 3 H), 1.7 (d, 3 H) 2.1 (s, 3 H) 4.2 (q, 2 H) 6.1 (q, 1 H) 7.4 (m, 7 H).

Preparation 27

Cyclobutyl 4-acetyl-5-amino-1-ethyl-6-oxo-1,6-dihydropyridazine-3-carboxylate To a solution of PPh$_3$ (349 mg, 1.33 mmol), cyclobutanol (0.104 mL, 1.33 mmol), and the compound of Preparation 16 (300 mg, 1.33 mmol) in 10 mL dry THF under nitrogen was added DEAD (0.21 mL, 1.33 mmol) and the resulting mixture was stirred at room temperature overnight. Then solvent was evaporated and the residue was purified by column chromatography (silica gel, hexane/ethyl acetate 9:1) to yield the title compound (248 mg, 67% yield).
LRMS: m/Z 280 (M+1)+.
Retention Time: 7.4 min.

Preparation 28

Cyclohexyl 4-acetyl-5-amino-1-ethyl-6-oxo-1,6-dihydropyridazine-3-carboxylate Obtained (36%) from the title compound from Preparation 16 and cyclohexanol following the experimental procedure described in Preparation 27.
LRMS: m/Z 308 (M+1)+.
δ (CDCl$_3$): 1.2-2.0 (m, 13 H) 2.4 (s, 3 H) 4.2 (q, 2 H) 5.0 (m, 1 H) 7.5 (br.s, 2 H).

Preparation 29 sec-Butyl 4-acetyl-5-amino-1-ethyl-6-oxo-1,6-dihydropyridazine-3-carboxylate Obtained (91%) from the title compound from Preparation 16 and sec-butanol following the experimental procedure described in Preparation 27.
LRMS: m/Z 282 (M+1)+.
δ (CDCl$_3$): 1.0 (t, 3 H) 1.4 (m, 6 H) 1.7 (m, 2 H) 2.4 (s, 3 H) 4.2 (q, 2 H) 5.1 (m, 1 H) 7.5 (br.s, 2 H).

Preparation 30

6-Ethyl-3-methyl-7-oxo-6,7-dihydro-isoxazolo[3,4-d]pyridazine-4-carboxylic acid To a stirred solution of the title compound of Preparation 3 (1.5 g, 5.97 mmol) in 45 mL of a 2:1 methanol/THF mixture, a solution of lithium hydroxide (0.57 g, 23.88 mmol) in 8 mL of water was added dropwise. The final mixture was stirred at room temperature for 1 hour and then diluted with some water and acidified with HCl 2N. It was extracted with ethyl acetate, dried and solvent removed to yield (89%) the title product.
δ (DMSO-d$_3$): 1.30 (t, 3 H), 2.90 (s, 3 H), 4.15 (q, 2 H).

Preparation 31

Isopropyl 6-ethyl-3-methyl-7-oxo-6,7-dihydroisoxazolo[3,4-d]pyridazine-4-carboxylate To a solution of PPh$_3$ (353 mg, 1.34 mmol), propan-2-ol (0.103 mL, 1.34 mmol), and the compound of Preparation 30 (300 mg, 1.34 mmol) in 7 mL of dry THF under nitrogen was added DEAD (0.211 mL, 1.34 mmol) and the resulting mixture was stirred at room temperature overnight. Then solvent was evaporated and the residue was purified by column chromatography (silica gel, hexane/ethyl acetate 6:4) to yield the title compound (220 mg, 62% yield).
LRMS: m/Z 266 (M+1)+.
δ (CDCl$_3$): 1.4 (m, 9 H) 3.0 (s, 3 H) 4.3 (q, 2 H) 5.3 (q, 1 H).

Preparation 32

Isopropyl 4-acetyl-5-amino-1-ethyl-6-oxo-1,6-dihydropyridazine-3-carboxylate.

A mixture of the title compound of Preparation 31 (214 mg, 0.8 mmol) and 20% palladium on charcoal (43 mg) in ethanol (10 mL) was shaken under hydrogen at room temperature and 2 bar for 5 h. The catalyst was filtered off and the solvent was removed under reduced pressure to yield the title compound (214 mg, 99% yield).
LRMS: m/Z 268 (M+1)+.
δ (DMSO-D6): 1.1 (m, 9 H) 2.2 (s, 3 H) 3.9 (q, 2 H) 4.9 (m, 1 H) 7.4 (m, 2H).

Preparation 33 tert-Butyl 6-ethyl-3-methyl-7-oxo-6,7-dihydroisoxazolo[3,4-d]pyridazine-4-carboxylate The title compound of Preparation 30 (300 mg, 1.34 mmol) was dissolved in 30 mL dry toluene and heated to reflux. Then N,N-dimethylformamide di-t-butyl acetal (1.29 mL, 5.38 mmol) was added dropwise to the refluxing mixture within 20 min. The solution was refluxed for a further 40 min, cooled, and washed with water, saturated sodium hydrogen carbonate solution and brine. The organic layer is dried with sodium sulphate anhydride and the solvent evaporated to give an orange solid (204 mg, 54% yield).
LRMS: m/Z 280 (M+1)+.
δ (CDCl$_3$): 1.4 (t, 3 H) 1.3 (m, 9 H) 3.0 (s, 3 H) 4.3 (q, 2 H).

Preparation 34 tert-Butyl 4-acetyl-5-amino-1-ethyl-6-oxo-1,6-dihydropyridazine-3-carboxylate Obtained (65%) from the title compound of Preparation 33 and following the experimental procedure described in Preparation 32.
LRMS: m/Z 282 (M+1)+.
δ (CDCl$_3$): 1.4 (t, 3 H) 1.6 (m, 9 H) 2.4 (s, 3 H) 4.2 (q, 2 H) 7.4 (br.s, 2H).

Preparation 35

Benzyloxycarbonylmethyl 5-amino-1-ethyl-6-oxo-1,6-dihydropyridazine-3-carboxylate 5-Amino-1-ethyl-6-oxo-1,6-dihydropyridazine-3-carboxylic acid (0.6 g, 3.3 mmol, see Preparation 5), benzyl bromoacetate (1.6 ml, 4.8 mmol), and potassium carbonate (0.5 g, 3.3 mmol) were suspended in dimethylformamide (30 ml) and heated overnight at 50° C. The solvent was evaporated under reduced pressure and the residue was passed through a silica-gel column, eluting with hexane/ethyl acetate 3:2, to yield 1.0 g of the desired final product. Yield=92%
δ (CDCl$_3$): 1.4 (t, J=7.3 Hz, 3 H) 4.3 (q, J=7.3 Hz, 2 H) 4.9 (s, 2 H) 5.1 (s, 2 H) 5.2 (s, 2 H) 7.0 (m, 1 H) 7.4 (s, 5 H)

Preparation 36

Ethyl 1-ethyl-5-(isoquinolin-4-ylamino)-6-oxo-1,6-dihydropyridazine-3-carboxylate

A mixture of the title compound of Preparation 7 (1.9 g, 9.1 mmol), 4-bromoisoquinoline (2.3 g, 10.9 mmol), copper(I) iodide (173 mg, 0.9 mmol), potassium carbonate (2.6 g, 19.0 mmol) and 1,1'-dimethylethylenediamine (194 µl, 1.8 mmol) in dioxane (10 ml) was heated at 120° C. in a sealed tube under nitrogen for 48 h. Once at room temperature, the inorganic salts were filtered and the solvent evaporated under reduced pressure. Purification of the residue through a flash chromatography column eluting with 2:1 hexane/ethyl acetate to 1:2 yielded 823 mg of the desired final compound. Yield=27%.

$\delta$ (CDCl$_3$): 1.3 (t, J=7.3 Hz, 3 H) 1.5 (t, J=7.3 Hz, 3 H) 4.3 (q, J=7.3 Hz, 2 H) 4.4 (q, J=7.3 Hz, 2 H) 6.9 (s, 1 H) 7.8 (m, 3 H) 7.9 (d, 1 H) 8.1 (d, 1H) 8.6 (bs, 1H) 9.2 (bs, 1H)

Preparation 37

1-Ethyl-5-(isoquinolin-4-ylamino)-6-oxo-1,6-dihydropyridazine-3-carboxylic acid

The title compound of Preparation 36 (823 mg, 2.4 mmol) was suspended in ethanol (70 ml) and NaOH 2N (3.7 ml, 7.3 mmol) was added. This mixture was stirred overnight at room temperature. The solvent was evaporated under reduced pressure and redissolved in water. This solution was neutralised with HCl 2N. A solid precipitated, which was filtered, washed with water and dried at 50° C. under reduced pressure. 637 mg of the desired final product were obtained. Yield=84%

$\delta$ (CDCl$_3$): 1.3 (t, J=7.3 Hz, 3 H) 4.3 (q, J=7.3 Hz, 2 H) 6.3 (s, 1 H) 7.8 (m, 3 H) 8.3 (d, 1H) 8.5 (s, 1H) 9.2 (s, 1H) 9.3 (s, 1H)

Preparation 38

4-Bromobenzyl 5-amino-1-ethyl-6-oxo-1,6-dihydropyridazine-3-carboxylate

A mixture of the title compound of Preparation 5 (0.5 g, 2.73 mmol), 4-bromobenzyl bromide (819 mg, 3.27 mmol) and potassium carbonate (377 mg, 2.73 mmol) in dimethylformamide (30 ml) was heated at 50° C. for 24 h. Once the solvent was evaporated under reduced pressure, the residue was purified through a flash chromatography column (2:3 hexane/ethyl acetate as eluent) to yield 0.82 g of the desired final compound. Yield=86%

$\delta$ (CDCl$_3$): 1.4 (t, J=7.3 Hz, 3 H) 4.3 (q, J=7.1 Hz, 2 H) 5.0 (s, 2 H) 5.3 (s, 2 H) 6.9 (s, 1 H) 7.3 (d, J=8.5 Hz, 2 H) 7.5 (d, J=8.5 Hz, 2 H)

Preparation 39

2-Chlorobenzyl 5-amino-1-ethyl-6-oxo-1,6-dihydropyridazine-3-carboxylate

A mixture of the title compound of Preparation 5 (0.5 g, 2.73 mmol), 2-chlorobenzyl bromide (425 µl, 3.27 mmol) and potassium carbonate (377 mg, 2.73 mmol) in dimethylformamide (30 ml) was heated at 50° C. for 24 h. Once the solvent was evaporated under reduced pressure, the residue was purified through a flash chromatography column (1:1 hexane/ethyl acetate as eluent) to yield 0.60 g of the desired final compound. Yield=71%

$\delta$ (CDCl$_3$): 1.4 (t, J=7.3 Hz, 3 H) 4.3 (q, J=7.1 Hz, 2 H) 5.0 (s, 2 H) 5.5 (s, 2 H) 6.9 (s, 1 H) 7.4 (m, 4 H)

Preparation 40

3-Methylbenzyl 5-amino-1-ethyl-6-oxo-1,6-dihydropyridazine-3-carboxylate

A mixture of the title compound of Preparation 5 (0.5 g, 2.73 mmol), 2-methylbenzyl chloride (361 µl, 2.73 mmol) and potassium carbonate (377 mg, 2.73 mmol) in dimethylformamide (30 ml) was heated at 50° C. for 24 h. Once the solvent was evaporated under reduced pressure, the residue was purified through a flash chromatography column (1:1 hexane/ethyl acetate as eluent) to yield 0.12 g of the desired final compound. Yield=16%.

$\delta$ (CDCl$_3$): 1.4 (t, J=7.1 Hz, 3 H) 2.4 (s, 3 H) 4.3 (q, J=7.1 Hz, 2 H) 5.0 (s, 2 H) 5.3 (s, 2 H) 6.9 (s, 1 H) 7.2 (m, 4 H)

Preparation 41

3-Trifluoromethylbenzyl 5-amino-1-ethyl-6-oxo-1,6-dihydropyridazine-3-carboxylate

A mixture of the title compound of Preparation 5 (0.5 g, 2.73 mmol), 3-trifluoromethylbenzyl bromide (417 µl, 2.73 mmol) and potassium carbonate (377 mg, 2.73 mmol) in dimethylformamide (30 ml) was heated at 50° C. for 24 h. Once the solvent was evaporated under reduced pressure, the residue was purified through a flash chromatography column (1:1 hexane/ethyl acetate as eluent) to yield 0.74 g of the desired final compound. Yield=79%.

$\delta$ (CDCl$_3$): 1.4 (t, J=7.3 Hz, 3 H) 4.3 (q, J=7.3 Hz, 2 H) 5.1 (s, 2 H) 5.4 (s, 2 H) 6.9 (s, 1 H) 7.5 (d, J=7.4 Hz, 1 H) 7.6 (m, 2 H) 7.7 (s, 1 H)

Preparation 42

3-Cyanobenzyl 5-amino-1-ethyl-6-oxo-1,6-dihydropyridazine-3-carboxylate

A mixture of the title compound of Preparation 5 (0.3 g, 1.64 mmol), 3-cyanobenzyl bromide (385 mg, 1.96 mmol) and potassium carbonate (226 mg, 1.64 mmol) in dimethylformamide (20 ml) was heated at 50° C. for 24 h. Once the solvent was evaporated under reduced pressure, the residue was purified through a flash chromatography column (2:1 to 1:1 hexane/ethyl acetate as eluent) to yield 391 mg of the desired final compound.

Yield=80%.

LRMS: m/Z 299 (M+1)$^+$

Preparation 43

4-Methoxybenzyl 5-amino-1-ethyl-6-oxo-1,6-dihydropyridazine-3-carboxylate

A mixture of the title compound of Preparation 5 (0.3 g, 1.64 mmol), 4-methoxybenzyl chloride (666 µl, 4.91 mmol) and potassium carbonate (226 mg, 1.64 mmol) in dimethylformamide (20 ml) was heated at 50° C. for 24 h. Once the solvent was evaporated under reduced pressure, the residue was purified through a flash chromatography column (1:1 hexane/ethyl acetate as eluent) to yield 180 mg of the desired final compound. Yield=36%.

δ (CDCl₃): 1.4 (t, J=7.1 Hz, 3 H) 3.8 (s, 3 H) 4.3 (q, J=7.1 Hz, 2 H) 5.0 (s, 2 H) 5.3 (s, 2 H) 6.9 (m, 3 H) 7.4 (d, J=8.5 Hz, 2 H)

Preparation 44

(S)-2-tert-butoxycarbonylamino-4-methyl-pentanoyloxymethyl 1-ethyl-5-(isoquinolin-4-ylamino)-6-oxo-1,6-dihydropyridazine-3-carboxylate The title compound of Preparation 37 (200 mg, 0.64 mmol), chloromethyl 2-tert-butoxycarbonylamino-4-methylpentanoate (540 mg, 1.93 mmol) and potassium carbonate (89 mg, 0.64 mmol) were suspended in dimethylformamide (5 ml) and heated overnight at 50° C. The solvent was evaporated under reduced pressure and the residue was passed through a silica-gel column, eluting with hexane/ethyl acetate 1:1, to yield 319 mg of the desired final product. Yield=87%.

δ (DMSO-d₆): 0.8 (dd, J=15.3, 6.7 Hz, 6 H) 1.2 (s, 2 H) 1.3 (s, 9 H) 1.4 (t, J=7.0 Hz, 3 H) 1.5 (m, 2H) 3.9 (m, 1 H) 4.3 (q, J=7.0 Hz, 2 H) 5.8 (d, J=5.9 Hz, 1 H) 5.9 (d, J=6.3 Hz, 1 H) 6.2 (s, 1 H) 7.3 (d, J=7.4 Hz, 1 H) 7.8 (m, 2 H) 8.3 (d, J=7.8 Hz, 1 H) 8.5 (s, 1 H) 9.3 (m, 2 H)

Preparation 45

1,3,3-Trimethylbutyl 4-acetyl-5-amino-1-ethyl-6-oxo-1,6-dihydropyridazine-3-carboxylate Obtained (50%) from the title compound from Preparation 16 and 4,4-dimethyl -2-pentanol following the experimental procedure described in Preparation 27.

LRMS: m/Z 324 (M+1)+.

δ (CDCl₃): 1.0 (s, 9 H) 1.4 (m, 6 H) 1.5 (m, 1 H) 1.8 (m, 1 H) 2.4 (s, 3 H) 4.2 (q, 2 H) 5.3 (m, 1 H) 7.4 (br.s, 2 H).

Preparation 46

3-Chlorobenzyl 4-acetyl-5-amino-1-ethyl-6-oxo-1,6-dihydropyridazine-3-carboxylate Obtained (47%) from the title compound from Preparation 16 and 3-chlorobenzyl bromide following the experimental procedure described in Preparation 17.

LRMS: m/Z 350 (M+1)+.

δ (CDCl₃): 1.4 (t, 3 H) 2.2 (s, 3 H) 4.2 (q, 2 H) 5.4 (s, 2 H) 7.3 (m, 2 H) 7.5 (br s, 2 H).

Preparation 47

3-Methoxybenzyl 4-acetyl-5-amino-1-ethyl-6-oxo-1,6-dihydropyridazine-3-carboxylate Obtained (37%) from the title compound from Preparation 16 and 3-methoxybenzyl chloride following the experimental procedure described in Preparation 17.

δ (CDCl₃): 1.4 (t, 3 H) 2.2 (s, 3 H) 3.8 (s, 3 H) 4.2 (q, 2 H) 5.4 (s, 2 H) 6.9 (m, 1 H) 7.0 (m, 2 H) 7.3 (m, 1H) 7.5 (br.s, 2 H).

Preparation 48

Octyl 4-acetyl-5-amino-1-ethyl-6-oxo-1,6-dihydropyridazine-3-carboxylate

Obtained (94%) as described in Preparation 18 but using 1-bromooctane instead of ethyl bromide.

δ(CDCl₃): 0.9 (m, 3 H) 1.2 (m, 10 H) 1.4 (t, 3 H) 1.8 (m, 2 H) 2.3 (s, 3 H) 4.2 (q, 2 H) 4.4 (t, 2 H) 7.5 (br.s, 2 H)

Preparation 49

(4E)-1,5-Dimethylhept-4-en-1-yl 4-acetyl-5-amino-1-ethyl-6-oxo-1,6-dihydropyridazine-3-carboxylate Obtained (75%) as described in Preparation 27 but using 6-methylhept-5-en-2-ol instead of isopropanol.

δ(CDCl₃): 0.4 (m, 6 H) 0.6 (m, 4 H) 0.7 (m, 3 H) 0.8 (m, 1 H) 2.1 (m, 2 H) 2.4 (s, 3 H) 4.2 (q, 2 H) 5.2 (m, 2 H) 7.5 (br.s, 2 H)

Preparation 50

Allyl 4-acetyl-5-amino-1-ethyl-6-oxo-1,6-dihydropyridazine-3-carboxylate

Obtained (42%) as described in Preparation 18 but using 3-bromoprop-1-ene instead of ethyl bromide.

δ(CDCl₃): 1.4 (t, 3 H) 2.4 (s, 3 H) 4.2 (q, 2 H) 4.8 (d, 2 H) 5.38 (d,d, 1 H) 5.42 (d,d, 1 H) 6.0 (m, 1 H) 7.5 (br.s, 2 H)

EXAMPLES

In the following tables some acronyms have been used with the following meanings:

| Acronym | Meaning |
| --- | --- |
| Et | Ethyl |
| iPr | Isopropyl |
| Bn | Benzyl |
| Ac | Acetyl |
| Me | Methyl |
| cHex | Cyclohexyl |
| t-Bu | tert-Butyl |

TABLE 2

| Example | R1 | R2 | R3 | R4 |
| --- | --- | --- | --- | --- |
| 1 | Et | 4-methyl-pyridin-3-yl | H | Bn |

TABLE 2-continued
| Example | R1 | R2 | R3 | R4 |
|---------|----|----|----|----|
| 2 | Et | 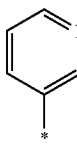 | H | Et |
| 3 | Et | 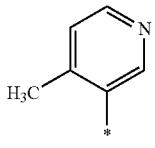 | H | Et |
| 4 | Et | 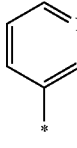 | H | iPr |
| 5 | Et | 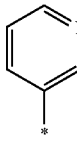 | H | 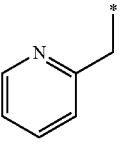 |
| 6 | Et | 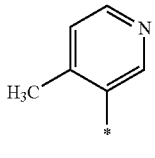 | H | iPr |
| 7 | Et | 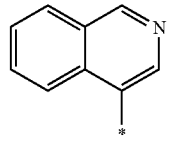 | H | Et |
| 8 | Et | 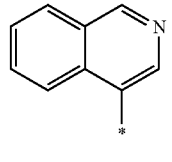 | H | iPr |
| 9 | Et | 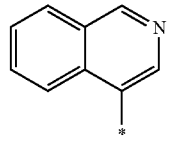 | H | 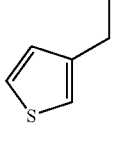 |
| 10 | Et | 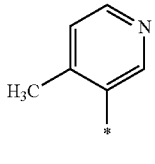 | H | 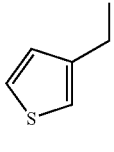 |
| 11 | Et | 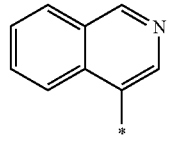 | H | 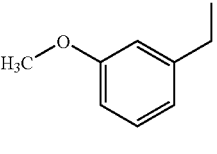 |

TABLE 2-continued
| Example | R1 | R2 | R3 | R4 |
|---------|----|----|----|----|
| 12 | Et | 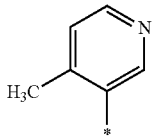 | H | 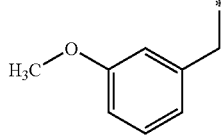 |
| 13 | Et | 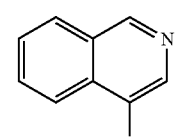 | H | 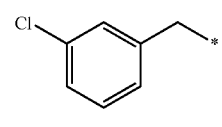 |
| 14 | Et | 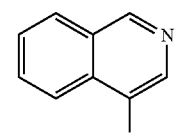 | H | 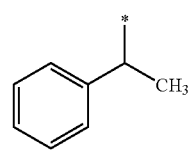 |
| 15 | Et | 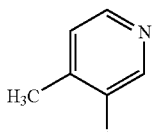 | H | 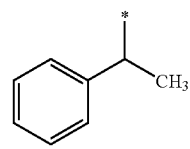 |
| 16 | Et | 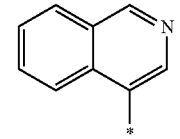 | H | 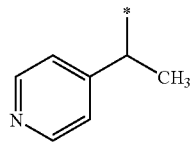 |
| 17 | Et | 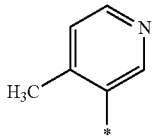 | H | 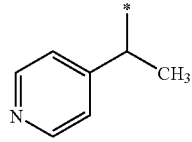 |
| 18 | Et | 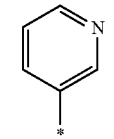 | H | 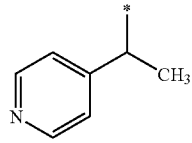 |
| 19 | Et | 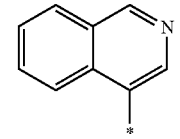 | H | 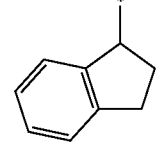 |
| 20 | Et | 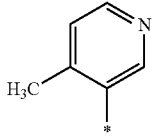 | H | 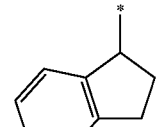 |
| 21 | Et | 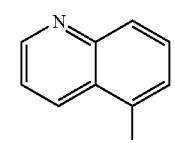 | Ac | Et |

TABLE 2-continued
| Example | R1 | R2 | R3 | R4 |
|---|---|---|---|---|
| 22 | Et | 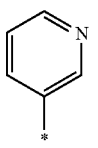 | Ac | Et |
| 23 | Et | 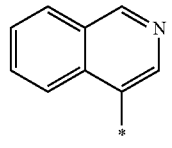 | Ac | Et |
| 24 | Et | 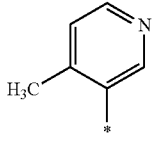 | Ac | Et |
| 25 | Et | 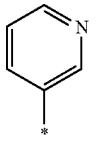 | Ac | iPr |
| 26 | Et | 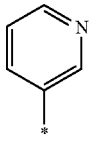 | Ac | Bn |
| 27 | Et | 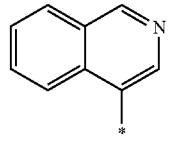 | Ac | iPr |
| 28 | Et | 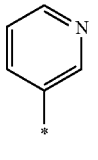 | Ac | 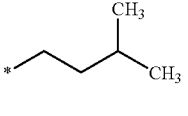 |
| 29 | Et | 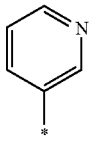 | Ac | 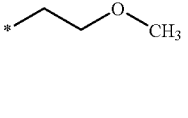 |
| 30 | Et | 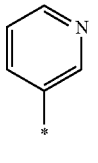 | Ac | 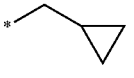 |
| 31 | Et | 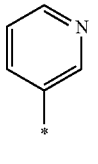 | Ac | Me |

TABLE 2-continued
| Example | R1 | R2 | R3 | R4 |
|---|---|---|---|---|
| 32 | Et | 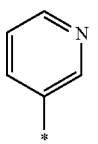 | Ac | 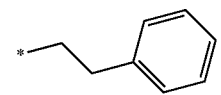 |
| 33 | Et | 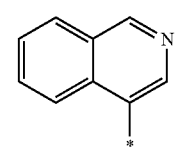 | Ac | Bn |
| 34 | Et | 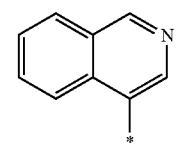 | Ac | cHex |
| 35 | Et | 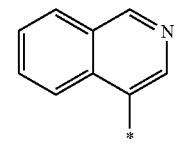 | Ac | t-Bu |
| 36 | Et | 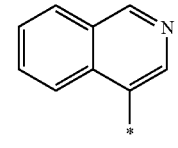 | Ac | 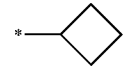 |
| 37 | Et | 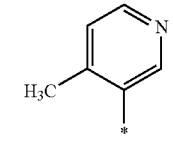 | Ac | cHex |
| 38 | Et | 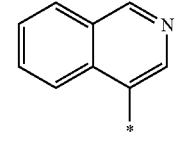 | Ac | 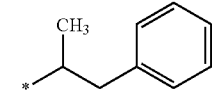 |
| 38 | Et | 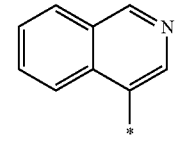 | Ac | 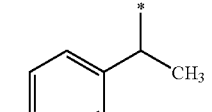 |
| 40 | Et | 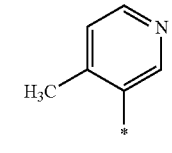 | Ac | t-Bu |
| 41 | Et | 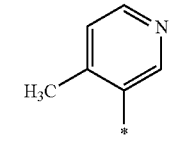 | Ac | 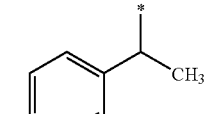 |

TABLE 2-continued
| Example | R1 | R2 | R3 | R4 |
|---------|----|----|----|----|
| 42 | Et |  | Ac |  |
| 43 | Et |  | Ac |  |
| 44 | Et | 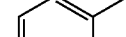 | Ac | 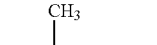 |
| 45 | Et | 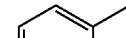 | H | Bn |
| 46 | Et | 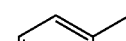 | H |  |
| 47 | Et | 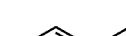 | H |  |
| 48 | Et |  | H |  |
| 49 | Et |  | H |  |
| 50 | Et |  | H |  |
| 51 | Et |  | H |  |

TABLE 2-continued
| Example | R1 | R2 | R3 | R4 |
|---|---|---|---|---|
| 52 | Et | 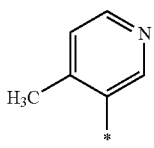 | H | 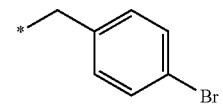 |
| 53 | Et | 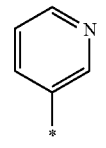 | H | 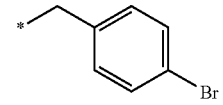 |
| 54 | Et | 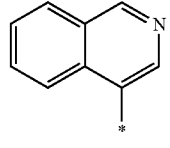 | H | 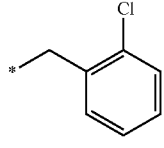 |
| 55 | Et | 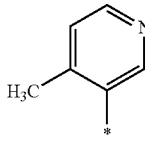 | H | 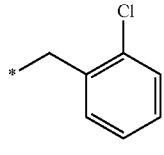 |
| 56 | Et | 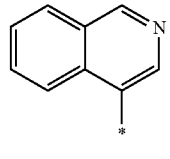 | H | 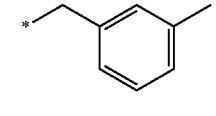 |
| 57 | Et | 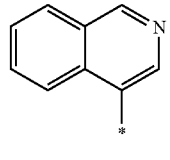 | H | 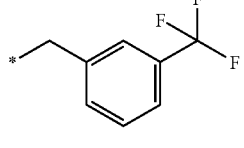 |
| 58 | Et | 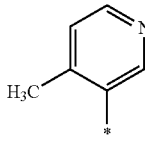 | H | 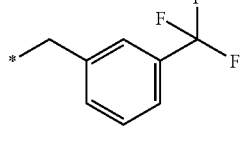 |
| 59 | Et | 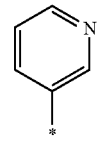 | H | 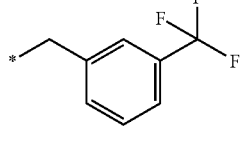 |
| 60 | Et | 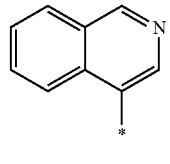 | H | 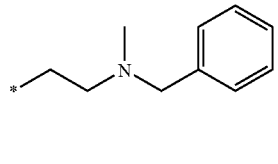 |
| 61 | Et | 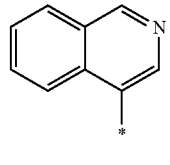 | H | 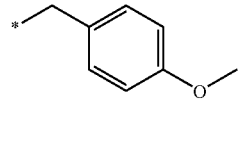 |

TABLE 2-continued
| Example | R1 | R2 | R3 | R4 |
|---|---|---|---|---|
| 62 | Et | 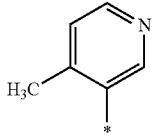 | H | 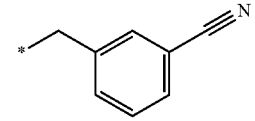 |
| 63 | Et | 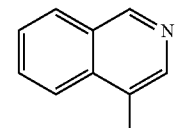 | H | 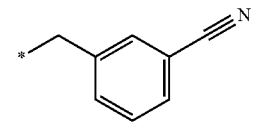 |
| 64 | Et | 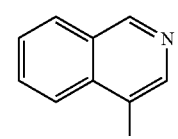 | H | 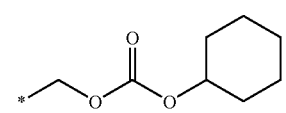 |
| 65 | Et | 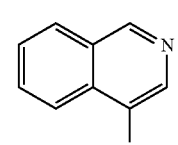 | H | 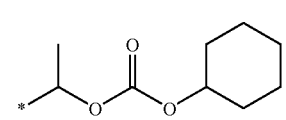 |
| 66 | Et | 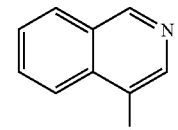 | H | 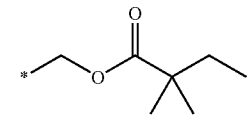 |
| 67 | Et | 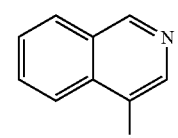 | H | 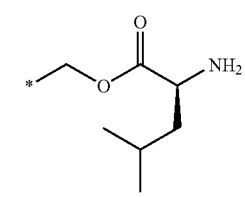 |
| 68 | Et | 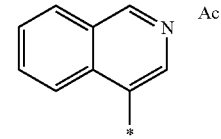 | Ac | 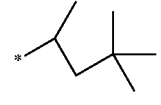 |
| 69 | Et | 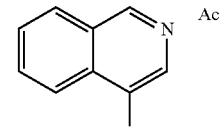 | Ac | 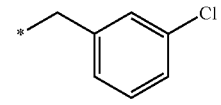 |
| 70 | Et | 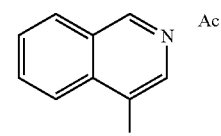 | Ac | 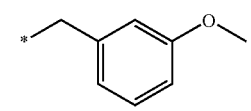 |

TABLE 2-continued

| Example | R1 | R2 | R3 | R4 |
|---|---|---|---|---|
| 71 | Et | isoquinolin-4-yl | Ac | n-octyl (*-CH₂(CH₂)₆CH₃) |
| 72 | Et | isoquinolin-4-yl | Ac | *-CH₂CH(CH₃)CH₂CH₂CH=C(CH₃)₂ |
| 73 | Et | isoquinolin-4-yl | Ac | allyl (*-CH₂CH=CH₂) |

EXAMPLES

Example 1

Benzyl 1-ethyl-5-(4-methylpyridin-3-ylamino)-6-oxo-1,6-dihydropyridazine-3-carboxylate A mixture of the title compound of Preparation 6 (0.30 g, 1.10 mmol), 3-bromo-4-methylpyridine (0.15 mL, 1.32 mmol), copper(I) iodide (21 mg, 0.11 mmol), potassium carbonate (0.32 g, 2.31 mmol) and 1,1'-dimethylethylenediamine (0.023 mL, 0.22 mmol) in dioxane (2 mL) are heated at 120° C. in a sealed tube under nitrogen for 48 h. Once at room temperature, the inorganic salts are filtered and the solvent evaporated under reduced pressure. Purification of the residue through a flash chromatography column eluting with 2:1 hexane/ethyl acetate to 1:1 yields 80 mg of the desired final compound. Yield=20%.

δ (CDCl$_3$): 1.5 (t, J=7.3 Hz, 3 H) 2.3 (s, 3 H) 4.4 (q, J=7.3 Hz, 2 H) 5.4 (s, 2 H) 6.8 (s, 1 H) 7.2 (d, J=5.0 Hz, 1 H) 7.4 (m, 6 H) 8.4 (d, J=4.6 Hz, 1 H) 8.6 (s, 1 H)

m.p. 137.4-138.1° C.

Example 2

Ethyl 1-ethyl-5-(pyridin-3-ylamino)-6-oxo-1,6-dihydropyridazine-3-carboxylate

A mixture of the title compound of Preparation 7 (0.21 g, 0.99 mmol), 3-bromopyridine (0.12 mL, 1.19 mmol), copper(I)iodide (19 mg, 0.10 mmol), potassium carbonate (0.29 g, 2.09 mmol) and 1,1'-dimethylethylenediamine (0.021 mL, 0.20 mmol) in dioxane (2 mL) are heated at 120° C. in a sealed tube under nitrogen for 48 h. Once at room temperature, the inorganic salts are filtered and the solvent evaporated under reduced pressure. Purification of the residue through a flash chromatography column eluting with 2:1 hexane/ethyl acetate to 1:1 yields 97 mg of the desired final compound. Yield=34%.

δ (CDCl$_3$): 1.4 (t, J=7.0 Hz, 3 H) 1.5 (t, J=7.3 Hz, 3 H) 4.4 (q, J=7.3 Hz, 2 H) 4.4 (q, J=7.0 Hz, 2 H) 7.3 (s, 1 H) 7.4 (dd, J=7.9, 4.6 Hz, 1 H) 7.6 (m, 2 H) 8.5 (d, J=6.2 Hz, 1 H) 8.6 (d, J=2.5 Hz, 1 H)

m.p. 166.1-166.9° C.

Example 3

Ethyl 1-ethyl-5-(4-methylpyridin-3-ylamino)-6-oxo-1,6-dihydropyridazine-3-carboxylate Obtained as a solid (37%) from the title compound of Preparation 7 and the corresponding bromide following the procedure of Example 1.

δ (CDCl$_3$): 1.4 (t, J=7.0 Hz, 3 H) 1.5 (t, J=7.3 Hz, 3 H) 2.3 (s, 3 H) 4.4 (m, 4 H) 6.9 (s, 1 H) 7.3 (m, 2 H) 8.4 (d, J=5.0 Hz, 1 H) 8.6 (s, 1 H)

m.p. 186.6-187.3° C.

Example 4

Isopropyl 1-ethyl-5-(pyridin-3-ylamino)-6-oxo-1,6-dihydropyridazine-3-carboxylate Obtained as a solid (23%) from the title compound of Preparation 8 and the corresponding bromide following the procedure of Example 2.

δ (CDCl$_3$): 1.4 (d, J=6.2 Hz, 6 H) 1.5 (t, J=7.3 Hz, 3 H) 4.4 (q, J=7.5 Hz, 2 H) 5.2 (m, 1 H) 7.3 (s, 1 H) 7.4 (dd, J=8.3, 4.6 Hz, 1 H) 7.6 (m, 2 H) 8.4 (d, J=5.0 Hz, 1 H) 8.6 (d, J=2.5 Hz, 1 H)

m.p. 131.8-133.1° C.

Example 5

Isopropyl 1-ethyl-5-(4-methylpyridin-3-ylamino)-6-oxo-1,6-dihydropyridazine-3-carboxylate Obtained as a solid (21%) from the title compound of Preparation 8 and the corresponding bromide following the procedure of Example 1.

δ (DMSO-d6): 1.2 (d, J=6.2 Hz, 6 H) 1.3 (t, J=7.0 Hz, 3 H) 2.2 (s, 3 H) 4.2 (q, J=7.0 Hz, 2H) 5.0 (m, 1 H) 6.3 (s, 1 H) 7.4 (d, J=5.0 Hz, 1 H) 8.4 (d, J=5.0 Hz, 1 H) 8.4 (s, 1 H) 8.8 (s, 1H)

m.p. 179.9-181.3° C.

Example 6

Pyridin-2-ylmethyl 1-ethyl-5-(pyridin-3-ylamino)-6-oxo-1,6-dihydropyridazine-3-carboxylate Obtained as a solid (16%) from the title compound of Preparation 9 and the corresponding bromide following the procedure of Example 2.

δ (CDCl$_3$): 1.5 (t, J=7.3 Hz, 3 H) 4.4 (t, J=7.5 Hz, 2 H) 5.5 (s, 2 H) 7.2 (m, 1 H) 7.4 (m, 2 H) 7.4 (d, J=7.9 Hz, 1 H) 7.6 (m, 2 H) 7.7 (m, 1 H) 8.4 (d, J=5.0 Hz, 1 H) 8.6 (m, 2 H)

m.p. 146.3-147.5° C.

Example 7

Isopropyl 1-ethyl-5-(isoquinolin-4-ylamino)-6-oxo-1,6-dihydropyridazine-3-carboxylate A mixture of the title compound of Preparation 8 (0.40 g, 1.78 mmol), 4-bromoisoquinoline (0.44 g, 2.13 mmol), copper(I)iodide (34 mg, 0.18 mmol), potassium carbonate (0.52 g, 3.73 mmol) and 1,1'-dimethylethylenediamine (0.038 mL, 0.36 mmol) in dioxane (2 mL) are heated at 120° C. in a sealed tube under nitrogen for 48 h. Once at room temperature, the inorganic salts are filtered and the solvent evaporated under reduced pressure. Purification of the residue through a flash chromatography column eluting with 2:1 hexane/ethyl acetate to 1:1 yields 99 mg of the desired final compound. Yield=28%.

δ (DMSO-d6): 1.2 (d, J=6.2 Hz, 6 H) 1.4 (t, J=7.3 Hz, 3 H) 4.3 (q, J=7.3 Hz, 2 H) 5.0 (m, 1 H) 6.3 (s, 1 H) 7.8 (m, 3 H) 8.3 (d, J=8.3 Hz, 1 H) 8.5 (s, 1 H) 9.3 (s, 1 H) 9.3 (s, 1 H)

m.p. 191.6-193.0° C.

Example 8

Ethyl 1-ethyl-5-(isoquinolin-4-ylamino)-6-oxo-1,6-dihydropyridazine-3-carboxylate Obtained as a solid (48%) from the title compound of Preparation 7 and the corresponding bromide following the procedure of Example 7.

δ (CDCl$_3$): 1.3 (t, J=7.0 Hz, 3 H) 1.5 (t, J=7.3 Hz, 3 H) 4.4 (q, J=7.0 Hz, 2 H) 4.4 (q, J=7.0 Hz, 2 H) 6.9 (s, 1 H) 7.7 (m, 2 H) 7.8 (m, 1 H) 7.9 (d, J=8.3 Hz, 1 H) 8.1 (d, J=7.9 Hz, 1 H) 8.7 (s, 1 H) 9.2 (s, 1 H)

m.p. 193.7-194.2° C.

Example 9

Thiophen-3-ylmethyl 1-ethyl-5-(isoquinolin-4-ylamino)-6-oxo-1,6-dihydropyridazine-3-carboxylate Obtained as a solid (16%) from the title compound of Preparation 10 and the corresponding bromide following the procedure of Example 7.

δ (DMSO-d6): 1.4 (t, J=7.0 Hz, 3 H) 4.2 (q, J=7.3 Hz, 2 H) 5.2 (s, 2 H) 6.3 (s, 1 H) 7.0 (d, J=5.0 Hz, 1 H) 7.5 (m, 1 H) 7.5 (dd, J=5.0, 2.9 Hz, 1 H) 7.8 (m, 3 H) 8.3 (d, J=7.9 Hz, 1 H) 8.5 (s, 1 H) 9.3 (s, 1 H) 9.3 (s, 1 H)

m.p. 154.3-154.9° C.

Example 10

Thiophen-3-ylmethyl 1-ethyl-5-(4-methylpyridin-3-ylamino)-6-oxo-1,6-dihydropyridazine-3-carboxylate Obtained as a solid (9%) from the title compound of Preparation 10 and the corresponding bromide following the procedure of Example 1.

δ (DMSO-d6): 1.3 (t, J=7.0 Hz, 3 H) 2.2 (s, 3 H) 4.2 (q, J=7.0 Hz, 2 H) 5.3 (s, 2 H) 6.3 (s, 1 H) 7.1 (d, J=5.0 Hz, 1 H) 7.4 (d, J=5.0 Hz, 1 H) 7.5 (m, 2 H) 8.4 (d, J=5.0 Hz, 1 H) 8.4 (s, 1 H) 8.9 (s, 1 H)

m.p. 141.7-142.9° C.

Example 11

3-Methoxybenzyl 1-ethyl-5-(isoquinolin-4-ylamino)-6-oxo-1,6-dihydropyridazine-3-carboxylate Obtained as a solid (26%) from the title compound of Preparation 11 and the corresponding bromide following the procedure of Example 7.

δ (DMSO-d6): 1.4 (t, J=7.0 Hz, 3 H) 3.7 (s, 3 H) 4.3 (q, J=7.3 Hz, 2 H) 5.2 (s, 2 H) 6.3 (s, 1 H) 6.9 (m, 3 H) 7.2 (dd, J=8.9, 7.7 Hz, 1 H) 7.8 (m, 3 H) 8.3 (d, J=7.9 Hz, 1 H) 8.5 (s, 1 H) 9.3 (m, 2 H)

m.p. 153.2-154.3° C.

Example 12

3-Methoxybenzyl 1-ethyl-5-(4-methylpyridin-3-ylamino)-6-oxo-1,6-dihydropyridazine-3-carboxylate Obtained as a solid (25%) from the title compound of Preparation 11 and the corresponding bromide following the procedure of Example 1.

δ (DMSO-d6): 1.3 (t, J=7.3 Hz, 3 H) 2.2 (s, 3 H) 3.7 (s, 3 H) 4.2 (q, J=7.3 Hz, 2 H) 5.2 (s, 2 H) 6.3 (s, 1 H) 6.9 (m, 3 H) 7.3 (t, J=8.1 Hz, 1 H) 7.4 (d, J=4.6 Hz, 1 H) 8.4 (d, J=5.0 Hz, 1 H) 8.4 (s, 1 H) 8.9 (s, 1 H)

m.p. 118.5-119.4° C.

Example 13

3-Chlorobenzyl 1-ethyl-5-(isoquinolin-4-ylamino)-6-oxo-1,6-dihydropyridazine-3-carboxylate Obtained as a solid (18%) from the title compound of Preparation 12 and the corresponding bromide following the procedure of Example 7.

δ (DMSO-d6): 1.4 (t, J=7.3 Hz, 3 H) 4.3 (q, J=7.0 Hz, 2 H) 5.2 (s, 2 H) 6.3 (s, 1 H) 7.2 (m, 1 H) 7.4 (m, 3 H) 7.8 (m, 3 H) 8.3 (d, J=7.9 Hz, 1 H) 8.5 (s, 1 H) 9.3 (s, 2 H)

m.p. 147.6-148.4° C.

Example 14

1-Phenylethyl 1-ethyl-5-(isoquinolin-4-ylamino)-6-oxo-1,6-dihydropyridazine-3-carboxylate Obtained as a solid (37%) from the title compound of Preparation 13 and the corresponding bromide following the procedure of Example 7.

δ (DMSO-d6): 1.4 (t, J=7.3 Hz, 3 H) 1.5 (d, J=6.6 Hz, 3 H) 4.3 (q, J=7.3 Hz, 2 H) 5.9 (q, J=6.6 Hz, 1 H) 6.3 (s, 1 H) 7.3 (m, 5 H) 7.8 (m, 3 H) 8.3 (d, J=7.9 Hz, 1 H) 8.5 (s, 1 H) 9.3 (s, 1 H) 9.3 (s, 1 H)

m.p. 166.7-167.6° C.

Example 15

1-Phenylethyl 1-ethyl-5-(4-methylpyridin-3-ylamino)-6-oxo-1,6-dihydropyridazine-3-carboxylate Obtained as a solid (37%) from the title compound of Preparation 13 and the corresponding bromide following the procedure of Example 1.

δ (DMSO-d6): 1.3 (t, J=7.0 Hz, 3 H) 1.5 (d, J=6.6 Hz, 3 H) 2.2 (s, 3 H) 4.2 (q, J=7.2 Hz, 2 H) 6.0 (q, J=6.4 Hz, 1 H) 6.3 (s, 1 H) 7.3 (m, 6 H) 8.4 (d, J=5.0 Hz, 1 H) 8.4 (s, 1 H) 8.9 (s, 1H)

m.p. 170.3-171.3° C.

Example 16

1-Pyridin-4-ylethyl 1-ethyl-5-(isoquinolin-4-ylamino)-6-oxo-1,6-dihydropyridazine-3-carboxylate Obtained as a solid (32%) from the title compound of Preparation 14 and the corresponding bromide following the procedure of Example 7.

δ (DMSO-d6): 1.4 (t, J=7.3 Hz, 3 H) 1.5 (d, J=6.6 Hz, 3 H) 4.3 (q, J=7.3 Hz, 2 H) 5.9 (q, J=6.6 Hz, 1 H) 6.3 (s, 1 H) 7.2 (m, 2 H) 7.8 (m, 3 H) 8.3 (d, J=7.9 Hz, 1 H) 8.5 (m, 3 H) 9.3 (m, 2 H)

m.p. 186.9-187.7° C.

Example 17

1-Pyridin-4-ylethyl 1-ethyl-5-(4-methylpyridin-3-ylamino)-6-oxo-1,6-dihydropyridazine-3-carboxylate Obtained as a solid (26%) from the title compound of Preparation 14 and the corresponding bromide following the procedure of Example 1.

δ (DMSO-d6): 1.4 (t, J=7.0 Hz, 3 H) 1.5 (d, J=6.6 Hz, 3 H) 2.2 (s, 3 H) 4.2 (q, J=7.0 Hz, 2 H) 5.9 (q, J=6.6 Hz, 1 H) 6.3 (s, 1 H) 7.4 (m, 2 H) 7.4 (d, J=5.0 Hz, 1 H) 8.4 (d, J=5.0 Hz, 1 H) 8.4 (s, 1 H) 8.6 (m, 2 H) 8.9 (s, 1 H).

m.p. 167.6-168.8° C.

Example 18

1-Pyridin-4-ylethyl 1-ethyl-5-(pyridin-3-ylamino)-6-oxo-1,6-dihydropyridazine-3-carboxylate Obtained as a solid (27%) from the title compound of Preparation 14 and the corresponding bromide following the procedure of Example 2.

δ (DMSO-d6): 1.4 (t, J=7.0 Hz, 3 H) 1.6 (d, J=6.7 Hz, 3 H) 4.2 (q, J=7.0 Hz, 2 H) 6.0 (q, J=6.7 Hz, 1 H) 7.1 (s, 1 H) 7.4 (m, 2 H) 7.5 (dd, J=8.4, 4.5 Hz, 1 H) 7.8 (m, 1 H) 8.4 (dd, J=4.7, 1.2 Hz, 1 H) 8.6 (m, 2 H) 8.6 (d, J=2.7 Hz, 1 H) 9.2 (s, 1 H)

m.p. 98.8-99.9° C.

Example 19

Indan-1-yl 1-ethyl-5-(4-methylpyridin-3-ylamino)-6-oxo-1,6-dihydropyridazine-3-carboxylate Obtained as a solid (7%) from the title compound of Preparation 15 and the corresponding bromide following the procedure of Example 1.

δ (DMSO-d6): 1.3 (t, J=7.0 Hz, 3 H) 2.0 (m, 1 H) 2.9 (m, 2 H) 4.2 (q, J=7.1 Hz, 2 H) 6.2 (m, 1 H) 6.3 (s, 1 H) 7.2 (m, 4 H) 7.8 (m, 3 H) 8.2 (d, J=7.9 Hz, 1 H) 8.5 (s, 1 H) 9.3 (m, 2 H)

m.p. 174.9-176.2° C.

Example 20

Indan-1-yl 1-ethyl-5-(isoquinolin-4-ylamino)-6-oxo-1,6-dihydropyridazine-3-carboxylate Obtained as a solid (18%) from the title compound of Preparation 15 and the corresponding bromide following the procedure of Example 7.

δ (DMSO-d6): 1.3 (t, J=7.3 Hz, 3 H) 2.0 (m, 1 H) 2.2 (s, 3 H) 2.9 (m, 1 H) 3.0 (m, 1 H) 4.2 (q, J=7.0 Hz, 2 H) 6.3 (dd, J=7.0, 4.1 Hz, 1 H) 6.3 (s, 1 H) 7.2 (m, 1 H) 7.3 (m, 4 H) 8.4 (d, J=5.0 Hz, 1 H) 8.4 (s, 1 H) 8.8 (s, 1 H)

m.p. 180.2-182.1° C.

Example 21

Ethyl 4-acetyl-1-ethyl-6-oxo-5-(quinolin-5-ylamino)-1,6-dihydropyridazine-3-carboxylate A mixture of the title compound of Preparation 4 (500 mg, 1.97 mmol), 5-quinolinboronic acid (560 mg, 4.0 mmol), anhydrous cupric acetate (683 mg, 3.95 mmol), triethylamine (0.40 g, 3.95 mmol) and activated molecular sieves (1.46 g, 4 Å) in dry dichloromethane (25 mL) was stirred under air exposure at room temperature for 48 h. The reaction was filtered and the solvent removed under reduced pressure. The resulting residue was purified by column chromatography (53% yield).

LRMS: m/Z 381 (M+1)$^+$.

δ (DMSO-d6): 1.4 (t, J=7.3 Hz, 3 H) 1.5 (s, 3 H) 4.2 (m, 4 H) 7.3 (d, J=7.3 Hz, 1 H) 7.6 (dd, J=8.4, 4.1 Hz, 1 H) 7.6 (dd, 1 H) 7.9 (d, J=8.6 Hz, 1 H) 8.4 (d, 1 H) 8.9 (d, 1 H) 9.3 (s, 1H).

Example 22

Ethyl 4-acetyl-1-ethyl-6-oxo-5-(pyridin-3-ylamino)-1,6-dihydropyridazine-3-carboxylate Obtained as a solid (12.5%) from de title compound of Preparation 4 and the corresponding 3-bromopyridine following the procedure of Example 2.

LRMS: m/Z 331 (M+1)$^+$.

δ (DMSO-d6): 1.2 (t, J=7.2 Hz, 3 H) 1.3 (t, J=7.2 Hz, 3 H) 1.9 (s, 3 H) 4.2 (m, 4 H) 7.3 (m, 1 H) 7.4 (m, 1 H) 8.3 (m, 1 H) 8.3 (d, J=2.3 Hz, 1 H) 9.1 (s, 1 H).

Example 23

Ethyl 4-acetyl-1-ethyl-5-(isoquinolin-4-ylamino)-6-oxo-1,6-dihydropyridazine-3-carboxylate Obtained as a solid (11%) from de title compound of Preparation 4 and the corresponding 4-bromoisoquinoline following the procedure of Example 7.

LRMS: m/Z 381 (M+1)$^+$.

δ (DMSO-d6): 1.2 (t, J=7.2 Hz, 3 H) 1.4 (t, J=7.2 Hz, 3 H) 1.6 (s, 3 H) 4.2 (m, 4 H) 7.7 (dd, 1 H) 7.8 (dd, 1 H) 8.0 (d, 1 H) 8.2 (d, 1 H) 8.3 (s, 1 H) 9.2 (m, 1 H).

Example 24

Ethyl 4-acetyl-1-ethyl-5-[(4-methylpyridin-3-yl)amino]-6-oxo-1,6-dihydropyridazine-3-carboxylate Obtained as a solid (6%) from de title compound of Preparation 4 and the corresponding 3-bromo-4-methyl-pyridine following the procedure of Example 1. The product was purified by preparative HPLC/MS.
LRMS: m/Z 345 (M+1)+.
δ (DMSO-d6): 1.2 (t, J=7.2 Hz, 3 H) 1.3 (t, J=7.0 Hz, 3 H) 1.7 (s, 3 H) 2.2 (s, 3 H) 4.2 (m, 5 H) 7.3 (d, J=4.7 Hz, 1 H) 8.2 (s, 1 H) 8.3 (d, J=4.7 Hz, 1 H).

Example 25

Isopropyl 4-acetyl-1-ethyl-6-oxo-5-(pyridin-3-ylamino)-1,6-dihydropyridazine-3-carboxylate Obtained as a solid (14.5%) from de title compound of Preparation 32 and the corresponding boronic acid following the procedure of Example 21.
LRMS: m/Z 345 (M+1)+.
δ (DMSO-d6): 1.2 (m, 6 H) 1.25 (t, 3 H) 1.9 (s, 3 H) 4.2 (q, 2 H) 5.0 (m, 1 H) 7.3 (m, 1 H) 7.4 (m, 1 H) 8.3 (br.s, 2 H) 9.2 (s, 1 H).

Example 26

Benzyl 4-acetyl-1-ethyl-6-oxo-5-(pyridin-3-ylamino)-1,6-dihydropyridazine-3-carboxylate Obtained as a solid (20%) from de title compound of Preparation 19 and the corresponding boronic acid following the procedure of Example 21.
LRMS: m/Z 393 (M+1)+.
δ (DMSO-d6): 1.3 (t, J=7.0 Hz, 3 H) 1.9 (s, 3 H) 4.1 (q, J=7.0 Hz, 2 H) 5.2 (m, 2 H) 7.3 (m, 7 H) 8.3 (d, J=3.1 Hz, 1 H) 8.3 (d, J=2.3 Hz, 1 H) 9.1 (m, 1 H).

Example 27

Isopropyl 4-acetyl-1-ethyl-5-(isoquinolin-4-ylamino)-6-oxo-1,6-dihydropyridazine-3-carboxylate Obtained as a solid (5%) from de title compound of Preparation 32 and the corresponding boronic acid following the procedure of Example 21.
LRMS: m/Z 395 (M+1)+.
Retention Time: 13 min.

Example 28

3-Methylbutyl 4-acetyl-1-ethyl-6-oxo-5-(pyridin-3-ylamino)-1,6-dihydropyridazine-3-carboxylate Obtained as a solid (23.5%) from de title compound of Preparation 22 and the corresponding boronic acid following the procedure of Example 21.
LRMS: m/Z 373 (M+1)+.
δ (DMSO-d6): 0.9 (s, 3 H) 0.9 (s, 3 H) 1.3 (t, J=7.3 Hz, 3 H) 1.5 (q, J=7.0 Hz, 2 H) 1.7 (m, 1 H) 1.9 (s, 3 H) 4.15 (q, 2H) 4.2 (t, 2H) 7.3 (m, 1 H) 7.4 (d, J=8.3 Hz, 1 H) 8.3 (br.s, 1 H) 9.1 (s, 1 H)

Example 29

2-Methoxyethyl 4-acetyl-1-ethyl-6-oxo-5-(pyridin-3-ylamino)-1,6-dihydropyridazine-3-carboxylate Obtained as a solid (20%) from de title compound of Preparation 23 and the corresponding boronic acid following the procedure of Example 21.
LRMS: m/Z 361 (M+1)+.
δ (DMSO-d6): 1.3 (t, J=7.3 Hz, 3 H) 1.9 (s, 3 H) 3.3 (s, 3 H) 3.5 (m, 2 H) 4.2 (q, J=7.0 Hz, 2 H) 4.3 (m, 2 H) 7.3 (m, 1 H) 7.4 (m, 1 H) 8.3 (d, J=4.1 Hz, 1 H) 8.3 (d, J=2.1 Hz, 1 H) 9.1 (s, 1 H).

Example 30

Cyclopropylmethyl 4-acetyl-1-ethyl-6-oxo-5-(pyridin-3-ylamino)-1,6-dihydropyridazine-3-carboxylate Obtained as a solid (24%) from de title compound of Preparation 21 and the corresponding boronic acid following the procedure of Example 21.
LRMS: m/Z 357 (M+1)+.
δ (DMSO-d6): 0.3 (m, 2 H) 0.5 (m, 2 H) 1.1 (m, 1 H) 1.3 (t, J=7.1 Hz, 3 H) 1.9 (s, 3 H) 4.0 (d, J=7.5 Hz, 2 H) 4.2 (q, J=7.1 Hz, 2 H) 7.3 (m, 1 H) 7.4 (m, 1 H) 8.3 (m, 2 H) 9.1 (s, 1 H).

Example 31

Methyl 4-acetyl-1-ethyl-6-oxo-5-(pyridin-3-ylamino)-1,6-dihydropyridazine-3-carboxylate Obtained as a solid (16%) from de title compound of Preparation 20 and the corresponding boronic acid following the procedure of Example 21.
LRMS: m/Z 317 (M+1)+.
δ (DMSO-d6): 1.3 (t, J=7.2 Hz, 3 H) 1.9 (s, 3 H) 3.7 (s, 3 H) 4.1 (q, J=7.2 Hz, 2 H) 7.3 (dd, J=8.2, 4.7 Hz, 1 H) 7.4 (dd, J=8.2, 1.6 Hz, 1 H) 8.3 (m, 2 H) 9.1 (br.s, 1 H).

Example 32

2-Phenylethyl 4-acetyl-1-ethyl-6-oxo-5-(pyridin-3-ylamino)-1,6-dihydropyridazine-3-carboxylate Obtained as a solid (22%) from de title compound of Preparation 24 and the corresponding boronic acid following the procedure of Example 21.
LRMS: m/Z 407 (M+1)+.
δ (DMSO-d6): 1.3 (t, J=7.2 Hz, 3 H) 1.9 (s, 3 H) 2.9 (t, J=6.8 Hz, 2 H) 4.2 (q, J=7.2 Hz, 2 H) 4.4 (t, J=6.8 Hz, 2 H) 7.3 (m, 6 H) 7.4 (m, 1 H) 8.3 (m, J=9.5 Hz, 2 H) 9.1 (s, 1 H).

Example 33

Benzyl 4-acetyl-1-ethyl-5-(isoquinolin-4-ylamino)-6-oxo-1,6-dihydropyridazine-3-carboxylate Obtained as a solid (33%) from de title compound of Preparation 19 and the corresponding boronic acid following the procedure of Example 21.
LRMS: m/Z 443 (M+1)+.
δ (DMSO-d6): 1.4 (t, J=7.0 Hz, 3 H) 1.5 (s, 3 H) 4.2 (q, J=7.0 Hz, 2 H) 5.2 (m, 2 H) 7.3 (m, 5 H) 7.8 (m, 2 H) 8.0 (d, J=8.2 Hz, 1 H) 8.2 (d, J=7.8 Hz, 1 H) 8.3 (m, 1 H) 9.2 (m, 2 H).

Example 34

Cyclohexyl 4-acetyl-1-ethyl-5-(isoquinolin-4-ylamino)-6-oxo-1,6-dihydropyridazine-3-carboxylate Obtained as a solid (11%) from de title compound of Preparation 28 and the corresponding boronic acid following the procedure of Example 21.
LRMS: m/Z 435 (M+1)+.
δ (DMSO-d6): 1.4 (m, 13 H) 1.6 (s, 3 H) 4.2 (q, J=7.2 Hz, 2 H) 4.7 (m, 1 H) 7.7 (dd, 1 H) 7.8 (dd, 1 H) 8.0 (d, J=8.3 Hz, 1 H) 8.2 (d, J=8.3 Hz, 1 H) 8.3 (s, 1 H) 9.2 (m, 2 H).

Example 35 tert-Butyl 4-acetyl-1-ethyl-5-(isoquinolin-4-ylamino)-6-oxo-1,6-dihydropyridazine-3-carboxylate Obtained as a solid (16%) from de title compound of Preparation 34 and the corresponding boronic acid following the procedure of Example 21.
LRMS: m/Z 409 (M+1)+.
δ (DMSO-d6): 1.4 (t, J=7.3 Hz, 3 H) 1.4 (s, 9 H) 1.6 (s, 3 H) 4.2 (q, J=7.3 Hz, 2 H) 7.7 (dd, 1 H) 7.8 (dd, 1 H) 8.0 (d, J=8.3 Hz, 1 H) 8.2 (d, J=7.9 Hz, 1 H) 8.3 (s, 1 H) 9.2 (m, 2 H).

Example 36

Cyclobutyl 4-acetyl-1-ethyl-5-(isoquinolin-4-ylamino)-6-oxo-1,6-dihydropyridazine-3-carboxylate Obtained as a solid (5%) from de title compound of Preparation 27 and the corresponding boronic acid following the procedure of Example 21.
LRMS: m/Z 407 (M+1)+.
Retention Time: 14 min.

Example 37

Cyclohexyl 4-acetyl-1-ethyl-5-[(4-methylpyridin-3-yl)amino]-6-oxo-1,6-dihydropyridazine-3-carboxylate Obtained as a solid (18%) from de title compound of Preparation 28 and 3-bromo-4-methylpyridine following the procedure of Example 1.
LRMS: m/Z 399 (M+1)+.
δ (DMSO-d6): 1.2 (s, 2 H) 1.3 (m, 5 H) 1.4 (m, 2 H) 1.7 (m, 2 H) 1.7 (s, 3 H) 1.8 (m, 2 H) 2.2 (s, 3 H) 4.2 (q, J=7.3 Hz, 2 H) 4.8 (q, 1 H) 7.3 (d, J=5.0 Hz, 1 H) 8.2 (s, 1 H) 8.3 (d, J=5.0 Hz, 1 H) 8.8 (s, 1 H).

Example 38

1-Methyl-2-phenylethyl 4-acetyl-1-ethyl-5-(isoquinolin-4-ylamino)-6-oxo-1,6-dihydropyridazine-3-carboxylate Obtained as a solid (23%) from de title compound of Preparation 25 and the corresponding boronic acid following the procedure of Example 21.
LRMS: m/Z 471 (M+1)+.
δ (DMSO-d6): 1.2 (d, J=6.2 Hz, 3 H) 1.4 (t, J=7.0 Hz, 3 H) 1.5 (s, 3 H) 2.9 (m, 2 H) 4.2 (m, 2 H) 5.1 (m, 1 H) 7.2 (m, 5 H) 7.7 (dd, 1 H) 7.8 (dd, 1 H) 7.9 (d, J=7.5 Hz, 1 H) 8.2 (d, J=7.9 Hz, 1 H) 8.3 (s, 1 H) 9.2 (s, 2 H).

Example 39

1-Phenylethyl 4-acetyl-1-ethyl-5-(isoquinolin-4-ylamino)-6-oxo-1,6-dihydropyridazine-3-carboxylate Obtained as a solid (17%) from de title compound of Preparation 26 and the corresponding boronic acid following the procedure of Example 21.
LRMS: m/Z 457 (M+1)+.
δ (DMSO-d6): 1.4 (t, J=7.3 Hz, 3 H) 1.5 (m, 6 H) 4.2 (m, 2 H) 5.9 (q, J=6.5 Hz, 1 H) 7.3 (m, 5 H) 7.7 (dd, 1 H) 7.8 (dd, 1 H) 8.0 (d, J=7.5 Hz, 1 H) 8.2 (d, J=7.9 Hz, 1 H) 8.3 (s, 1 H) 9.2 (m, 2 H).

Example 40 tert-Butyl 4-acetyl-1-ethyl-5-[(4-methylpyridin-3-yl)amino]-6-oxo-1,6-dihydropyridazine-3-carboxylate Obtained as a solid (21%) from de title compound of Preparation 34 and 3-bromo-4-methylpyridine following the procedure of Example 1.
LRMS: m/Z 373 (M+1)+.
δ (DMSO-d6): 1.3 (t, J=7.1 Hz, 3 H) 1.4 (s, 9 H) 1.7 (s, 3 H) 2.2 (s, 3 H) 4.2 (q, J=7.1 Hz, 2 H) 7.2 (d, J=5.0 Hz, 1 H) 8.2 (s, 1 H) 8.3 (d, J=5.0 Hz, 1 H) 8.8 (s, 1 H).

Example 41

1-Phenylethyl 4-acetyl-1-ethyl-5-[(4-methylpyridin-3-yl)amino]-6-oxo-1,6-dihydropyridazine-3-carboxylate Obtained as a solid (9.6%) from de title compound of Preparation 26 and 3-bromo-4-methylpyridine following the procedure of Example 1.
LRMS: m/Z 421 (M+1)+.
δ (DMSO-d6): 1.3 (t, J=6.8 Hz, 3 H) 1.5 (d, J=6.7 Hz, 3 H) 1.7 (s, 3 H) 2.2 (s, 3 H) 4.2 (m, 2 H) 5.9 (q, J=6.8 Hz, 1 H) 7.2 (d, J=4.7 Hz, 1 H) 7.3 (m, 5 H) 8.2 (m, 1 H) 8.3 (m, J=3.9 Hz, 1 H) 8.8 (s, 1 H).

Example 42 sec-Butyl 4-acetyl-1-ethyl-5-(isoquinolin-4-ylamino)-6-oxo-1,6-dihydropyridazine-3-carboxylate Obtained as a solid (2%) from de title compound of Preparation 29 and the corresponding boronic acid following the procedure of Example 21. The product was purified by preparative HPLC/MS.
LRMS: m/Z 409 (M+1)+.
Retention Time: 15 min.

Example 43

2-(Dimethylamino)-2-oxoethyl 4-acetyl-1-ethyl-5-(isoquinolin-4-ylamino)-6-oxo-1,6-dihydropyridazine-3-carboxylate Obtained as a solid (1.5%) from de title compound of Preparation 17 and the corresponding boronic acid following the procedure of Example 21. The product was purified by preparative HPLC/MS.
LRMS: m/Z 438 (M+1)+.
Retention Time: 10 min.

Example 44

2-Methoxy-1-methyl-2-oxoethyl 4-acetyl-1-ethyl-5-(isoquinolin-4-ylamino)-6-oxo-1,6-dihydropyridazine-3-carboxylate Obtained as a solid (19%) from de title compound of Preparation 18 and the corresponding boronic acid following the procedure of Example 21.

LRMS: m/Z 439 (M+1)+.

δ (DMSO-d6): 1.4 (t, J=6.9 Hz, 3 H) 1.4 (d, J=7.0 Hz, 3 H) 1.6 (s, 3 H) 3.6 (s, 3 H) 4.2 (q, J=6.9 Hz, 2 H) 5.1 (q, J=7.0 Hz, 1 H) 7.7 (dd, 1 H) 7.8 (dd, 1 H) 7.9 (d, J=8.6 Hz, 1 H) 8.2 (d, J=8.2 Hz, 1 H) 8.3 (s, 1 H) 9.2 (m, 2 H).

Example 45

Benzyl 1-ethyl-5-(isoquinolin-4-ylamino)-6-oxo-1,6-dihydropyridazine-3-carboxylate A mixture of the title compound of Preparation 35 (330 mg, 1.0 mmol), 4-bromoisoquinoline (249 mg, 1.2 mmol), copper (I)iodide (19 mg, 0.10 mmol), potassium carbonate (0.29 g, 2.1 mmol) and 1,1'-dimethylethylenediamine (21 μl, 0.20 mmol) in dioxane (2 ml) are heated at 125° C. in a sealed tube under nitrogen for 48 h. Once at room temperature, the inorganic salts are filtered and the solvent evaporated under reduced pressure. Purification of the residue through a flash chromatography column eluting with 4:1 hexane/ethyl acetate to 1:1 yields 95 mg of the desired final compound. Yield=24%.

δ (DMSO-d$_6$): 1.4 (t, J=7.2 Hz, 3 H) 4.2 (q, J=7.2 Hz, 2 H) 5.2 (s, 2 H) 6.3 (s, 1 H) 7.3 (m, 5 H) 7.8 (m, 3 H) 8.3 (d, J=7.9 Hz, 1 H) 8.5 (s, 1 H) 9.3 (m, J=3.3 Hz, 2 H)

Example 46

Benzyloxycarbonylmethyl 1-ethyl-5-(isoquinolin-4-ylamino)-6-oxo-1,6-dihydropyridazine-3-carboxylate The title compound of Preparation 37 (80 mg, 0.26 mmol), benzyl bromoacetate (123 μl, 0.77 mmol) and potassium carbonate (36 mg, 0.26 mmol) are suspended in dimethylformamide (4 ml) and heated overnight at 50° C. The solvent is evaporated under reduced pressure and the residue is passed through a silica-gel column, eluting with hexane/ethyl acetate 1:1 to 2:3, to yield 34 mg of the desired final product. Yield=29%.

δ (DMSO-d$_6$): 1.4 (t, J=7.0 Hz, 3 H) 4.3 (q, J=7.3 Hz, 2 H) 4.9 (s, 2 H) 5.1 (s, 2 H) 6.2 (s, 1 H) 7.3 (m, 5 H) 7.8 (m, 3 H) 8.3 (d, J=7.9 Hz, 1 H) 8.5 (s, 1 H) 9.3 (m, 2 H)

Example 47

2-Oxo-2-phenyl-ethyl 1-ethyl-5-(isoquinolin-4-ylamino)-6-oxo-1,6-dihydropyridazine-3-carboxylate Obtained as a solid (71%) from the title compound of Preparation 37 and the corresponding bromide following the procedure of Example 46.

δ (DMSO-d$_6$): 1.4 (m, 3 H) 4.3 (q, J=7.2 Hz, 2 H) 5.6 (s, 2 H) 6.3 (s, 1 H) 7.5 (t, J=7.8 Hz, 2 H) 7.7 (m, 1 H) 7.7 (m, 1 H) 7.8 (m, 2 H) 7.9 (dd, J=8.2, 1.2 Hz, 2 H) 8.2 (d, J=7.8 Hz, 1 H) 8.5 (s, 1 H) 9.3 (s, 1 H) 9.3 (s, 1 H)

Example 48

Dimethylcarbamoylmethyl 1-ethyl-5-(isoquinolin-4-ylamino)-6-oxo-1,6-dihydropyridazine-3-carboxylate Obtained as a solid (30%) from the title compound of Preparation 37 and the corresponding chloride following the procedure of Example 46.

δ (DMSO-d$_6$): 1.4 (t, J=7.0 Hz, 3 H) 2.8 (s, 3 H) 2.9 (s, 3 H) 4.3 (q, J=7.0 Hz, 2 H) 4.9 (s, 2 H) 6.2 (s, 1 H) 7.8 (m, 1 H) 7.8 (m, J=4.1 Hz, 2 H) 8.3 (d, J=7.9 Hz, 1 H) 8.5 (s, 1 H) 9.3 (s, 1 H) 9.3 (s, 1 H)

Example 49

2-Phenoxyethyl 1-ethyl-5-(isoquinolin-4-ylamino)-6-oxo-1,6-dihydropyridazine-3-carboxylate Obtained as a solid (49%) from the title compound of Preparation 37 and the corresponding bromide following the procedure of Example 46.

δ (DMSO-d$_6$): 1.4 (t, J=7.3 Hz, 3 H) 4.2 (m, 2 H) 4.3 (q, J=7.0 Hz, 2 H) 4.5 (m, 2 H) 6.3 (s, 1 H) 6.8 (m, J=7.9 Hz, 2 H) 6.9 (t, J=7.5 Hz, 1 H) 7.3 (m, 2 H) 7.8 (m, 3 H) 8.2 (d, J=7.9 Hz, 1 H) 8.5 (s, 1 H) 9.3 (s, 1 H) 9.3 (s, 1 H)

Example 50

2-Dimethylaminoethyl 1-ethyl-5-(isoquinolin-4-ylamino)-6-oxo-1,6-dihydropyridazine-3-carboxylate The final product of Preparation 37 (80 mg, 0.26 mmol), dimethylaminoethanol (26 μl, 0.26 mmol), DEAD (40 μl, 0.26 mmol) and triphenylphosphine (68 mg, 0.26 mmol) are suspended in tetrahydrofurane (4 ml) and stirred overnight under inert atmosphere at room temperature. One more equivalent of dimethylaminoethanol, triphenylphosphine and DEAD are added and the reaction mixture is stirred for another 24 h. The solvent is evaporated under reduced pressure and the residue purified through a flash chromatography column, eluting with ethyl acetate first and then with AcOEt/MeOH 7:3. 74 mg of the desired final compound are obtained. Yield=76%.

δ (DMSO-d$_6$): 1.4 (m, 3 H) 2.0 (s, 6 H) 2.4 (t, J=5.5 Hz, 2 H) 4.2 (t, J=5.7 Hz, 2 H) 4.3 (q, J=7.0 Hz, 2 H) 6.2 (s, 1 H) 7.8 (m, 1 H) 7.8 (m, 2 H) 8.3 (d, J=7.8 Hz, 1 H) 8.5 (s, 1 H) 9.3 (s, 1 H) 9.3 (s, 1 H)

Example 51

4-Bromobenzyl 1-ethyl-5-(isoquinolin-4-ylamino)-6-oxo-1,6-dihydropyridazine-3-carboxylate Obtained as a solid (10%) from the title compound of Preparation 38 and the corresponding bromide following the procedure of Example 7.

δ (DMSO-d$_6$): 1.4 (t, J=7.3 Hz, 3 H) 4.2 (q, J=7.5 Hz, 2 H) 5.2 (s, 2 H) 6.3 (s, 1 H) 7.3 (d, J=8.3 Hz, 2 H) 7.5 (d, J=8.3 Hz, 2 H) 7.8 (m, 3 H) 8.3 (d, J=7.9 Hz, 1 H) 8.5 (s, 1 H) 9.3 (s, 2 H)

Example 52

4-Bromobenzyl 1-ethyl-5-(4-methyl-pyridin-3-ylamino)-6-oxo-1,6-dihydropyridazine-3-carboxylate Obtained as a solid (5%) from the title compound of Preparation 38 and the corresponding bromide following the procedure of Example 1.

δ (DMSO-$d_6$): 1.3 (t, J=7.3 Hz, 3 H) 2.2 (s, 3 H) 4.2 (q, J=7.2 Hz, 2 H) 6.3 (s, 2 H) 7.4 (m, 3 H) 7.6 (d, J=8.7 Hz, 2 H) 8.4 (m, 3 H) 8.9 (s, 1 H)

Example 53

4-Bromobenzyl 1-ethyl-6-oxo-5-(pyridin-3-ylamino)-1,6-dihydropyridazine-3-carboxylate Obtained as a solid (7%) from the title compound of Preparation 38 and the corresponding bromide following the procedure of Example 2.

δ (DMSO-$d_6$): 1.3 (t, J=7.2 Hz, 3 H) 4.2 (q, J=7.0 Hz, 2 H) 5.3 (s, 2 H) 7.1 (s, 1 H) 7.4 (m, 3 H) 7.6 (d, J=8.2 Hz, 2 H) 7.8 (d, J=8.2 Hz, 1 H) 8.4 (d, J=3.5 Hz, 1 H) 8.6 (d, J=2.3 Hz, 1 H) 9.2 (s, 1 H)

Example 54

2-Chlorobenzyl 1-ethyl-5-(isoquinolin-4-ylamino)-6-oxo-1,6-dihydropyridazine-3-carboxylate Obtained as a solid (16%) from the title compound of Preparation 39 and the corresponding bromide following the procedure of Example 7.

δ (DMSO-$d_6$): 1.4 (t, J=7.0 Hz, 3 H) 4.3 (q, J=7.0 Hz, 2 H) 5.3 (s, 2 H) 6.3 (s, 1 H) 7.4 (m, 3 H) 7.5 (m, 1 H) 7.8 (m, 3 H) 8.3 (d, J=7.8 Hz, 1 H) 8.5 (s, 1 H) 9.3 (m, 2 H)

Example 55

2-Chlorobenzyl 1-ethyl-5-(4-methyl-pyridin-3-ylamino)-6-oxo-1,6-dihydropyridazine-3-carboxylate Obtained as a solid (22%) from the title compound of Preparation 39 and the corresponding bromide following the procedure of Example 1.

δ (DMSO-$d_6$): 1.3 (t, J=7.3 Hz, 3 H) 2.2 (s, 3 H) 4.2 (q, J=7.1 Hz, 2 H) 5.3 (s, 2 H) 6.3 (s, 1 H) 7.4 (m, 3 H) 7.5 (m, 2 H) 8.4 (m, 2 H) 8.9 (s, 1 H)

Example 56

3-Methylbenzyl 1-ethyl-5-(isoquinolin-4-ylamino)-6-oxo-1,6-dihydropyridazine-3-carboxylate Obtained as a solid (37%) from the title compound of Preparation 40 and the corresponding bromide following the procedure of Example 7.

δ (DMSO-$d_6$): 1.3 (t, J=7.0 Hz, 3 H) 2.3 (s, 3 H) 4.2 (q, J=7.0 Hz, 2 H) 5.1 (s, 2 H) 6.3 (s, 1 H) 7.1 (m, 3 H) 7.2 (t, J=7.6 Hz, 1 H) 7.8 (m, 3 H) 8.2 (d, J=7.8 Hz, 1 H) 8.5 (s, 1 H) 9.3 (d, J=6.3 Hz, 2 H)

Example 57

3-Trifluoromethyl benzyl 1-ethyl-5-(isoquinolin-4-ylamino)-6-oxo-1,6-dihydropyridazine-3-carboxylate Obtained as a solid (21%) from the title compound of Preparation 41 and the corresponding bromide following the procedure of Example 7.

δ (DMSO-$d_6$): 1.3 (t, J=7.0 Hz, 3 H) 4.2 (q, J=7.0 Hz, 2 H) 5.3 (s, 2 H) 6.2 (s, 1 H) 7.6 (d, J=7.0 Hz, 2 H) 7.7 (m, 5 H) 8.2 (d, J=7.8 Hz, 1 H) 8.5 (s, 1 H) 9.3 (m, 2 H)

Example 58

3-Trifluoromethyl benzyl 1-ethyl-5-(4-methyl-pyridin-3-ylamino)-6-oxo-1,6-dihydropyridazine-3-carboxylate Obtained as a solid (25%) from the title compound of Preparation 41 and the corresponding bromide following the procedure of Example 1.

δ (DMSO-$d_6$): 1.3 (t, J=7.0 Hz, 3 H) 2.2 (m, 3 H) 4.2 (q, J=7.0 Hz, 2 H) 5.4 (s, 2 H) 6.3 (s, 1 H) 7.4 (d, J=5.1 Hz, 1 H) 7.6 (t, J=7.6 Hz, 1 H) 7.7 (m, 2 H) 7.8 (s, 1 H) 8.4 (m, 2 H) 8.9 (s, 1 H)

Example 59

3-Trifluoromethylbenzyl 1-ethyl-6-oxo-5-(pyridin-3-ylamino)-1,6-dihydropyridazine-3-carboxylate Obtained as a solid (25%) from the title compound of Preparation 41 and the corresponding bromide following the procedure of Example 2.

δ (DMSO-$d_6$): 1.3 (t, J=7.0 Hz, 3 H) 4.2 (q, J=7.3 Hz, 2 H) 5.4 (s, 2 H) 7.1 (s, 1 H) 7.4 (dd, J=8.2, 4.7 Hz, 1 H) 7.6 (t, J=7.6 Hz, 1 H) 7.7 (t, J=7.8 Hz, 2 H) 7.8 (d, J=9.8 Hz, 2 H) 8.3 (dd, J=4.7, 1.6 Hz, 1 H) 8.6 (d, J=2.7 Hz, 1 H) 9.2 (s, 1 H)

Example 60

2-(Benzylmethylamino)-ethyl 1-ethyl-5-(isoquinolin-4-ylamino)-6-oxo-1,6-dihydropyridazine-3-carboxylate The title compound of Preparation 37 (100 mg, 0.32 mmol), benzyl-(2-chloroethyl)-methylamine (212 mg, 0.97 mmol) and potassium carbonate (178 mg, 1.29 mmol) are suspended in dimethylformamide (5 ml) and heated overnight at 50° C. The solvent is evaporated under reduced pressure and the residue is passed through a silica-gel column, eluting first with hexane/ethyl acetate 1:1 to 1:2 and finally with ethyl acetate, to yield 38 mg of the desired final product. Yield=26%.

LRMS: m/Z 458 (M+1)$^+$

Example 61

4-Methoxybenzyl 1-ethyl-5-(isoquinolin-4-ylamino)-6-oxo-1,6-dihydropyridazine-3-carboxylate Obtained as a solid (33%) from the title compound of Preparation 43 and the corresponding bromide following the procedure of Example 7.

δ (DMSO-$d_6$): 1.3 (t, J=7.0 Hz, 3 H) 3.7 (t, 3 H) 4.2 (q, J=7.2 Hz, 2 H) 5.1 (s, 2 H) 6.3 (s, 1 H) 6.9 (d, J=8.7 Hz, 2 H)

7.2 (d, J=8.7 Hz, 2 H) 7.8 (m, 3 H) 8.3 (d, J=7.9 Hz, 1 H) 8.5 (s, 1 H) 9.3 (d, J=10.4 Hz, 2 H)

Example 62

3-Cyanobenzyl 1-ethyl-5-(4-methyl-pyridin-3-ylamino)-6-oxo-1,6-dihydropyridazine-3-carboxylate Obtained as a solid (23%) from the title compound of Preparation 42 and the corresponding bromide following the procedure of Example 1.

δ (DMSO-$d_6$): 1.3 (t, J=7.0 Hz, 3 H) 2.2 (s, 3 H) 4.2 (q, J=7.0 Hz, 2 H) 5.3 (s, 2 H) 6.3 (s, 1 H) 7.4 (d, J=5.0 Hz, 1 H) 7.6 (t, J=7.9 Hz, 1 H) 7.7 (d, J=8.3 Hz, 1 H) 7.8 (m, 2 H) 8.4 (m, 2 H) 8.9 (s, 1 H)

Example 63

3-Cyanobenzyl 1-ethyl-5-(isoquinolin-4-ylamino)-6-oxo-1,6-dihydropyridazine-3-carboxylate Obtained as a solid (25%) from the title compound of Preparation 42 and the corresponding bromide following the procedure of Example 7.

δ (DMSO-$d_6$): 1.4 (t, J=7.3 Hz, 3 H) 4.3 (q, J=7.0 Hz, 2 H) 5.3 (s, 2 H) 6.3 (s, 1 H) 7.6 (t, J=7.9 Hz, 1 H) 7.6 (m, 1 H) 7.8 (m, 5 H) 8.2 (d, J=7.9 Hz, 1 H) 8.5 (s, 1 H) 9.3 (m, 2 H)

Example 64

Cyclohexyloxycarbonyloxymethyl 1-ethyl-5-(isoquinolin-4-ylamino)-6-oxo-1,6-dihydropyridazine-3-carboxylate Obtained as a solid (61%) from the title compound of Preparation 37 and chloromethyl cyclohexyl carbonate following the procedure of Example 60.

δ (DMSO-$d_6$): 1.3 (m, 9 H) 1.6 (dd, J=9.3, 2.7 Hz, 2 H) 1.8 (dd, J=11.0, 4.4 Hz, 2 H) 4.3 (q, J=7.3 Hz, 2 H) 4.5 (m, 1 H) 5.8 (s, 2 H) 6.2 (s, 1 H) 7.8 (m, 3 H) 8.3 (d, J=7.9 Hz, 1 H) 8.5 (s, 1 H) 9.3 (m, 2 H)

Example 65

1-Cyclohexyloxycarbonyloxyethyl 1-ethyl-5-(isoquinolin-4-ylamino)-6-oxo-1,6-dihydropyridazine-3-carboxylate Obtained as a solid (90%) from the title compound of Preparation 37 and 1-chloroethyl cyclohexyl carbonate following the procedure of Example 60.

δ (DMSO-$d_6$): 1.3 (m, 6 H) 1.4 (d, J=5.5 Hz, 3 H) 1.6 (d, J=5.9 Hz, 4 H) 1.7 (m, 4 H) 4.3 (m, 2 H) 4.5 (m, 1 H) 6.2 (s, 1 H) 6.7 (q, J=5.3 Hz, 1 H) 7.8 (m, 2 H) 8.3 (d, J=7.8 Hz, 1 H) 8.5 (m, 1 H) 9.3 (m, 2 H)

Example 66

2,2-Dimethylbutyryloxymethyl 1-ethyl-5-(isoquinolin-4-ylamino)-6-oxo-1,6-dihydropyridazine-3-carboxylate Obtained as a solid (89%) from the title compound of Preparation 37 and chloromethyl 2,2-dimethylbutyrate following the procedure of Example 60.

δ (DMSO-$d_6$): 0.6 (t, J=7.4 Hz, 3 H) 1.0 (m, 6 H) 1.4 (m, 5 H) 4.3 (q, J=7.3 Hz, 2 H) 5.8 (s, 2 H) 6.2 (s, 1 H) 7.8 (m, 3 H) 8.3 (d, J=7.8 Hz, 1 H) 8.5 (s, 1 H) 9.3 (m, 2 H)

Example 67

(S)-2-Amino-4-methylpentanoyloxymethyl 1-ethyl-5-(isoquinolin-4-ylamino)-6-oxo-1,6-dihydropyridazine-3-carboxylate The title compound of Preparation 44 (0.2 g, 0.36 mmol) is dissolved in dioxane saturated with chlorohydric acid (5 ml) and stirred at room temperature for 90 min. The solvent is evaporated under reduced pressure. Ethyl ether is added and evaporated under reduced pressure, repeating this operation three more times. The residue is suspended again in ethyl ether and left at room temperature overnight. The precipitated solid is filtered and washed twice with ethyl acetate. Once dried, 170 mg of the desired final product as a dichlorohydrate are obtained. Yield=89%.

δ (DMSO-$d_6$): 0.8 (d, J=6.7 Hz, 6 H) 1.4 (t, J=7.0 Hz, 3 H) 1.6 (t, J=7.0 Hz, 2 H) 1.7 (dd, J=13.3, 6.7 Hz, 1 H) 4.0 (d, J=5.1 Hz, 2 H) 4.3 (q, J=7.0 Hz, 2 H) 5.9 (m, 2 H) 6.4 (s, 1 H) 7.9 (m, 1 H) 8.0 (d, J=3.9 Hz, 2 H) 8.4 (d, J=8.2 Hz, 1 H) 8.5 (s, 1 H) 8.6 (s, 1 H) 9.5 (m, 2 H)

Example 68

1,3,3-Trimethylbutyl 4-acetyl-1-ethyl-5-(isoquinolin-4-ylamino)-6-oxo-1,6-dihydropyridazine-3-carboxylate Obtained as a solid (23%) from de title compound of Preparation 48 and the corresponding boronic acid following the procedure of Example 21.

LRMS: m/Z 451 (M+1)$^+$.

δ (DMSO-$d_6$): 0.9 (m, 9 H) 1.16 (m, 3 H) 1.34 (m, 3 H) 1.4 (m, 1 H) 1.6 (s, 3 H) 1.62 (m, 1 H) 4.2 (q, 2 H) 5.0 (m, 1 H) 7.7 (m, 1 H) 7.8 (m, 1 H) 7.9 (d, 1 H) 8.1 (d, 1 H) 8.3 (s, 1 H) 9.2 (d, 2 H).

Example 69

3-Chlorobenzyl 4-acetyl-1-ethyl-5-(isoquinolin-4-ylamino)-6-oxo-1,6-dihydropyridazine-3-carboxylate Obtained as a solid (27%) from de title compound of Preparation 46 and the corresponding boronic acid following the procedure of Example 21.

LRMS: m/Z 477 (M+1)$^+$.

δ (DMSO-$d_6$): 1.3 (t, 3 H) 1.5 (s, 3 H) 4.1 (q, 2 H) 5.2 (s, 2 H) 7.3 (m, 1 H) 7.4 (m, 2 H) 7.5 (s, 1 H) 7.7-7.8 (m, 2 H) 7.9 (d, 1 H) 8.2 (d, 1 H) 8.3 (s, 1 H) 9.2 (m, 2 H).

Example 70

3-Methoxybenzyl 4-acetyl-1-ethyl-5-(isoquinolin-4-ylamino)-6-oxo-1,6-dihydropyridazine-3-carboxylate Obtained as a solid (30%) from de title compound of Preparation 47 and the corresponding boronic acid following the procedure of Example 21.

LRMS: m/Z 473 (M+1)$^+$.

δ (DMSO-d$_6$): 1.3 (t, 3 H) 1.5 (s, 3 H) 4.2 (q, 2 H) 5.2 (s, 2 H) 6.9 (m, 3 H) 7.3 (m, 1 H) 7.7-7.8 (m, 2 H) 7.9 (d, 1 H) 8.2 (d, 1 H) 8.3 (s, 1 H) 9.2 (m, 2 H).

Example 71

Octyl 4-acetyl-1-ethyl-5-(isoquinolin-4-ylamino)-6-oxo-1,6-dihydropyridazine-3-carboxylate Obtained as a solid (12.5%) from de title compound of Preparation 48 and the corresponding boronic acid following the procedure of Example 21.
LRMS: m/Z 465 (M+1)$^+$.
δ (DMSO-d6): 0.8 (t, J=6.6 Hz, 3 H) 1.2 (m, 10 H) 1.4 (t, J=7.3 Hz, 3 H) 1.6 (m, 5 H) 4.1 (t, J=6.6 Hz, 2 H) 4.2 (q, J=7.3 Hz, 2 H) 7.7 (dd, 1 H) 7.8 (dd, 1 H) 8.0 (d, 1 H) 8.2 (d, J=8.3 Hz, 1 H) 8.3 (s, 1 H) 9.2 (s, 2 H)

Example 72

(4E)-1,5-Dimethylhept-4-en-1-yl 4-acetyl-1-ethyl-5-(isoquinolin-4-ylamino)-6-oxo-1,6-dihydropyridazine-3-carboxylate Obtained as a solid (1.6%) from the title compound of Preparation 49 and the corresponding bromide following the procedure of Example 7.
LRMS: m/Z 463 (M+1)$^+$.
Retention Time: 18 min.

Example 73

Allyl 4-acetyl-1-ethyl-5-(isoquinolin-4-ylamino)-6-oxo-1,6-dihydropyridazine-3-carboxylate Obtained as a solid (7.2%) from de title compound of Preparation 50 and the corresponding boronic acid following the procedure of Example 21.
LRMS: m/Z 393 (M+1)$^+$.
δ (DMSO-d$_6$): 1.4 (t, J=7.0 Hz, 3 H) 1.6 (s, 3 H) 4.2 (q, J=7.0 Hz, 2 H) 4.7 (m, 2 H) 5.2 (d, J=10.4 Hz, 1 H) 5.3 (d, J=17.4 Hz, 1 H) 5.9 (m, 1 H) 7.7 (dd, 1 H) 7.8 (dd, 1 H) 8.0 (d, J=8.3 Hz, 1 H) 8.2 (d, J=8.3 Hz, 1 H) 8.3 (s, 1 H) 9.2 (d, J=3.7 Hz, 2 H)

The following examples illustrate pharmaceutical compositions according to the present invention.

COMPOSITION EXAMPLES

Composition Example 1

Preparation of Tablets

Formulation:

| | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention are mixed with 340.8 g of lactose and 85.2 g of microcrystalline cellulose. The mixture is subjected to compression moulding using a roller compactor to give a flake-like compressed material. The flake-like compressed material is pulverised using a hammer mill, and the pulverised material is screened through a 20 mesh screen. A 4.5 g portion of light silicic anhydride and 4.5 g of magnesium stearate are added to the screened material and mixed. The mixed product is subjected to a tablet making machine equipped with a die/punch system of 7.5 mm in diameter, thereby obtaining 3,000 tablets each having 150 mg in weight.

Composition Example 2

Preparation of Coated Tablets

Formulation:

| | |
|---|---|
| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidised bed granulating machine, 15 g of the compound of the present invention are mixed with 285.6 g of lactose and 122.4 g of corn starch. Separately, 22.5 g of polyvinylpyrrolidone is dissolved in 127.5 g of water to prepare a binding solution. Using a fluidised bed granulating machine, the binding solution is sprayed on the above mixture to give granulates. A 4.5 g portion of magnesium stearate is added to the obtained granulates and mixed. The obtained mixture is subjected to a tablet making machine equipped with a die/punch biconcave system of 6.5 mm in diameter, thereby obtaining 3,000 tablets, each having 150 mg in weight.

Separately, a coating solution is prepared by suspending 6.9 g of hydroxypropylmethyl-cellulose 2910, 1.2 g of polyethylene glycol 6000, 3.3 g of titanium dioxide and 2.1 g of purified talc in 72.6 g of water. Using a High Coated, the 3,000 tablets prepared above are coated with the coating solution to give film-coated tablets, each having 154.5 mg in weight.

Composition Example 3

Preparation of Capsules

Formulation:

| | |
|---|---|
| Compound of the present invention | 5.0 mg |
| Lactose monohydrate | 200 mg |
| Colloidal silicon dioxide | 2 mg |
| Corn starch | 20 mg |
| Magnesium stearate | 4 mg |

25 g of active compound, 1 Kg of lactose monohydrate, 10 g of colloidal silicon dioxide, 100 g of corn starch and 20 g of magnesium stearate are mixed. The mixture is sieved through a 60 mesh sieve, and then filled into 5,000 gelatine capsules.

Composition Example 4

Preparation of a Cream

Formulation:

| | |
|---|---|
| Compound of the present invention | 1% |
| Cetyl alcohol | 3% |
| Stearyl alcohol | 4% |
| Gliceryl monostearate | 4% |
| Sorbitan monostearate | 0.8% |
| Sorbitan monostearate POE | 0.8% |
| Liquid vaseline | 5% |
| Methylparaben | 0.18% |
| Propylparaben | 0.02% |
| Glycerine | 15% |
| Purified water csp. | 100% |

An oil-in-water emulsion cream is prepared with the ingredients listed above, using conventional methods.

The invention claimed is:
1. A compound of formula (I)

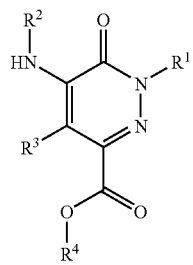

wherein
R$^1$ represents:
  a hydrogen atom;
  an alkyl, alkenyl or alkynyl group, which is optionally substituted by one or more substituents chosen from halogen atoms and hydroxy, alkoxy, aryloxy, alkylthio, arylthio, oxo, amino, mono-alkylamino, di-alkylamino, acylamino, hydroxycarbonyl, alkoxycarbonyl, carbamoyl, mono-alkylcarbamoyl, and di-alkylcarbamoyl groups;
R$^2$ represents a monocyclic or polycyclic heteroaryl group, which is optionally substituted by one or more substituents chosen from:
  halogen atoms;
  alkyl and alkylene groups, which are optionally substituted by one or more substituents chosen from halogen atoms and phenyl, hydroxy, alkoxy, aryloxy, alkylthio, arylthio, oxo, amino, mono-alkylamino, di-alkylamino, acylamino, hydroxycarbonyl, alkoxycarbonyl, carbamoyl, mono-alkylcarbamoyl, and di-alkylcarbamoyl groups; and
  phenyl, hydroxy, hydroxycarbonyl, hydroxyalkyl, alkoxycarbonyl, alkoxy, cycloalkoxy, nitro, cyano, aryloxy, alkylthio, arylthio, alkylsulfinyl, alkylsulfonyl, alkylsulfamoyl, acyl, amino, mono-alkylamino, di-alkylamino, acylamino, hydroxycarbonyl, alkoxycarbonyl, carbamoyl, mono-alkylcarbamoyl, di-alkylcarbamoyl, ureido, N'-alkylureido, N', N'-dialkylureido, alkylsulfamido, aminosuphonyl, mono-alkylaminosulfonyl, di-alkylaminosulfonyl, cyano, difluoromethoxy, and trifluoromethoxy groups;

R$^3$ represents a hydrogen atom or an alkylcarbonyl group wherein the alkyl group is optionally substituted by one or more substituents chosen from halogen atoms and phenyl, hydroxy, hydroxyalkyl, alkoxy, aryloxy, alkylthio, arylthio, oxo, amino, mono-alkylamino, di-alkylamino, acylamino, hydroxycarbonyl, alkoxycarbonyl, carbamoyl, mono-alkylcarbamoyl, and di-alkylcarbamoyl groups; and
R$^4$ represents a group of formula:

G-L1-(CRR')$_n$— wherein
n is an integer from 0 to 3;
R and R' are each independently chosen from hydrogen atoms or lower alkyl groups;
L1 is a linker chosen from a direct bond, or —O—, —CO—, —NR"—, —O(CO)NR"—, —O(CO)O—, —O—(CO)—, —(CO)O—, —NR"—(CO)— or —O(R"O)(PO)O— groups wherein R" is chosen from hydrogen atoms or lower alkyl groups;
G is chosen from hydrogen atoms or alkyl, alkenyl, alkynyl, cycloalkyl, cycloalkenyl, heterocyclyl, aryl, arylalkyl or heteroaryl groups, said groups being optionally substituted with one or more substituents chosen from:
  halogen atoms;
  alkyl and alkenyl groups, which are optionally substituted by one or more substituents chosen from halogen atoms; and
  hydroxy, alkoxy, cycloalkyloxy, alkylthio, alkylsulfinyl, alkylsulfonyl, alkylsulfamoyl, amino, mono- or di-alkylamino, acylamino, nitro, acyl, hydroxycarbonyl, alkoxycarbonyl, carbamoyl, mono-alkylcarbamoyl, di-alkylcarbamoyl, ureido, N'-alkylureido, N',N'-dialkylureido, alkylsulfamido, aminosuphonyl, mono-alkylaminosulfonyl, di-alkylaminosulfonyl, cyano, difluoromethoxy and trifluoromethoxy groups;
or pharmaceutically acceptable salts or N-oxides thereof.

2. The compound according to claim 1, wherein R$^1$ is a hydrogen atom or lower alkyl group, which is optionally substituted by one or more substituents chosen from halogen atoms and hydroxy, alkoxy, alkylthio, hydroxycarbonyl, and alkoxycarbonyl groups.

3. The compound according to claim 1, wherein R$^2$ is a monocyclic or polycyclic heteroaryl group which is optionally substituted by one or more substituents chosen from halogen atoms and alkyl, hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono-alkylamino, di-alkylamino, acylamino, carbamoyl, mono-alkylcarbamoyl, di-alkylcarbamoyl, difluoromethyl, trifluoromethyl, difluoromethoxy, and trifluoromethoxy groups.

4. The compound according to claim 3, wherein R$^2$ is a monocyclic or polycyclic N-containing heteroaryl group.

5. The compound according to claim 4, wherein the monocyclic or polycyclic N-containing heteroaryl group is optionally substituted by one or more substituents chosen from halogen atoms and lower alkyl groups.

6. The compound according to claim 1, wherein R$^4$ represents a group of formula:

G-L1-(CRR')$_n$— wherein
n is an integer from 1 to 3;
R and R' are independently chosen from hydrogen atoms and lower alkyl groups;
L1 is a linker chosen from a direct bond, or —O—, —O(CO)—, —(CO)O— or —O(CO)O— groups; and G is chosen from alkyl, cycloalkyl, heterocyclyl, aryl, or heteroaryl groups, said groups being optionally substituted with one or more substituents chosen from:
halogen atoms;
alkyl and alkenyl groups, which are optionally substituted by one or more substituents chosen from halogen atoms; and
hydroxy, alkoxy, cyano, and cycloalkyloxy groups.

7. The compound according to claim 6, wherein $R^4$ represents a group of formula:

G-L1-(CRR')$_n$— wherein
n is an integer from 1 to 3;
R and R' are independently chosen from hydrogen atoms and lower alkyl groups;
L1 is a linker chosen from a direct bond or —O—, —O(CO)— or —O(CO)O— groups; and
G is chosen from alkyl, cycloalkyl, heterocyclyl, aryl, or heteroaryl groups, said groups being optionally substituted with one or more substituents chosen from:
halogen atoms;
alkyl and alkenyl groups, which are optionally substituted by one or more substituents chosen from halogen atoms; and
hydroxy, alkoxy, and cycloalkyloxy groups.

8. The compound according to claim 7, wherein $R^4$ represents a group of formula:

G-L1-(CRR')$_n$— wherein
n is an integer from 1 to 2;
R and R' are independently chosen from hydrogen atoms and methyl groups;
L1 is a linker chosen from a direct bond or —O—, —(CO)O—, or —O(CO)O— groups; and
G is chosen from alkyl, cycloalkyl, aryl, or heteroaryl groups, said groups being optionally substituted with one or more substituents chosen from halogen atoms, and alkoxy, cyano, alkyl, and —CF$_3$ groups.

9. The compound according to claim 1, wherein $R^3$ represents a hydrogen atom or an acyl group.

10. The compound according to claim 1 chosen from:
ethyl 4-acetyl-1-ethyl-6-oxo-5-(quinolin-5-ylamino)-1,6-dihydropyridazine-3-carboxylate;
ethyl 4-acetyl-1-ethyl-6-oxo-5-(pyridin-3-ylamino)-1,6-dihydropyridazine-3-carboxylate;
ethyl 4-acetyl-1-ethyl-5-(isoquinolin-4-ylamino)-6-oxo-1,6-dihydropyridazine-3-carboxylate;
ethyl 4-acetyl-1-ethyl-5-[(4-methylpyridin-3-yl)amino]-6-oxo-1,6-dihydropyridazine-3-carboxylate;
isopropyl 4-acetyl-1-ethyl-6-oxo-5-(pyridin-3-ylamino)-1,6-dihydropyridazine-3-carboxylate;
benzyl 4-acetyl-1-ethyl-6-oxo-5-(pyridin-3-ylamino)-1,6-dihydropyridazine-3-carboxylate;
isopropyl 4-acetyl-1-ethyl-5-(isoquinolin-4-ylamino)-6-oxo-1,6-dihydropyridazine-3-carboxylate;
3-methylbutyl 4-acetyl-1-ethyl-6-oxo-5-(pyridin-3-ylamino)-1,6-dihydropyridazine-3-carboxylate;
2-methoxyethyl 4-acetyl-1-ethyl-6-oxo-5-(pyridin-3-ylamino)-1,6-dihydropyridazine-3-carboxylate;
cyclopropylmethyl 4-acetyl-1-ethyl-6-oxo-5-(pyridin-3-ylamino)-1,6-dihydropyridazine-3-carboxylate;
methyl 4-acetyl-1-ethyl-6-oxo-5-(pyridin-3-ylamino)-1,6-dihydropyridazine-3-carboxylate;
2-phenylethyl 4-acetyl-1-ethyl-6-oxo-5-(pyridin-3-ylamino)-1,6-dihydropyridazine-3-carboxylate;
benzyl 4-acetyl-1-ethyl-5-(isoquinolin-4-ylamino)-6-oxo-1,6-dihydropyridazine-3-carboxylate;
cyclohexyl 4-acetyl-1-ethyl-5-(isoquinolin-4-ylamino)-6-oxo-1,6-dihydropyridazine-3-carboxylate;
tert-butyl 4-acetyl-1-ethyl-5-(isoquinolin-4-ylamino)-6-oxo-1,6-dihydropyridazine-3-carboxylate;
cyclobutyl 4-acetyl-1-ethyl-5-(isoquinolin-4-ylamino)-6-oxo-1,6-dihydropyridazine-3-carboxylate;
cyclohexyl 4-acetyl-1-ethyl-5-[(4-methylpyridin-3-yl)amino]-6-oxo-1,6-dihydropyridazine-3-carboxylate;
1-methyl-2-phenylethyl 4-acetyl-1-ethyl-5-(isoquinolin-4-ylamino)-6-oxo-1,6-dihydropyridazine-3-carboxylate;
1-phenylethyl 4-acetyl-1-ethyl-5-(isoquinolin-4-ylamino)-6-oxo-1,6-dihydropyridazine-3-carboxylate;
tert-butyl 4-acetyl-1-ethyl-5-[(4-methylpyridin-3-yl)amino]-6-oxo-1,6- dihydropyridazine-3-carboxylate;
1-phenylethyl 4-acetyl-1-ethyl-5-[(4-methylpyridin-3-yl)amino]-6-oxo-1,6-dihydropyridazine-3-carboxylate;
sec-butyl 4-acetyl-1-ethyl-5-(isoquinolin-4-ylamino)-6-oxo-1,6-dihydropyridazine-3-carboxylate;
2-(dimethylamino)-2-oxoethyl 4-acetyl-1-ethyl-5-(isoquinolin-4-ylamino)-6-oxo-1,6-dihydropyridazine-3-carboxylate;
2-methoxy-1-methyl-2-oxoethyl 4-acetyl-1-ethyl-5-(isoquinolin-4-ylamino)-6-oxo-1,6-dihydropyridazine-3-carboxylate;
benzyl 1-ethyl-5-[(4-methylpyridin-3-yl)amino]-6-oxo-1,6-dihydropyridazine-3-carboxylate;
ethyl 1-ethyl-6-oxo-5-(pyridin-3-ylamino)-1,6-dihydropyridazine-3-carboxylate;
ethyl 1-ethyl-5-[(4-methylpyridin-3-yl)amino]-6-oxo-1,6-dihydropyridazine-3-carboxylate;
isopropyl 1-ethyl-6-oxo-5-(pyridin-3-ylamino)-1,6-dihydropyridazine-3-carboxylate;
pyridin-2-ylmethyl 1-ethyl-6-oxo-5-(pyridin-3-ylamino)-1,6-dihydropyridazine-3-carboxylate;
isopropyl 1-ethyl-5-[(4-methylpyridin-3-yl)amino]-6-oxo-1,6-dihydropyridazine-3-carboxylate;
ethyl 1-ethyl-5-(isoquinolin-4-ylamino)-6-oxo-1,6-dihydropyridazine-3-carboxylate;
isopropyl 1-ethyl-5-(isoquinolin-4-ylamino)-6-oxo-1,6-dihydropyridazine-3-carboxylate;
3-thienylmethyl 1-ethyl-5-(isoquinolin-4-ylamino)-6-oxo-1,6-dihydropyridazine-3-carboxylate;
3-thienylmethyl 1-ethyl-5-[(4-methylpyridin-3-yl)amino]-6-oxo-1,6-dihydropyridazine-3-carboxylate;
3-methoxybenzyl 1-ethyl-5-(isoquinolin-4-ylamino)-6-oxo-1,6-dihydropyridazine-3-carboxylate;
3-methoxybenzyl 1-ethyl-5-[(4-methylpyridin-3-yl)amino]-6-oxo-1,6-dihydropyridazine-3-carboxylate;
3-chlorobenzyl 1-ethyl-5-(isoquinolin-4-ylamino)-6-oxo-1,6-dihydropyridazine-3-carboxylate;
1-phenylethyl 1-ethyl-5-(isoquinolin-4-ylamino)-6-oxo-1,6-dihydropyridazine-3-carboxylate;
1-phenylethyl 1-ethyl-5-[(4-methylpyridin-3-yl)amino]-6-oxo-1,6-dihydropyridazine-3-carboxylate;
1-pyridin-4-ylethyl 1-ethyl-5-(isoquinolin-4-ylamino)-6-oxo-1,6-dihydropyridazine-3-carboxylate; 1-pyridin-4-ylethyl 1-ethyl-5-[(4-methylpyridin-3-yl)amino]-6-oxo-1,6-dihydropyridazine-3-carboxylate;
1-pyridin-4-ylethyl 1-ethyl-6-oxo-5-(pyridin-3-ylamino)-1,6-dihydropyridazine-3-carboxylate;
2,3-dihydro-1H-inden-1-yl 1-ethyl-5-(isoquinolin-4-ylamino)-6-oxo-1,6-dihydropyridazine-3-carboxylate;

2,3-dihydro-1H-inden-1-yl 1-ethyl-5-[(4-methylpyridin-3-yl)amino]-6-oxo-1,6-dihydropyridazine-3-carboxylate;
1,3,3-Trimethylbutyl 4-acetyl-1-ethyl-5-(isoquinolin-4-ylamino)-6-oxo-1,6-dihydropyridazine-3-carboxylate;
3-Chlorobenzyl 4-acetyl-1-ethyl-5-(isoquinolin-4-ylamino)-6-oxo-1,6-dihydropyridazine-3-carboxylate;
3-Methoxybenzyl 4-acetyl-1-ethyl-5-(isoquinolin-4-ylamino)-6-oxo-1,6-dihydropyridazine-3-carboxylate;
Benzyl 1-ethyl-5-(isoquinolin-4-ylamino)-6-oxo-1,6-dihydropyridazine-3-carboxylate; Octyl 4-acetyl-1-ethyl-5-(isoquinolin-4-ylamino)-6-oxo-1,6-dihydropyridazine-3-carboxylate;
1,5-Dimethylhex-4-en-1-yl 4-acetyl-1-ethyl-5-(isoquinolin-4-ylamino)-6-oxo-1,6-dihydropyridazine-3-carboxylate;
Allyl 4-acetyl-1-ethyl-5-(isoquinolin-4-ylamino)-6-oxo-1,6-dihydropyridazine-3-carboxylate;
Benzyloxycarbonylmethyl 1-ethyl-5-(isoquinolin-4-ylamino)-6-oxo-1,6-dihydropyridazine-3-carboxylate;
2-Oxo-2-phenylethyl 1-ethyl-5-(isoquinolin-4-ylamino)-6-oxo-1,6-dihydropyridazine-3-carboxylate;
Dimethylcarbamoylmethyl 1-ethyl-5-(isoquinolin-4-ylamino)-6-oxo-1,6-dihydropyridazine-3-carboxylate;
2-Phenoxyethyl 1-ethyl-5-(isoquinolin-4-ylamino)-6-oxo-1,6-dihydropyridazine-3-carboxylate;
2-Dimethylaminoethyl 1-ethyl-5-(isoquinolin-4-ylamino)-6-oxo-1,6-dihydropyridazine-3-carboxylate;
4-Bromobenzyl 1-ethyl-5-(isoquinolin-4-ylamino)-6-oxo-1,6-dihydropyridazine-3-carboxylate;
4-Bromobenzyl 1-ethyl-5-(4-methyl-pyridin-3-ylamino)-6-oxo-1,6-dihydropyridazine-3-carboxylate;
4-Bromobenzyl 1-ethyl-6-oxo-5-(pyridin-3-ylamino)-1,6-dihydropyridazine-3-carboxylate;
2-Chlorobenzyl 1-ethyl-5-(isoquinolin-4-ylamino)-6-oxo-1,6-dihydropyridazine-3-carboxylate;
2-Chlorobenzyl 1-ethyl-5-(4-methyl-pyridin-3-ylamino)-6-oxo-1,6-dihydropyridazine-3-carboxylate;
3-Methylbenzyl 1-ethyl-5-(isoquinolin-4-ylamino)-6-oxo-1,6-dihydropyridazine-3-carboxylate;
3-Trifluoromethylbenzyl 1-ethyl-5-(isoquinolin-4-ylamino)-6-oxo-1,6-dihydropyridazine-3-carboxylate;
3-Trifluoromethylbenzyl 1-ethyl-5-(4-methyl-pyridin-3-ylamino) -6-oxo-1,6-dihydropyridazine-3-carboxylate;
3-Trifluoromethylbenzyl 1-ethyl-6-oxo-5-(pyridin-3-ylamino)-1,6-dihydropyridazine-3-carboxylate;
2-(Benzylmethylamino)-ethyl 1-ethyl-5-(isoquinolin-4-ylamino)-6-oxo-1,6-dihydropyridazine-3-carboxylate;
4-Methoxybenzyl 1-ethyl-5-(isoquinolin-4-ylamino)-6-oxo-1,6-dihydropyridazine-3-carboxylate;
3-Cyanobenzyl 1-ethyl-5-(4-methyl-pyridin-3-ylamino)-6-oxo-1,6-dihydropyridazine-3-carboxylate;
3-Cyanobenzyl 1-ethyl-5-(isoquinolin-4-ylamino)-6-oxo-1,6-dihydropyridazine-3-carboxylate;
Cyclohexyloxycarbonyloxymethyl 1-ethyl-5-(isoquinolin-4-ylamino)-6-oxo-1,6-dihydropyridazine-3-carboxylate;
1-Cyclohexyloxycarbonyloxyethyl 1-ethyl-5-(isoquinolin-4-ylamino)-6-oxo-1,6-dihydropyridazine-3-carboxylate;
2,2-Dimethylbutyryloxymethyl 1-ethyl-5-(isoquinolin-4-ylamino)-6-oxo-1,6-dihydropyridazine-3-carboxylate; or (S)-2-Amino-4-methylpentanoyloxymethyl 1-ethyl-5-(isoquinolin-4-ylamino)-6-oxo-1,6-dihydropyridazine-3-carboxylate;
or a pharmaceutically acceptable salt thereof.

11. The pharmaceutical composition comprising a compound according to claim 1 in admixture with a pharmaceutically acceptable diluent or carrier.

12. The combination product comprising:
(i) a compound according to claim 1; and
(ii) another compound chosen from (a) steroids, (b) immunosuppressive agents, (c) T-cell receptor blockers, (d) antiinflammatory drugs, (e) β2-adrenergic agonists, and (f) antagonists of M3 muscarinic receptors;
for simultaneous, separate, or sequential administration to a human or animal.

* * * * *